(12) United States Patent
Marsilje, III et al.

(10) Patent No.: US 8,445,505 B2
(45) Date of Patent: May 21, 2013

(54) PYRIMIDINE DERIVATIVES AS KINASE INHIBITORS

(75) Inventors: Thomas H. Marsilje, III, San Diego, CA (US); Wenshuo Lu, San Diego, CA (US); Bei Chen, San Diego, CA (US); Xiaohui He, San Diego, CA (US); Songchun Jiang, San Diego, CA (US); Kunyong Yang, San Diego, CA (US)

(73) Assignee: IRM LLC, Hamilton (BM)

( * ) Notice: Subject to any disclaimer, the term of this patent is extended or adjusted under 35 U.S.C. 154(b) by 112 days.

(21) Appl. No.: 13/000,999

(22) PCT Filed: Jun. 24, 2009

(86) PCT No.: PCT/US2009/048509
§ 371 (c)(1),
(2), (4) Date: Dec. 22, 2010

(87) PCT Pub. No.: WO2009/158431
PCT Pub. Date: Dec. 30, 2009

(65) Prior Publication Data
US 2011/0112096 A1    May 12, 2011

Related U.S. Application Data

(60) Provisional application No. 61/075,583, filed on Jun. 25, 2008.

(51) Int. Cl.
*C07D 403/12* (2006.01)
*A61K 31/506* (2006.01)

(52) U.S. Cl.
USPC .......................... 514/272; 544/297; 544/333

(58) Field of Classification Search
USPC .......................................... 544/297; 514/275
See application file for complete search history.

(56) References Cited

U.S. PATENT DOCUMENTS

| | | |
|---|---|---|
| 2006/0270694 A1 | 11/2006 | Wong |
| 2008/0176881 A1 | 7/2008 | Michellys et al. |
| 2010/0298295 A1 | 11/2010 | Marsilje et al. |
| 2011/0112063 A1 | 5/2011 | Marsilje et al. |

FOREIGN PATENT DOCUMENTS

| | | |
|---|---|---|
| WO | 00/12485 A1 | 3/2000 |
| WO | 01/07027 A2 | 2/2001 |
| WO | 01/64655 A1 | 9/2001 |
| WO | 03/018021 A1 | 3/2003 |
| WO | 03/026664 A1 | 4/2003 |
| WO | 03/026666 A1 | 4/2003 |
| WO | 03/078404 A1 | 9/2003 |
| WO | 2004/080980 A1 | 9/2004 |
| WO | 2005/016893 A2 | 2/2005 |
| WO | 2005/016894 A1 | 2/2005 |
| WO | 2005/026130 A1 | 3/2005 |
| WO | 2005/026158 A1 | 3/2005 |
| WO | 2006/074057 A2 | 7/2006 |
| WO | WO 2006/074057 A2 * | 7/2006 |
| WO | 2006/137706 A1 | 12/2006 |
| WO | 2007/027238 A2 | 3/2007 |
| WO | 2007/031829 A2 | 3/2007 |
| WO | 2008/005538 A2 | 1/2008 |
| WO | 2008/015250 A1 | 2/2008 |
| WO | 2008/051547 A1 | 5/2008 |
| WO | WO 2008/073687 A2 | 6/2008 |
| WO | 2008/083465 A1 | 7/2008 |
| WO | 2008/127349 A2 | 10/2008 |
| WO | 2009/017838 A2 | 2/2009 |
| WO | 2009/067081 A1 | 5/2009 |
| WO | 2009/103652 A1 | 8/2009 |

* cited by examiner

*Primary Examiner* — Michael Barker
(74) *Attorney, Agent, or Firm* — Emily Tongeo Wu; Genomics Institute of the Novartis Research Foundation

(57) ABSTRACT

The invention provides novel pyrimidine derivatives of formula (I) and pharmaceutical compositions thereof, and methods for using such compounds. For example, the pyrimidine derivatives of the invention may be used to treat, ameliorate or prevent a condition which responds to inhibition of insulin-like growth factor (IGF-IR) or analplastic lymphoma kinase (ALK).

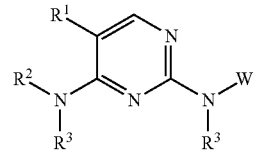

(1)

8 Claims, No Drawings

PYRIMIDINE DERIVATIVES AS KINASE INHIBITORS

CROSS-REFERENCE TO RELATED APPLICATIONS

This application is a 371 U.S. national phase application of international application number PCT/US2009/048509 filed 24 Jun. 2009, which application claims priority to U.S. provisional patent application No. 61/075,583 filed 25 Jun. 2008, which is incorporated herein by reference in its entirety and for all purposes.

TECHNICAL FIELD

The invention relates to protein kinase inhibitors, more particularly novel pyrimidine derivatives and pharmaceutical compositions thereof, and their use as pharmaceuticals.

BACKGROUND ART

Insulin-like growth factor (IGF-1) signaling is highly implicated in cancer, with the IGF-1 receptor (IGF-1R) as the predominating factor. IGR-1R is important for tumor transformation and survival of malignant cells, but is only partially involved in normal cell growth. Targeting of IGF-1R has been suggested to be a promising option for cancer therapy. (Larsson et al., Br. J. Cancer 92:2097-2101 (2005)).

Anaplastic lymphoma kinase (ALK), a member of the insulin receptor superfamily of receptor tyrosine kinases, has been implicated in oncogenesis in hematopoietic and non-hematopoietic tumors. The aberrant expression of full-length ALK receptor proteins has been reported in neuroblastomas and glioblastomas; and ALK fusion proteins have occurred in anaplastic large cell lymphoma. The study of ALK fusion proteins has also raised the possibility of new therapeutic treatments for patients with ALK-positive malignancies. (Pulford et al., Cell. Mol. Life. Sci. 61:2939-2953 (2004)).

Because of the emerging disease-related roles of IGF-1R and ALK, there is a continuing need for compounds which may be useful for treating and preventing a disease which responds to inhibition of IGF-1R and ALK.

DISCLOSURE OF THE INVENTION

The invention relates to novel pyrimidine derivatives and pharmaceutical compositions thereof, and their use as pharmaceuticals.

In one aspect, the invention provides a compound of Formula (1):

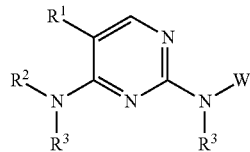

(1)

or a physiologically acceptable salt thereof;

wherein W is

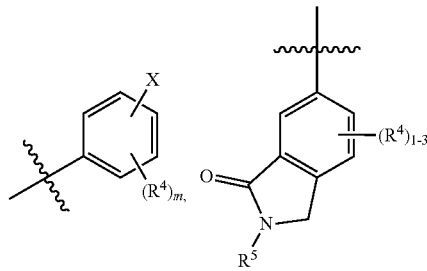

or W';

W' is pyridyl, isoquinolinyl, quinoliny, naphthalenyl, cinnolin-5-yl or [3-($C_{1-6}$ alkyl)-(2,3,4,5-tetrahydro-1H-benzo[d]azepin-7yl], each of which is optionally substituted with 1-3 $R^9$; and said pyridyl, isoquinolinyl, quinolinyl and napthalenyl are each substituted on a ring carbon with

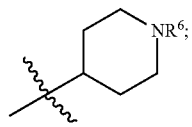

X is —C(R)=N—O—$R^7$, C(O)NR$R^7$, C(O)NR—(CR$_2$)$_n$—NR$R^7$, —(CR$_2$)$_p$NRR wherein two R groups together with N in NRR form a 5-6 membered ring containing 1-3 heteroatoms selected from N, O and S and optionally substituted with 1-3 $R^9$, or a $C_{5-7}$ carbocycle optionally substituted with oxo, =N—OH or $R^9$; or X is quinolinyl, (1,2,3,4-tetrahydroisoquinolin-6-yl) or a 5-6 membered heteroaryl having 1-3 heteroatoms selected from N, O and S, each of which is optionally substituted with 1-3 $R^9$;

$R^1$ is halo, $C_{1-6}$ alkyl, or a halo-substituted $C_{1-6}$ alkyl;

$R^2$ is a 5-6 membered heteroaryl having 1-3 heteroatoms selected from N, O and S, and is optionally substituted with $C_{1-6}$ alkyl, $C_{1-6}$ haloalkyl or $C_{3-7}$ cycloalkyl;

each $R^3$ is H;

$R^4$ is halo, hydroxyl, $C_{1-6}$ alkyl, $C_{1-6}$ alkoxy, halo-substituted $C_{1-6}$ alkyl, halo-substituted $C_{1-6}$ alkoxy, cyano or C(O)O$_{0-1}$$R^8$;

$R^5$ is H or

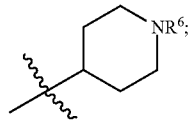

$R^6$ is H, $C_{1-6}$ alkyl, $C_{2-6}$ alkenyl or $C_{2-6}$ alkynyl, each of which may be optionally substituted with halo and/or hydroxyl groups; —(CR$_2$)$_p$—O$R^7$, —(CR$_2$)$_p$—CH(OH)C$_t$F$_{2t+1}$ wherein t is 1-3, (CR$_2$)$_p$—CN; (CR$_2$)$_p$—NR($R^7$), —(CR$_2$)$_p$—C(O)O$R^7$, (CR$_2$)$_p$NR(CR$_2$)$_p$O$R^7$, (CR$_2$)$_p$NR-L-C(O)$R^8$, C(O)(CR$_2$)$_q$O$R^8$, —C(O)O—(CR$_2$)$_p$—NR$R^7$, —C(O)—(CR$_2$)$_p$—O$R^7$, L-Y, -L-C(O)$R^7$, -L-C(O)—NR$R^7$, -L-C(O)—NR—(CR$_2$)$_p$—NR$R^7$, -L-C(O)NR(CR$_2$)$_p$O$R^7$, -L-C(O)—(CR$_2$)$_q$—NR—C(O)—R$^8$, -L-C(O)NR(CR$_2$)$_p$SR$^7$, -L-C(O)NR(CR$_2$)$_p$S(O)$_{1-2}$R$^8$,
-L-S(O)$_2$R$^8$, -L-S(O)$_2$—(CR$_2$)$_q$—NRR$^7$, -L-S(O)$_2$NR(CR$_2$)$_p$NR(R$^7$) or
-L-S(O)$_2$NR(CR$_2$)$_p$OR$^7$;
alternatively, R$^6$ is a radical selected from formula (a), (b), (c) or (d):

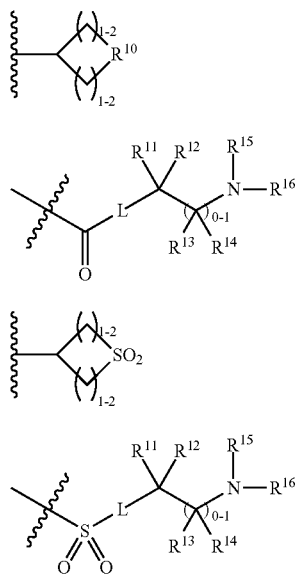

R$^{10}$ is O, S, NR$^{17}$, wherein R$^{17}$ is H, C$_{1-6}$ alkyl, SO$_2$R$^{8a}$ or CO$_2$R$^{8a}$;
R$^{11}$, R$^{12}$, R$^{13}$, R$^{14}$, R$^{15}$ and R$^{16}$ are independently selected from H; C$_{1-6}$ alkoxy; C$_{1-6}$ alkyl, C$_{2-6}$ alkenyl or C$_{2-6}$ alkynyl, each of which may be optionally substituted with halo, amino or hydroxyl groups; or R$^{11}$ and R$^{12}$, R$^{12}$ and R$^{15}$, R$^{15}$ and R$^{16}$, R$^{13}$ and R$^{14}$, or R$^{13}$ and R$^{15}$ together with the atoms to which they are attached may form a 3-7 membered saturated, unsaturated or partially unsaturated ring containing 1-3 heteroatoms selected from N, O and S, and optionally substituted with oxo and 1-3 R$^9$ groups;
L is (CR$_2$)$_{1-4}$ or a bond;
Y is C$_{3-7}$ carbocyclic ring, C$_{6-10}$ aryl, or a 5-10 membered heteroaryl or 4-10 membered heterocyclic ring, each of which is optionally substituted with 1-3 R$^9$ groups;
R$^7$, R$^8$ and R$^{8a}$ are independently C$_{1-6}$ alkyl, C$_{2-6}$ alkenyl or C$_{2-6}$ alkynyl, each of which may be optionally substituted with halo, NRR$^{7a}$, hydroxyl or cyano; (CR$_2$)$_q$Y or C$_{1-6}$ alkoxy; or R$^7$ is H;
R$^9$ is R$^4$, C(O)NRR$^7$ or NRR$^7$;
R and R$^{7a}$ are independently H or C$_{1-6}$ alkyl;
R and R$^7$ together with N in each NRR$^7$, and R and R$^{7a}$ together with N in NRR$^{7a}$ may form a 5-6 membered ring containing 1-3 heteroatoms selected from N, O and S, and optionally substituted with oxo and 1-3 R$^4$ groups;
m is 2-4;
n and p are independently 1-4; and
q is 0-4.
In the above Formula (1), R$^2$ may be pyrazolyl or isoxazolyl, each of which is substituted with C$_{1-6}$ alkyl or C$_{3-7}$ cycloalkyl.

In one embodiment, the invention provides a compound of Formula (2):

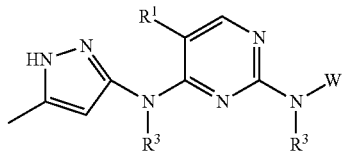

(2)

wherein W is W';
W' is pyridyl optionally substituted with C$_{1-6}$ alkyl, isoquinolinyl, quinolinyl, naphthalenyl, cinnolin-5-yl optionally substituted with C$_{1-6}$ alkyl or [3-(C$_{1-6}$ alkyl)-(2,3,4,5-tetrahydro-1H-benzo[d]azepin-7yl]; and said pyridyl, isoquinolinyl, quinolinyl and napthalenyl are each substituted on a ring carbon with

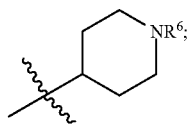

R$^6$ is H, C$_{1-6}$ alkyl, C$_{2-6}$ alkenyl or C$_{2-6}$ alkynyl, each of which may be optionally substituted with halo, amino, hydroxyl or alkoxy; —(CR$_2$)$_p$—CH(OH)C$_t$F$_{2t+1}$ wherein t is 1,
-L-C(O)—NRR$^7$ or -L-S(O)$_2$R$^8$;
L is (CR$_2$)$_{1-4}$;
R$^1$ and R$^7$ are independently H or C$_{1-6}$ alkyl;
R$^8$ is C$_{1-6}$ alkyl; and
R$^1$ and R$^3$ are as defined in Formula (1).
In another embodiment, the invention provides a compound of Formula (3):

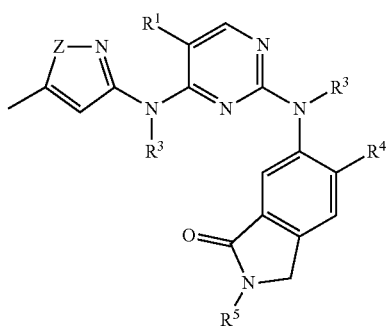

(3)

wherein Z is NH or O;
R$^4$ is halo or C$_{1-6}$ alkyl;
R$^5$ is H or

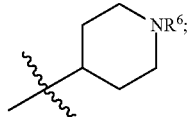

R$^6$ is H; and
R$^1$ and R$^3$ are as defined in Formula (1).

In yet another embodiment, the invention provides a compound of Formula (4):

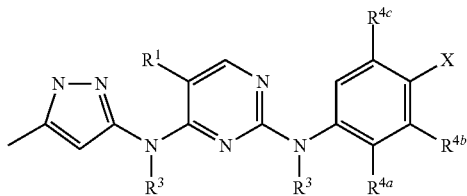

(4)

wherein one of $R^{4a}$, $R^{4b}$ and $R^{4c}$ is H and the others are independently halo, $C_{1-6}$alkyl, $C_{1-6}$ alkoxy, halo-substituted $C_{1-6}$ alkyl or halo-substituted $C_{1-6}$ alkoxy; and
X is as defined in Formula (1).

In the above Formula (4), X may be —C(R)=N—O—$R^7$, C(O)NR$R^7$, C(O)NR—(CR$_2$)$_n$—NR$R^7$ or —(CR$_2$)$_p$NRR wherein two R groups together with N in NRR form morpholinyl;

$R^7$ is H or $C_{1-6}$ alkyl optionally substituted with hydroxyl or NR$R^{7a}$;

each R is H or $C_{1-6}$ alkyl;

R and $R^7$ together with N in each NR$R^7$ and R and $R^{7a}$ together with N in NR$R^{7a}$ may form a 5-6 membered ring containing 1-2 heteroatoms selected from N, O and S; and n and p are independently 1-4. Alternatively, X may be quinolinyl, (1,2,3,4-tetrahydroisoquinolin-6-yl) or a 5-membered heteroaryl selected from pyrazolyl, pyridyl, thiophenyl, furanyl, imidazolyl, isoxazolyl, oxazolyl or thiaxolyl, each of which is optionally substituted with $C_{1-6}$ alkyl, hydroxyl, or C(O)NR$R^7$; $R^7$ is H or $C_{1-6}$ alkyl; and R is H or $C_{1-6}$ alkyl.

In another embodiment, the invention provides a compound of Formula (5):

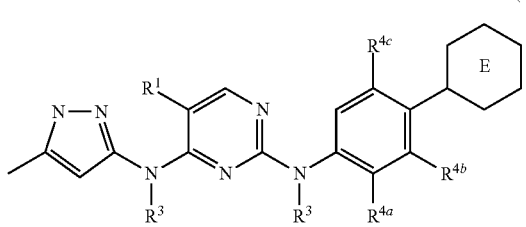

(5)

wherein one of $R^{4a}$, $R^{4b}$ and $R^{4c}$ is H and the others are independently halo, $C_{1-6}$ alkyl, $C_{1-6}$ alkoxy, halo-substituted $C_{1-6}$ alkyl or halo-substituted $C_{1-6}$ alkoxy;
Ring E is a $C_6$ carbocycle optionally substituted with oxo, =N—OH or $R^9$;
$R^9$ is hydroxyl or NR$R^7$;
R is H or $C_{1-6}$ alkyl;
$R^7$ is $C_{1-6}$ alkyl or (CR$_2$)$_q$Y and Y is $C_3$ cycloalkyl;
alternatively, R and $R^7$ together with N in NR$R^7$ forms morpholinyl, piperidinyl, piperazinyl, ($C_{1-6}$ alkyl)-piperazinyl, or pyrrolidinyl, each of which is optionally substituted with hydroxyl; and
$R^1$ and $R^3$ are as defined in Formula (1).

In the above Formula (4) and (5), $R^{4b}$ may be H. In other examples, $R^{4a}$ and $R^{4c}$ are independently halo, $C_{1-6}$ alkyl, $C_{1-6}$ alkoxy, halo-substituted $C_{1-6}$ alkyl or halo-substituted $C_{1-6}$ alkoxy.

In the above Formula (1)-(5), $R^1$ is chloro or a halo-substituted $C_{1-6}$ alkyl. In other examples, $R^3$ is H.

In another aspect, the present invention provides pharmaceutical compositions comprising a compound having Formula (1), (2), (3), (4) or (5), and a physiologically acceptable excipient.

In yet another aspect, the invention provides methods for inhibiting IGF-1R in a cell, comprising contacting the cell with an effective amount of a compound having Formula (1), (2), (3), (4) or (5) or a pharmaceutical composition thereof.

The invention also provides methods to treat, ameliorate or prevent a condition which responds to inhibition of IGF-1R or anaplastic lymphoma kinase (ALK) in a mammal suffering from said condition, comprising administering to the mammal a therapeutically effective amount of a compound having Formula (1), (2), (3), (4) or (5) or a pharmaceutical composition thereof, and optionally in combination with a second therapeutic agent. Alternatively, the present invention provides for the use of a compound having Formula (1), (2), (3), (4) or (5), and optionally in combination with a second therapeutic agent, in the manufacture of a medicament for treating a condition mediated by IGF-1R or ALK. The compounds of the invention may be administered, for example, to a mammal suffering from an autoimmune disease, a transplantation disease, an infectious disease or a cell proliferative disorder. In particular examples, the compounds of the invention may be used alone or in combination with a chemotherapeutic agent to treat a cell proliferative disorder, including but not limited to, multiple myeloma, neuroblastoma, synovial, hepatocellular, Ewing's Sarcoma or a solid tumor selected from a osteosarcoma, melanoma, and tumor of breast, renal, prostate, colorectal, thyroid, ovarian, pancreatic, lung, uterine or gastrointestinal tumor.

Definitions

"Alkyl" refers to a moiety and as a structural element of other groups, for example halo-substituted-alkyl and alkoxy, and may be straight-chained or branched. An optionally substituted alkyl, alkenyl or alkynyl as used herein may be optionally halogenated (e.g., $CF_3$), or may have one or more carbons that is substituted or replaced with a heteroatom, such as NR, O or S (e.g., —OCH$_2$CH$_2$O—, alkylthiols, thioalkoxy, alkylamines, etc).

"Aryl" refers to a monocyclic or fused bicyclic aromatic ring containing carbon atoms. "Arylene" means a divalent radical derived from an aryl group. For example, an aryl group may be phenyl, indenyl, indanyl, naphthyl, or 1,2,3,4-tetrahydronaphthalenyl, which may be optionally substituted in the ortho, meta or para position.

"Heteroaryl" as used herein is as defined for aryl above, where one or more of the ring members is a heteroatom. For example, a heteroaryl substituent for use in the compounds of the invention may be a monocyclic or bicyclic 5-10 membered heteroaryl containing 1-4 heteroatoms selected from N, O, and S. Examples of heteroaryls include but are not limited to pyridyl, pyrazinyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, benzotriazolyl, tetrazolyl, pyrazolyl, thienyl, pyrrolyl, isoquinolinyl, purinyl, thiazolyl, tetrazinyl, benzothiazolyl, oxadiazolyl, benzoxadiazolyl, etc.

A "carbocyclic ring" as used herein refers to a saturated or partially unsaturated, monocyclic, fused bicyclic or bridged polycyclic ring containing carbon atoms, which may optionally be substituted, for example, with =O. Examples of carbocyclic rings include but are not limited to cyclopropyl, cyclobutyl, cyclopentyl, cyclohexyl, cyclopropylene, cyclohexanone, etc.

A "heterocyclic ring" as used herein is as defined for a carbocyclic ring above, wherein one or more ring carbons is a heteroatom. For example, a heterocyclic ring for use in the compounds of the invention may be a 4-7 membered heterocyclic ring containing 1-3 heteroatoms selected from N, O and S, or a combination thereof such as —S(O) or —S(O)$_2$—. Examples of heterocyclic rings include but are not limited to azetidinyl, morpholino, pyrrolidinyl, pyrrolidinyl-2-one, piperazinyl, piperidinyl, piperidinylone, 1,4-dioxa-8-aza-spiro[4.5]dec-8-yl, 1,2,3,4-tetrahydroquinolinyl, etc. Heterocyclic rings as used herein may encompass bicyclic amines and bicyclic diamines.

As used herein, an H atom in any substituent groups (e.g., CH$_2$) encompasses all suitable isotopic variations, e.g., H, $^2$H and $^3$H.

The term "pharmaceutical combination" as used herein refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

"Mammal" refers to any animal classified as a mammal, including humans, domestic and farm animals, and zoo, sports, or pet animals, such as dogs, cats, cattle, horses, sheep, pigs, goats, rabbits, etc. In particular examples, the mammal is human.

The term "administration" or "administering" of the subject compound means providing a compound of the invention and prodrugs thereof to a subject in need of treatment. Administration "in combination with" one or more further therapeutic agents includes simultaneous (concurrent) and consecutive administration in any order, and in any route of administration.

An "effective amount" of a compound is an amount sufficient to carry out a specifically stated purpose. An "effective amount" may be determined empirically and in a routine manner, in relation to the stated purpose.

The term "therapeutically effective amount" refers to an amount of a compound (e.g., an IGF-1R antagonist) effective to "treat" an IGF-1R-mediated disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

The term "cancer" refers to the physiological condition in mammals that is typically characterized by unregulated cell growth/proliferation. Examples of cancer include, but are not limited to: carcinoma, lymphoma, blastoma, and leukemia. More particular examples of cancers include, but are not limited to: chronic lymphocytic leukemia (CLL), lung, including non small cell (NSCLC), breast, ovarian, cervical, endometrial, prostate, colorectal, intestinal carcinoid, bladder, gastric, pancreatic, hepatic (hepatocellular), hepatoblastoma, esophageal, pulmonary adenocarcinoma, mesothelioma, synovial sarcoma, osteosarcoma, head and neck squamous cell carcinoma, juvenile nasopharyngeal angiofibromas, liposarcoma, thyroid, melanoma, basal cell carcinoma (BCC), medulloblastoma and desmoid.

"Treating" or "treatment" or "alleviation" refers to both therapeutic treatment and prophylactic or preventative measures, wherein the object is to prevent or slow down (lessen) the targeted pathologic disease or condition or disorder. Those in need of treatment include those already with the disorder as well as those prone to having the disorder or those in whom the disorder is to be prevented (prophylaxis). When the IGF-1R-mediated disorder is cancer, a subject or mammal is successfully "treated" or shows a reduced tumor burden if, after receiving a therapeutic amount of an IGF-1R antagonist according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the IGF-1R antagonist may prevent growth and/or kill existing cancer cells, it may be cytostatic and/or cytotoxic. Reduction of these signs or symptoms may also be felt by the patient.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Furthermore, a "chemotherapeutic agent" may include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

MODES OF CARRYING OUT THE INVENTION

The invention provides novel pyrimidine derivatives and pharmaceutical compositions thereof, and methods for using such compounds.

In one aspect, the invention provides a compound of Formula (1):

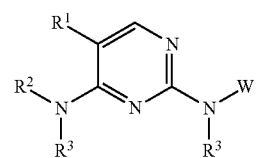

(1)

or a physiologically acceptable salt thereof;

wherein W is

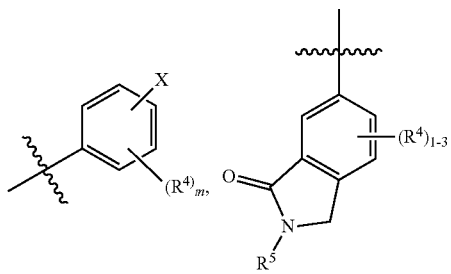

or W';

W' is pyridyl, isoquinolinyl, quinoliny, naphthalenyl, cinnolin-5-yl or [3-($C_{1-6}$ alkyl)-(2,3,4,5-tetrahydro-1H-benzo[d]azepin-7yl], each of which is optionally substituted with 1-3 $R^9$; and said pyridyl, isoquinolinyl, quinolinyl and napthalenyl are each substituted on a ring carbon with

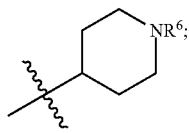

X is —C(R)=N—O—$R^7$, C(O)NR$R^7$, C(O)NR—(CR$_2$)$_n$—NR$R^7$, —(CR$_2$)$_p$NRR wherein two R groups together with N in NRR form a 5-6 membered ring containing 1-3 heteroatoms selected from N, O and S and optionally substituted with 1-3 $R^9$, or a $C_{5-7}$ carbocycle optionally substituted with oxo, =N—OH or $R^9$; or X is quinolinyl, (1,2,3,4-tetrahydroisoquinolin-6-yl) or a 5-6 membered heteroaryl having 1-3 heteroatoms selected from N, O and S, each of which is optionally substituted with 1-3 $R^9$;

$R^1$ is halo, $C_{1-6}$ alkyl, or a halo-substituted $C_{1-6}$ alkyl;

$R^2$ is a 5-6 membered heteroaryl having 1-3 heteroatoms selected from N, O and S, and is optionally substituted with $C_{1-6}$ alkyl, $C_{1-6}$ haloalkyl or $C_{3-7}$ cycloalkyl;

each $R^3$ is H;

$R^4$ is halo, hydroxyl, $C_{1-6}$ alkyl, $C_{1-6}$ alkoxy, halo-substituted $C_{1-6}$ alkyl, halo-substituted $C_{1-6}$ alkoxy, cyano or C(O)$O_{0-1}R^8$;

$R^5$ is H or

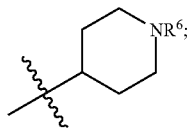

$R^6$ is H, $C_{1-6}$ alkyl, $C_{2-6}$ alkenyl or $C_{2-6}$ alkynyl, each of which may be optionally substituted with halo and/or hydroxyl groups; —(CR$_2$)$_p$—O$R^7$, —(CR$_2$)$_p$—CH(OH)C$_t$F$_{2t+1}$ wherein t is 1-3, (CR$_2$)$_p$—CN; (CR$_2$)$_p$—NR(R$^7$), —(CR$_2$)$_p$—C(O)O$R^7$, (CR$_2$)$_p$NR(CR$_2$)$_p$O$R^7$, (CR$_2$)$_p$NR-L-C(O)$R^8$, C(O)(CR$_2$)$_q$O$R^8$, —C(O)O—(CR$_2$)$_p$—NR$R^7$, —C(O)—(CR$_2$)$_p$—O$R^7$, L-Y, -L-C(O)$R^7$, -L-C(O)—NR$R^7$, -L-C(O)—NR—(CR$_2$)$_p$NR$R^7$, -L-C(O)NR(CR$_2$)$_p$O$R^7$,
-L-C(O)—(CR$_2$)$_q$—NR—C(O)—$R^8$, -L-C(O)NR(CR$_2$)$_p$S$R^7$, -L-C(O)NR(CR$_2$)$_p$S(O)$_{1-2}R^8$,
-L-S(O)$_2R^8$, -L-S(O)$_2$—(CR$_2$)$_q$—NR$R^7$, -L-S(O)$_2$NR(CR$_2$)$_p$NR(R$^7$) or
-L-S(O)$_2$NR(CR$_2$)$_p$O$R^7$;

alternatively, $R^6$ is a radical selected from formula (a), (b), (c) or (d):

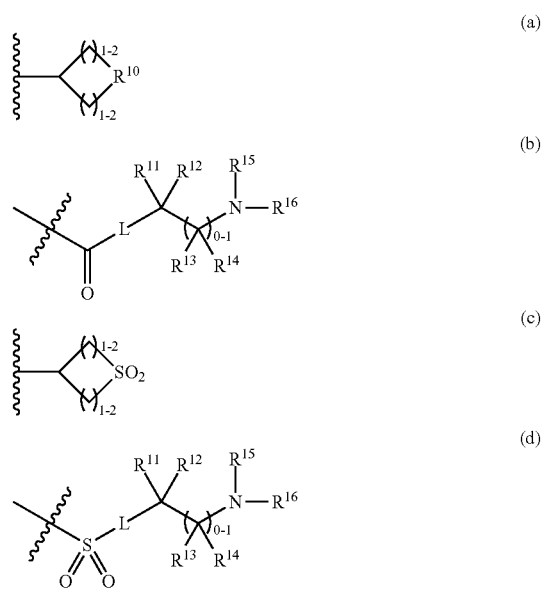

$R_{10}$ is O, S, NR$^{17}$ wherein R$^{17}$ is H, $C_{1-6}$ alkyl, SO$_2R^{8a}$ or CO$_2R^{8a}$;

$R^{11}$, $R^{12}$, $R^{13}$, $R^{14}$, $R^{15}$ and $R^{16}$ are independently selected from H; $C_{1-6}$ alkoxy; $C_{1-6}$ alkyl, $C_{2-6}$ alkenyl or $C_{2-6}$ alkynyl, each of which may be optionally substituted with halo, amino or hydroxyl groups; or $R^{11}$ and $R^{12}$, $R^{12}$ and $R^{15}$, $R^{15}$ and $R^{16}$, $R^{13}$ and $R^{14}$, or $R^{13}$ and $R^{15}$ together with the atoms to which they are attached may form a 3-7 membered saturated, unsaturated or partially unsaturated ring containing 1-3 heteroatoms selected from N, O and S, and optionally substituted with oxo and 1-3 $R^9$ groups;

L is (CR$_2$)$_{1-4}$ or a bond;

Y is $C_{3-7}$ carbocyclic ring, $C_{6-10}$ aryl, or a 5-10 membered heteroaryl or 4-10 membered heterocyclic ring, each of which is optionally substituted with 1-3 $R^9$ groups;

$R^7$, $R^8$ and $R^{8a}$ are independently $C_{1-6}$ alkyl, $C_{2-6}$ alkenyl or $C_{2-6}$ alkynyl, each of which may be optionally substituted with halo, NR$R^{7a}$, hydroxyl or cyano; (CR$_2$)$_q$Y or $C_{1-6}$ alkoxy; or $R^7$ is H;

$R^9$ is $R^4$, C(O)NR$R^7$ or NR$R^7$;

R and $R^{7a}$ are independently H or $C_{1-6}$ alkyl;

R and $R^7$ together with N in each NR$R^7$, and R and $R^{7a}$ together with N in NR$R^{7a}$ may form a 5-6 membered ring containing 1-3 heteroatoms selected from N, O and S, and optionally substituted with oxo and 1-3 $R^4$ groups;

m is 2-4;

n and p are independently 1-4; and q is 0-4.

In one embodiment, the invention provides a compound of Formula (2):

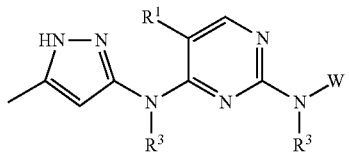

(2)

wherein W is W';
W' is pyridyl optionally substituted with $C_{1-6}$ alkyl, isoquinolinyl, quinolinyl, naphthalenyl, cinnolin-5-yl optionally substituted with $C_{1-6}$ alkyl or [3-($C_{1-6}$ alkyl)-(2,3,4,5-tetrahydro-1H-benzo[d]azepin-7yl]; and said pyridyl, isoquinolinyl, quinolinyl and napthalenyl are each substituted on a ring carbon with

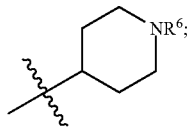

$R^6$ is H, $C_{1-6}$ alkyl, $C_{2-6}$ alkenyl or $C_{2-6}$ alkynyl, each of which may be optionally substituted with halo, amino, hydroxyl or alkoxy; —$(CR_2)_p$—$CH(OH)C_tF_{2t+1}$ wherein t is 1,
-L-C(O)—$NRR^7$ or -L-S(O)$_2R^8$;
L is $(CR_2)_{1-4}$;
R and $R^7$ are independently H or $C_{1-6}$ alkyl;
$R^8$ is $C_{1-6}$ alkyl; and
$R^1$ and $R^3$ are as defined in Formula (1).

In another embodiment, the invention provides a compound of Formula (3):

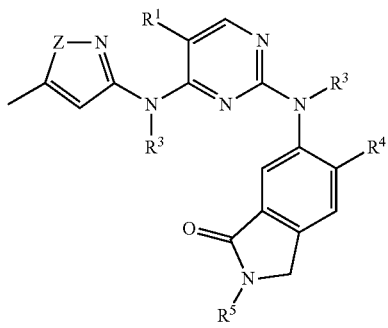

(3)

wherein Z is NH or O;
$R^4$ is halo or $C_{1-6}$ alkyl;
$R^5$ is H or

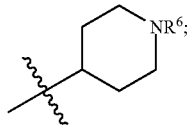

$R^6$ is H; and
$R^1$ and $R^3$ are as defined in Formula (1).

In yet another embodiment, the invention provides a compound of Formula (4):

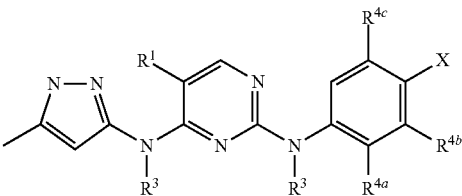

(4)

wherein one of $R^{4a}$, $R^{4b}$ and $R^{4c}$ is H and the others are independently halo, $C_{1-6}$ alkyl, $C_{1-6}$ alkoxy, halo-substituted $C_{1-6}$ alkyl or halo-substituted $C_{1-6}$ alkoxy; and
X is as defined in Formula (1).

In another embodiment, the invention provides a compound of Formula (5):

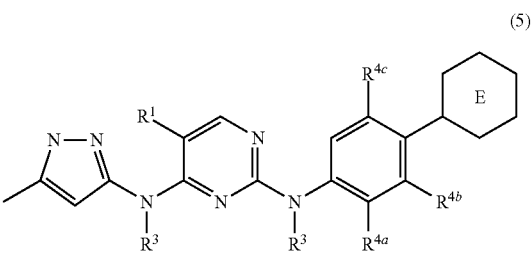

(5)

wherein one of $R^{4a}$, $R^{4b}$ and $R^{4c}$ is H and the others are independently halo, $C_{1-6}$ alkyl, $C_{1-6}$ alkoxy, halo-substituted $C_{1-6}$ alkyl or halo-substituted $C_{1-6}$ alkoxy;
Ring E is a $C_6$ carbocycle optionally substituted with oxo, =N—OH or $R^9$;
$R^9$ is hydroxyl or $NRR^7$;
R is H or $C_{1-6}$ alkyl;
$R^7$ is $C_{1-6}$ alkyl or $(CR_2)_qY$ and Y is $C_3$ cycloalkyl;
alternatively, R and $R^7$ together with N in $NRR^7$ forms morpholinyl, piperidinyl, piperazinyl, ($C_{1-6}$ alkyl)-piperazinyl, or pyrrolidinyl, each of which is optionally substituted with hydroxyl; and
$R^1$ and $R^3$ are as defined in Formula (1).

In each of the above formula, any asymmetric carbon atoms may be present in the (R)-, (S)- or (R,S)-configuration. The compounds may thus be present as mixtures of isomers or as pure isomers, for example, as pure enantiomers or diastereomers. The invention further encompasses possible tautomers of the inventive compounds.

Any formula given herein is also intended to represent unlabeled forms as well as isotopically labeled forms of the compounds. Isotopically labeled compounds have structures depicted by the formulas given herein, except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively.

The invention includes various isotopically labeled compounds as defined herein, for example, those into which radioactive isotopes such as $^3H$, $^{13}C$, and $^{14}C$, are present. Such isotopically labelled compounds are useful in metabolic studies (with, for example, $^{14}C$), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In other examples, an $^{18}$F or labeled compound may be used for PET or SPECT studies. Isotopic variations of the compounds have the potential to change a compound's metabolic fate and/or create small changes in physical properties such as hydrophobicity, and the like. Isotopic variations also have the potential to enhance efficacy and safety, enhance bioavailability and half-life, alter protein binding, change biodistribution, increase the proportion of active metabolites and/or decrease the formation of reactive or toxic metabolites. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

In each of the above formula, each optionally substituted moiety may be substituted with $C_{1-6}$ alkyl, $C_{2-6}$ alkenyl or $C_{3-6}$ alkynyl, each of which may be optionally halogenated or optionally having a carbon that may be replaced or substituted with N, S, O, or a combination thereof (for example, hydroxyl $C_1$-$C_8$alkyl, $C_1$-$C_8$alkoxy $C_1$-$C_8$alkyl); halo, amino, amidino, $C_{1-6}$ alkoxy; hydroxyl, methylenedioxy, carboxy; $C_{1-8}$ alkylcarbonyl, $C_{1-8}$alkoxycarbonyl, carbamoyl, $C_{1-8}$ alkylcarbamoyl, sulfamoyl, cyano, oxo, nitro, or an optionally substituted carbocyclic ring, heterocyclic ring, aryl or heteroaryl as previously described.

Pharmacology and Utility

The compounds of the invention and their pharmaceutically acceptable salts exhibit valuable pharmacological properties when tested in vitro in cell-free kinase assays and in cellular assays, and are therefore useful as pharmaceuticals.

In one aspect, the compounds of the invention may inhibit insulin like growth-factor receptor 1 (IGF-1R), and may be useful in the treatment of IGF-1 R mediated diseases. Examples of IGF-1R mediated diseases include but are not limited to proliferative diseases, such as tumors, for example breast, renal, prostate, colorectal, thyroid, ovarian, pancreas, neuronal, lung, uterine and gastro intestinal tumors, as well as osteosarcomas and melanomas. The efficacy of the compounds of the invention as inhibitors of IGF-1R tyrosine kinase activity may be demonstrated using a cellular capture ELISA. In this assay, the activity of the compounds of the invention against (IGF-1)-induced autophosphorylation of the IGF-1R is determined.

In another aspect, the compounds of the invention may inhibit the tyrosine kinase activity of anaplastic lymphoma kinase (ALK) and the fusion protein of NPM-ALK. This protein tyrosine kinase results from a gene fusion of nucleophosmin (NPM) and ALK, rendering the protein tyrosine kinase activity of ALK ligand independent. NPM-ALK plays a key role in signal transmission in a number of hematopoetic and other human cells leading to hematological and neoplastic diseases, for example in anaplastic large-cell lymphoma (ALCL) and non-Hodgkin's lymphomas (NHL), specifically in ALK+NHL or Alkomas, in inflammatory myofibroblastic tumors (IMT) and neuroblastomas. (Duyster et al. 2001 Oncogene 20, 5623-5637). In addition to NPM-ALK, other gene fusions have been identified in human hematological and neoplastic diseases; for example, TPM3-ALK (a fusion of nonmuscle tropomyosin with ALK).

The inhibition of ALK tyrosine kinase activity may be demonstrated using known methods, for example using the recombinant kinase domain of the ALK in analogy to the VEGF-R kinase assay described in J. Wood et al. Cancer Res. 60, 2178-2189 (2000). In general, in vitro enzyme assays using GST-ALK protein tyrosine kinase are performed in 96-well plates as a filter binding assay in 20 mM Tris HCl, pH=7.5, 3 mM $MgCl_2$, 10 mM $MnCl_2$, 1 mM DTT, 0.1 µCi/assay (=30 µl) [γ-$^{33}$P]-ATP, 2 µM ATP, 3 µg/mL poly (Glu, Tyr 4:1) Poly-EY (Sigma P-0275), 1% DMSO, 25 ng ALK enzyme. Assays are incubated for 10 min at ambient temperature. Reactions are terminated by adding 50 µl of 125 mM EDTA, and the reaction mixture is transferred onto a MAIP Multiscreen plate (Millipore, Bedford, Mass., USA), previously wet with methanol, and rehydrated for 5 min with $H_2O$. Following washing (0.5% $H_3PO_4$), plates are counted in a liquid scintillation counter. $IC_{50}$ values are calculated by linear regression analysis of the percentage inhibition.

The compounds of the invention may potently inhibit the growth of human NPM-ALK overexpressing murine BaF3 cells (DSMZ Deutsche Sammiung von Mikroorganismen and Zellkulturen GmbH, Germany). The expression of NPM-ALK may be achieved by transfecting the BaF3 cell line with an expression vector pClneo™ (Promega Corp., Madison Wis., USA) coding for NPM-ALK and subsequent selection of G418 resistant cells. Non-transfected BaF3 cells depend on IL-3 for cell survival. In contrast, NPM-ALK expressing BaF3 cells (named BaF3-NPM-ALK hereinafter) can proliferate in the absence of IL-3 because they obtain proliferative signal through NPM-ALK kinase. Putative inhibitors of the NPM-ALK kinase therefore abolish the growth signal and may result in antiproliferative activity. The antiproliferative activity of putative inhibitors of the NPM-ALK kinase can however be overcome by addition of IL-3, which provides growth signals through an NPM-ALK independent mechanism. An analogous cell system using FLT3 kinase has also been described (see, E Weisberg et al. Cancer Cell; 1, 433-443 (2002)).

The inhibitory activity of the compounds of the invention may be determined as follows. In general, BaF3-NPM-ALK cells (15,000/microtitre plate well) are transferred to 96-well microtitre plates. Test compounds dissolved in dimethyl sulfoxide (DMSO) are added in a series of concentrations (dilution series) in such a manner that the final concentration of DMSO is not greater than 1% (v/v). After the addition, the plates are incubated for two days during which the control cultures without test compound are able to undergo two cell-division cycles. The growth of the BaF3-NPM-ALK cells is measured by means of YOPRO™ staining [T Idziorek et al. J. Immunol. Methods; 185: 249-258 (1995)]: 25 µl of lysis buffer comprising 20 mM sodium citrate, pH 4.0, 26.8 mM sodium chloride, 0.4% NP40, 20 mM EDTA and 20 mM is added to each well. Cell lysis is completed within 60 min at room temperature and total amount of YOPRO™ bound to DNA is determined by measurement using the Cytofluor II 96-well reader (PerSeptive Biosystems) with the following settings: Excitation (nm) 485/20 and Emission (nm) 530/25.

The compounds of the invention may also be useful in the treatment and/or prevention of acute or chronic inflammatory diseases or disorders or autoimmune diseases e.g. rheumatoid arthritis, osteoarthritis, systemic lupus erythematosus, Hashimoto's thyroiditis, multiple sclerosis, myasthenia gravis, diabetes (type I and II) and the disorders associated therewith, respiratory diseases such as asthma or inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitis, seborrhoeic dermatitis), s inflammatory eye diseases, e.g.

Sjoegren's syndrome, keratoconjunctivitis or uveitis, inflammatory bowel disease, Crohn's disease or ulcerative colitis.

In accordance with the foregoing, the present invention provides:

(1) a compound of the invention for use as a pharmaceutical;
(2) a compound of the invention for use as an IGF-1R inhibitor, for example for use in any of the particular indications hereinbefore set forth;
(3) a pharmaceutical composition, e.g. for use in any of the indications herein before set forth, comprising a compound of the invention as active ingredient together with one or more pharmaceutically acceptable diluents or carriers;
(4) a method for the treatment of any particular indication set forth hereinbefore in a subject in need thereof which comprises administering an effective amount of a compound of the invention or a pharmaceutical composition comprising same;
(5) the use of a compound of the invention for the manufacture of a medicament for the treatment or prevention of a disease or condition in which IGF-1R activation plays a role or is implicated;
(6) the method as defined above under (4) comprising co-administration, e.g. concomitantly or in sequence, of a therapeutically effective amount of a compound of the invention and one or more further drug substances, said further drug substance being useful in any of the particular indications set forth hereinbefore;
(7) a combination comprising a therapeutically effective amount of a compound of the invention and one or more further drug substances, said further drug substance being useful in any of the particular indications set forth hereinbefore;
(8) use of a compound of the invention for the manufacture of a medicament for the treatment or prevention of a disease which responds to inhibition of the anaplastic lymphoma kinase;
(9) the use according to (8), wherein the disease to be treated is selected from anaplastic large cell lymphoma, non-Hodgkin's lymphomas, inflammatory myofibroblastic tumors, neuroblastomas and neoplastic diseases;
(10) the use according to (8) or (9), wherein the compound is of Formula (1), (2), (3), (4) or (5), or any one of the examples, or a pharmaceutically acceptable salt thereof;
(11) a method for the treatment of a disease which responds to inhibition of the anaplastic lymphoma kinase, especially a disease selected from anaplastic large-cell lymphoma, non Hodgkin's lymphomas, inflammatory myofibroblastic tumors, neuroblastomas and neoplastic diseases, comprising administering an effective amount of a compound of the invention or a pharmaceutically acceptable salt thereof.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.01 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 100 mg, conveniently administered, for example, in divided doses up to four times a day or in retard form. Suitable unit dosage forms for oral administration comprise from ca. 1 to 50 mg active ingredient.

Compounds of the invention may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present invention in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the invention in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length $C_8$ to $C_{12}$ from Hills AG, Germany), and vegetable oils such as cottenseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The compounds of the invention may be administered as the sole active ingredient, or together with other drugs useful against neoplastic diseases or useful in immunomodulating regimens. For example, the compounds of the invention may be used in accordance with the invention in combination with pharmaceutical compositions effective in various diseases as described above, e.g. with cyclophosphamide, 5-fluorouracil, fludarabine, gemcitabine, cisplatinum, carboplatin, vincristine, vinblastine, etoposide, irinotecan, paclitaxel, docetaxel, rituxan, doxorubicine, gefitinib, or imatinib; or also with cyclosporins, rapamycins, ascomycins or their immunosuppressive analogs, e.g. cyclosporin A, cyclosporin G, FK-506, sirolimus or everolimus, corticosteroids, e.g. prednisone, cyclophosphamide, azathioprene, methotrexate, gold salts, sulfasalazine, antimalarials, brequinar, leflunomide, mizoribine, mycophenolic acid, mycophenolate, mofetil, 15-deoxyspergualine, immuno-suppressive monoclonal antibodies, e.g. monoclonal antibodies to leukocyte receptors, e.g. MHC, CD2, CD3, CD4, CD7, CD25, CD28, I CD40, CD45, CD58, CD80, CD86, CD152, CD137, CD154, ICOS, LFA-1, VLA-4 or their ligands, or other immunomodulatory compounds, e.g. CTLA41g.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

Processes for Making Compounds of the Invention

General procedures for preparing compounds of the invention are described in the Examples, infra. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry", John Wiley and Sons, 1991).

The compounds of the invention, including their salts, are also obtainable in the form of hydrates, or their crystals may include for example the solvent used for crystallization (present as solvates). Salts can usually be converted to compounds in free form, e.g., by treating with suitable basic agents, for example with alkali metal carbonates, alkali metal hydrogen carbonates, or alkali metal hydroxides, such as potassium carbonate or sodium hydroxide. A compound of the invention in a base addition salt form may be converted to the corresponding free acid by treating with a suitable acid (e.g., hydrochloric acid, etc.). In view of the close relationship between the novel compounds in free form and those in the form of their salts, including those salts that may be used as intermediates, for example in the purification or identification of the novel compounds, any reference to the free compounds is to be understood as referring also to the corresponding salts, as appropriate.

Salts of the inventive compounds with a salt-forming group may be prepared in a manner known per se. Acid addition salts of compounds of Formula (1), (2A), (2B), (3A) and (3B), may thus be obtained by treatment with an acid or with a suitable anion exchange reagent. Pharmaceutically acceptable salts of the compounds of the invention may be formed, for example, as acid addition salts, with organic or inorganic acids, from compounds of Formula (1), (2A), (2B), (3A) and (3B), with a basic nitrogen atom.

Suitable inorganic acids include, but are not limited to, halogen acids, such as hydrochloric acid, sulfuric acid, or phosphoric acid. Suitable organic acids include, but are not limited to, carboxylic, phosphoric, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, -malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4 aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4 methylbenzenesulfonic acid, methylsulfuric acid, ethylsulfuric acid, dodecylsulfuric acid, N cyclohexylsulfamic acid, N-methyl-, N-ethyl- or N-propyl-sulfamic acid, or other organic protonic acids, such as ascorbic acid. For isolation or purification purposes, it is also possible to use pharmaceutically unacceptable salts, for example picrates or perchlorates. For therapeutic use, only pharmaceutically acceptable salts or free compounds are employed (where applicable in the form of pharmaceutical preparations).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention may be prepared by methods known to those of ordinary skill in the art (e.g., for further details see Saulnier et al., (1994), Bioorganic and Medicinal Chemistry Letters, Vol. 4, p. 1985). For example, appropriate prodrugs may be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention may be made by means known to those of ordinary skill in the art. A detailed description of techniques applicable to the creation of protecting groups and their removal may be found in T. W. Greene, "Protecting Groups in Organic Chemistry", 3$^{rd}$ edition, John Wiley and Sons, Inc., 1999.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubilities, reactivity, etc.) and may be readily separated by taking advantage of these dissimilarities. The diastereomers may be separated by fractionated crystallization, chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture may be found in Jean Jacques, Andre Collet, Samuel H. Wilen, "Enantiomers, Racemates and Resolutions", John Wiley And Sons, Inc., 1981.

In summary, the compounds of the invention may be made by a process as described in the Examples; and (a) optionally converting a compound of the invention into a pharmaceutically acceptable salt;

(b) optionally converting a salt form of a compound of the invention to a non-salt form;

(c) optionally converting an unoxidized form of a compound of the invention into a pharmaceutically acceptable N-oxide;

(d) optionally converting an N-oxide form of a compound of the invention to its unoxidized form;

(e) optionally resolving an individual isomer of a compound of the invention from a mixture of isomers;

(f) optionally converting a non-derivatized compound of the invention into a pharmaceutically acceptable prodrug derivative; and (g) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter. One of skill in the art will appreciate that the above transformations are only representative of methods for preparation of the compounds of the present invention, and that other well known methods can similarly be used. The present invention is further exemplified, but not limited, by the following and Examples that illustrate the preparation of the compounds of the invention.

Intermediate 1

2,5-dichloro-N-(5-methyl-1H-pyrazol-3-yl)pyrimidin-4-amine

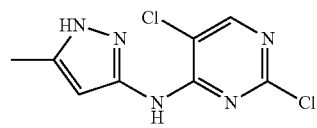

A mixture of 5-methyl-1H-pyrazol-3-amine (3.00 g, 30.9 mmol), 2,4,5-trichloropyrimidine (5.67 g, 30.9 mmol, 1 equiv.) and Na$_2$CO$_3$ (3.60 g, 34.0 mmol, 1.1 equiv.) in EtOH (100 mL) was heated at 40° C. for 24 h. The solvent was removed in vacuo. The resulting residue was partitioned between EtOAc (350 mL) and water (100 mL). The EtOAc layer was washed with water (3×), saturated aqueous NaCl (1×) and dried over Na$_2$SO$_4$. The resulting EtOAc solution was concentrated in vacuo, providing the product 2,5-dichloro-N-(5-methyl-1H-pyrazol-3-yl)pyrimidin-4-amine; ESMS m/z 244.0 (M+H$^+$).

Intermediate 2

2-chloro-N-(5-methyl-1H-pyrazol-3-yl)-5-(trifluoromethyl)pyrimidin-4-amine

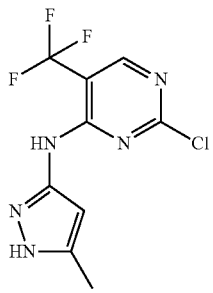 [SMILES: Cc1cc(Nc2nc(Cl)ncc2C(F)(F)F)n[nH]1]

A mixture of 2,4-dichloro-5-(trifluoromethyl)pyrimidine (1.06 g, 4.86 mmol), 5-methyl-1H-pyrazol-3-amine (472.2 mg, 4.86 mmol) and sodium carbonate (2.06 g, 19.4 mmol) in 100 mL of EtOH was stirred at room temperature overnight. The reaction mixture was concentrated in vacuo. The crude solid was partitioned between EtOAc and water. The combined organic extracts were dried ($Na_2SO_4$), concentrated in vacuo, and purified by silica chromatography (EtOAc/hexanes: 1/1) to afford 2-chloro-N-(5-methyl-1H-pyrazol-3-yl)-5-(trifluoromethyl)pyrimidin-4-amine; ESMS m/z 278.0 (M+H$^+$).

Intermediate 3

2,5-dimethyl-4-(3-methylisoxazol-5-yl)aniline

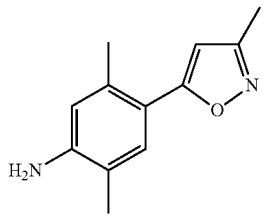

Step 1: 1-(2,5-dimethyl-4-nitrophenyl)ethanone

To a mixture of 1-Bromo-2,5-dimethyl-4-nitrobenzene (1 g, 4.34 mmol) and tributyl(1-ethoxyvinyl)tin (1.88 g, 5.2 mmol) in DMF (20 mL), was added tetrakis(triphenylphosphine) palladium (0) (250 mg, 5% mmol). The reaction tube was sealed, the mixture was purged with $N_2$ for 3 min and then heated at 90° C. under $N_2$ for overnight. The reaction was cooled to room temperature and poured into aqueous HCl (1N, 100 mL). The mixture was stirred for 1 hour, and then extracted with ethyl acetate (3×100 mL). The organic extracts were combined, washed with brine and concentrated. The crude product was purified with silica gel chromatography (20% ethyl acetate in hexanes) to afford 1-(2,5-dimethyl-4-nitrophenyl)ethanone as a yellow solid.

Step 2: 1-(2,5-dimethyl-4-nitrophenyl)-3-(dimethylamino)but-2-en-1-one

A mixture of 1-(2,5-dimethyl-4-nitrophenyl)ethanone (Step 1, 300 mg, 1.55 mmol) and 1,1-dimethoxy-N,N-dimethylethanamine (1 mL) was heated in a microwave at 130° C. for 10 min. The crude product was purified with silica gel chromatography (60% ethyl acetate in hexanes) to afford 1-(2,5-dimethyl-4-nitrophenyl)-3-(dimethylamino)but-2-en-1-one as a yellow solid.

Steps 3 and 4: 2,5-dimethyl-4-(3-methylisoxazol-5-yl)aniline

A mixture of 1-(2,5-dimethyl-4-nitrophenyl)-3-(dimethylamino)but-2-en-1-one (Step 2, 100 mg, 0.38 mmol) and hydroxylamine monohydrochloride (132 mg, 1.9 mmol) in ethanol (3 mL) was heated in a microwave at 100° C. for 15 min. The obtained 5-(2,5-dimethyl-4-nitrophenyl)-3-methylisoxazole was dissolved in methanol (10 mL). To this solution was added Pd/C (10%). The reaction mixture was degassed and purged with $H_2$ for several times and stirred under $H_2$ (1 atm.) overnight. The mixture was filtered and concentrated to afford 2,5-dimethyl-4-(3-methylisoxazol-5-yl)aniline. ESMS m/z 203 (M+H$^+$).

Intermediate 4

2,5-dimethyl-4-(oxazol-5-yl)aniline

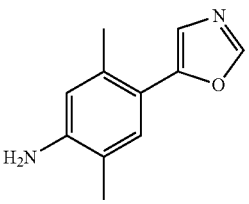

Step 1: To a mixture of 2,5-dimethyl-4-nitrobenzaldehyde (75 mg, 0.42 mmol) and toluenesulfonylmethyl isocyanide (TOSMIC) (98 mg, 0.5 mmol) in methanol (2 mL), was added sodium methoxide (68 mg, 1.26 mmol). The mixture was sealed and heated at 90° C. for 15 hr. The reaction mixture was concentrated and partitioned between water and ethyl acetate. The organic layer was separated, dried over sodium sulfate and concentrated. The 5-(2,5-Dimethyl-4-nitrophenyl)oxazole obtained was used in the next step without purification.

Step 2: The 5-(2,5-dimethyl-4-nitrophenyl)oxazole obtained in the last step was dissolved in methanol (10 mL). To the solution was added Pd/C (10%). The reaction mixture was degassed and purged with $H_2$ for several times and then stirred under 1 atm. hydrogen gas overnight. The mixture was filtered and concentrated to afford 2,5-dimethyl-4-(oxazol-5-yl)aniline as a white solid. ESMS m/z 189 (M+H$^+$).

Intermediate 5

2,5-Dimethyl-4-(3-methyl-1H-pyrazol-5-yl)aniline

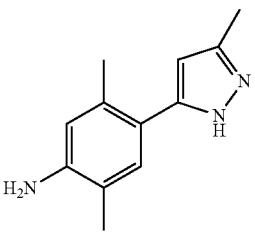

A mixture of 1-(2,5-dimethyl-4-nitrophenyl)-3-(dimethylamino)but-2-en-1-one (100 mg, 0.38 mmol) and hydrazine (60 uL, 1.9 mmol) in ethanol (3 mL) was heated in a microwave at 100° C. for 15 min. The obtained 5-(2,5-dimethyl-4-nitrophenyl)-3-methylpyrazol was dissolved in methanol (10 mL). To the solution was added Pd/C (10%). The reaction mixture was degassed and purged with H$_2$ for several times and stirred under 1 atm. hydrogen gas overnight. The mixture was filtered and concentrated to afford 2,5-Dimethyl-4-(3-methyl-1H-pyrazol-5-yl)aniline. ESMS m/z 202 (M+H$^+$).

Intermediate 6

2,5-Dimethyl-4-(2-methylthiazol-4-yl)aniline

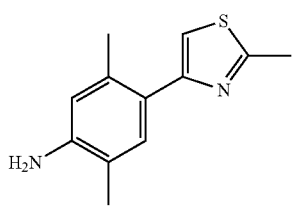

Step 1: To a mixture of 1-(2,5-dimethyl-4-nitrophenyl)ethanone (300 mg, 1.55 mmol) in HBr (48%) (5 mL)/methanol (2.4 mL) was added bromine (250 mg, 1.55 mmol). The mixture was stirred at room temperature for 4 hrs. The mixture was diluted with water and extracted with ethyl acetate (2×20 mL). The organic layer was washed with brine and concentrated. The residue was purified with silica gel column chromatography (10% ethyl acetate in hexanes) to afford 2-bromo-1-(2,5-dimethyl-4-nitrophenyl)ethanone as a white solid.

Step 2: A mixture of 2-bromo-1-(2,5-dimethyl-4-nitrophenyl)ethanone (70 mg, 0.26 mmol) and ethanethioamide (30 mg, 0.4 mmol) in ethanol (2 mL) was heated in a microwave at 150° C. for 20 min. The obtained 4-(2,5-dimethyl-4-nitrophenyl)-2-methylthiazole was dissolved in methanol (10 mL). To the solution was added Pd/C (10%). The reaction mixture was degassed and purged with H$_2$ for several times and stirred under 1 atm. hydrogen gas overnight. The mixture was filtered and concentrated to afford 2,5-dimethyl-4-(2-methylthiazol-4-yl)aniline. ESMS m/z 219 (M+H+).

Intermediate 7

2,5-Dimethyl-4-(1-methyl-1H-imidazol-2-yl)aniline

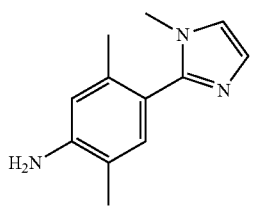

To a solution of 2-(2,5-dimethyl-4-nitrophenyl)-1H-imidazole (50 mg, 0.23 mmol) in DMF (2 mL) was added NaH (11 mg, 0.46 mmol) at 0° C. After stirring for 15 min, iodomethane (65 mg, 0.46 mmol) was added dropwise. The mixture was stirred at 0° C. for 1 hr, and quenched by adding saturated ammonium chloride aqueous solution. The mixture was extracted with ethyl acetate (3×15 mL). The organic layer was washed with brine and dried over sodium sulfate. After concentration, the residue was dissolved in methanol (10 mL). To the solution was added Pd/C (10%). The reaction mixture was degassed and purged with H$_2$ for several times and stirred under 1 atm. hydrogen gas overnight. The mixture was filtered and concentrated to afford 2,5-dimethyl-4-(1-methyl-1H-imidazol-2-yl)aniline. ESMS m/z 202 (M+H$^+$).

Intermediate 8

2,5-dimethyl-4-(pyridin-3-yl)aniline

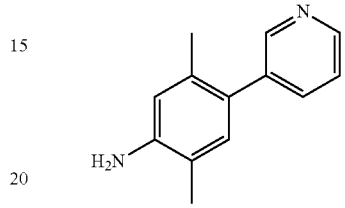

A suspension of 4-bromo-2,5-dimethylaniline (4.00 g, 20 mmol), pyridin-3-ylboronic acid (2.70 g, 11 mmol), Pd$_2$(dba)$_3$ (0.55 g, 0.6 mmol), 2-dicyclohexylphosphino-2',6'-dimethoxybiphenyl (0.98 g, 1.2 mmol) and Na$_2$CO$_3$ (10.6 g, 100 mmol) in n-BuOH (50 mL) was degassed by a stream of argon gas for 15 min. The reaction flask was sealed and placed in a pre-heated oil bath (115° C.). After stirring overnight, the reaction was cooled and filtered. The filter cake was washed with DCM and the filtrate was concentrated in vacuo. The resulting residue was dissolved in EtOAc (150 mL). EtOAC is sequentially washed with water (20 mL), brine (20 mL), dried over Na$_2$SO$_4$ and evaporated. The crude product was purified by silica chromatography (0-50% EtOAC in hexanes gradient) to give 2,5-dimethyl-4-(pyridin-3-yl)aniline as a yellow solid; ESMS m/z 199.1 (M+H$^+$).

Intermediate 9

8-(2,5-dimethyl-4-nitrophenyl)-1,4-dixoaspiro[4.5]dec-7-ene

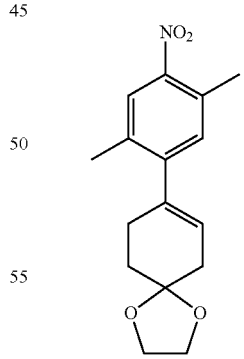

A mixture of 4,4,4,4-tetramethyl-2-(1,4-dioxaspiro[4.5]dec-7-en-8-yl)-1,3,2-dixoaborolane (200 mg, 0.86 mmol), 1-bromo-2,5-dimethyl-4-nitrobenzene (228 mg, 0.86 mmol), tetrakis(triphenylphosphine)palladium(0) (98 mg, 0.09 mmol), and cesium fluoride (392 mg, 2.58 mmol) in a mixture of 1,2-dimethoxyethane (2 mL) and methanol (1 mL) was degassed for 5 min, and then heated at 130° C. in a microwave reactor for 15 min. The reaction was concentrated in vacuo, and purified by silica chromatography (EtOAC/hexanes:3/7) to afford 8-(2,5-dimethyl-4-nitrophenyl)-1,4-dixoaspiro[4.5]dec-7-ene; ESMS m/z 290.2 (M+H$^+$).

Intermediate 10

2,5-dimethyl-4-(1,4-dioxaspiro[4.5]decan-8-yl)aniline

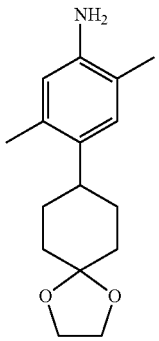

A mixture of 8-(2,5-dimethyl-4-nitrophenyl)-1,4-dioxaspiro[4.5]decane (130.2 mg, 0.45 mmol) and 10% Pd—C (13.0 mg) in MeOH (20 mL) was degassed and then reacted under 1 atm. H$_2$. Upon reaction completion, the Pd—C was removed by filtration and the filtrate was concentrated in vacuo to afford 2,5-dimethyl-4-(1,4-dioxaspiro[4.5]decan-8-yl)aniline; ESMS m/z 262.2 (M+H$^+$).

Intermediate 11

2-fluoro-5-methyl-4-(1,4-dioxaspiro[4.5]dec-7-en-8-yl)aniline

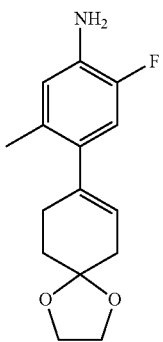 [SMILES: Cc1cc(N)c(F)cc1C1=CCC2(CC1)OCCO2]

A mixture of 4,4,4,4-tetramethyl-2-(1,4-dioxaspiro[4.5]dec-7-en-8-yl)-1,3,2-dioxaborolane (532.0 mg, 2.0 mmol), 4-bromo-2-fluoro-5-methylaniline (406.0 mg, 2.0 mmol), tetrakis(triphenylphosphine)palladium(0) (231.1 mg, 0.2 mmol), cesium fluoride (912.0 mg, 6.0 mmol), 1,2-dimethoxyethane (4 mL) and methanol (2 mL) was degassed for 5 min and then heated at 130° C. in a microwave reactor for 15 min. The reaction was concentrated in vacuo, and purified by silica chromatography (EtOAC/Hexanes:3/7) to afford 2-fluoro-5-methyl-4-(1,4-dioxaspiro[4.5]dec-7-en-8-yl)aniline; ESMS m/z 264.1 (M+H$^+$).

Intermediate 12

2-fluoro-5-dimethyl-4-(1,4-dioxaspiro[4.5]decan-8-yl)aniline

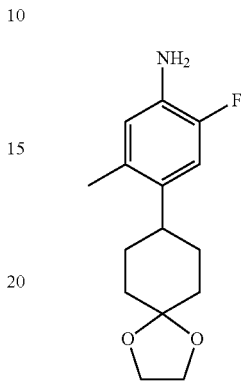

A mixture of 2-fluoro-5-methyl-4-(1,4-dioxaspiro[4.5]dec-7-en-8-yl)aniline (130 mg, 0.50 mmol) and 10% Pd—C (13.0 mg) in MeOH (20 mL) was degassed and then reacted under 1 atm. H$_2$. Upon reaction completion, the Pd—C was removed by filtration and the filtrate was concentrated in vacuo to afford 2-fluoro-5-dimethyl-4-(1,4-dioxaspiro[4.5]decan-8-yl)aniline; ESMS m/z 266.2 (M+H$^+$).

Intermediate 13

4-(5-fluoro-2-methyl-4-(4-(5-methyl-1H-pyrazol-3-ylamino)-5-(trifluoromethyl)pyrimidin-2-ylamino)phenyl)cyclohexanone

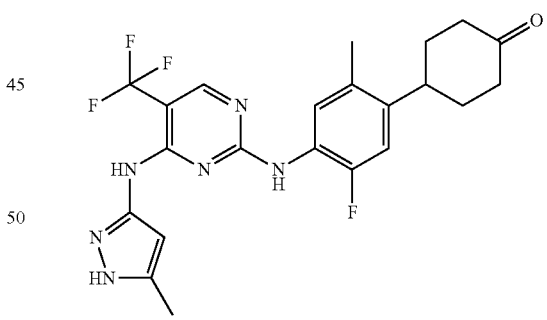

A mixture of 2-fluoro-5-methyl-4-(1,4-dioxaspiro[4.5]decan-8-yl)aniline (318.6 mg, 1.2 mmol), 2-chloro-N-(5-methyl-1H-pyrazol-3-yl)-5-(trifluoromethyl)pyrimidin-4-amine (333.0 mg, 1.2 mmol) and HCl (4 N in water, 0.3 mL, 1.2 mmol) in i-PrOH (4.0 mL) was heated at 125° C. in an oil bath overnight. The reaction mixture was concentrated in vacuo. The resulting crude mixture was dissolved in THF (4 mL), MeOH (2 mL) and HCl (4N in water, 0.3 mL, 1.2 mmol), and stirred at room temperature for an additional 2 h. The reaction mixture was concentrated in vacuo, and purified by silica chromatography (0-100% EtOAC in hexanes gradient) to afford 4-(5-fluoro-2-methyl-4-(4-(5-methyl-1H-pyrazol-3-ylamino)-5-(trifluoromethyl)pyrimidin-2-ylamino) phenyl)cyclohexanone; ESMS m/z 463.2 (M+H$^+$).

Intermediate 14

N-(2,5-dichloropyrimidin-4-yl)-5-methylisoxazol-3-amine

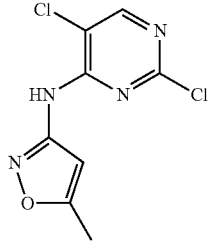

The mixture 5-methylisoxazol-3-amine (98 mg, 1.0 mmol), 2,4,5-trichloropyrimidine (344 µL, 3.0 mmol), and sodium carbonate (106 mg, 1.0 mmol) in 3 mL of EtOH was heated at 60° C. over night. The reaction mixture was concentrated and then partitioned between EtOAc and brine. The collected organic extracts were dried (Na$_2$SO$_4$), concentrated in vacuo, and purified with silica gel chromatography (MeOH/DCM: 1/9) to afford N-(2,5-dichloropyrimidin-4-yl)-5-methylisoxazol-3-amine; ESMS m/z 245.0 (M+H$^+$).

Intermediate 15

2,5-dichloro-N-(5-cyclopropyl-1H-pyrazol-3-yl) pyrimidin-4-amine

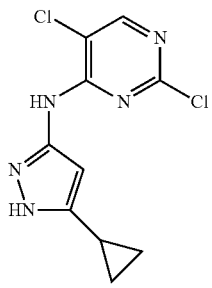 [SMILES: Clc1ncc(Cl)c(Nc2cc(C3CC3)[nH]n2)n1]

A mixture of 5-cyclopropyl-1H-pyrazol-3-amine (246 mg, 2.00 mmol), 2,4,5-trichloropyrimidine (367 mg, 2.00 mmol, 1 equiv.) and Na$_2$CO$_3$ (233 mg, 2.20 mmol, 1.1 equiv.) in EtOH (10 mL) was heated at 40° C. for 16 h. The crude reaction mixture was diluted with EtOAc and sequentially washed with: water (3×) and saturated aqueous NaCl (1×). The resulting EtOAc layer was dried over Na$_2$SO$_4$ and then concentrated in vacuo, providing 2,5-dichloro-N-(5-cyclopropyl-1H-pyrazol-3-yl)pyrimidin-4-amine; ESMS m/z 270.0 (M+H$^+$).

Intermediate 16 tert-Butyl 4-(6-amino-5-fluoro-1-oxoisoindolin-2-yl) piperidine-1-carboxylate

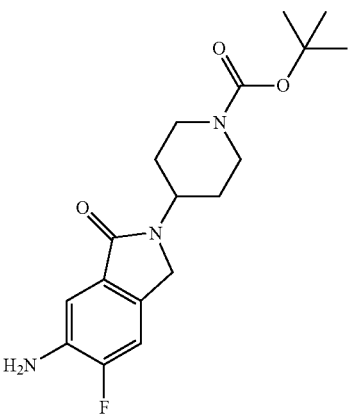 [SMILES: CC(C)(C)OC(=O)N1CCC(N2Cc3cc(F)c(N)cc3C2=O)CC1]

Step 1: tert-Butyl 4-(2-chloro-4-fluoro-5-nitrobenzamido)piperidine-1-carboxylate Under N$_2$, to the solution of 2-chloro-4-fluoro-5-nitro-benzoic acid (1.0 g, 4.56 mmol in 40 mL of DCM at 0° C. are added thionyl chloride (1.0 mL, 13.68 mmol) and 0.1 mL of DMF sequentially. The reaction mixture was warmed gradually to room temperature and stirred overnight. The reaction mixture was concentrated in vacuo to afford 2-chloro-4-fluoro-5-nitrobenzoyl chloride. The crude was dissolved in 40 mL of DCM, and 1-boc-4-aminopiperidine (910 mg, 4.56 mmol) and triethylamine (1.29 mL, 9.12 mmol) were added to the solution sequentially. After stirring at room temperature 1 h, the reaction mixture was washed with 20 mL of water. The organic extract was dried (Na$_2$SO$_4$), followed by concentration in vacuo to afford tert-Butyl 4-(2-chloro-4-fluoro-5-nitrobenzamido)piperidine-1-carboxylate; ESMS m/z 402.1 (M+H$^+$).

Step 2: tert-Butyl 4-(4-fluoro-5-nitro-2-vinylbenzamido)piperidine-1-carboxylate Under nitrogen, the mixture of tert-butyl 4-(2-chloro-4-fluoro-5-nitrobenzamido)piperidine-1-carboxylate (Step 1, 1.52 g, 3.88 mmol), vinylboronic acid dibutyl ester (0.86 mL, 3.88 mmol), dichlorobis(triphenylphosphine)palladium (II) (136 mg, 0.2 mmol) and sodium carbonate (2.9 g, 27.2 mmol) in THF (40 mL) and water (10 mL) was heated at 90° C. overnight. The reaction mixture was cooled to room temperature, partitioned between EtOAc and brine. The organic extracts were dried (Na$_2$SO$_4$), concentrated, and purified by silica gel chromatography (EtOAc/Hexanes:1/4) to afford tert-Butyl 4-(4-fluoro-5-nitro-2-vinylbenzamido)piperidine-1-carboxylate; ESMS m/z 394.2 (M+H$^+$).

Step 3: tert-Butyl 4-(5-fluoro-6-nitro-1-oxoisoindolin-2-yl)piperidine-1-carboxylate tert-Butyl 4-(4-fluoro-5-nitro-2-vinylbenzamido)piperidine-1-carboxylate (Step 2, 1.1 g, 2.77 mmol) in 50 mL of DCM is chilled to −78° C. Ozone was passed through the solution until the starting material was consumed, and then nitrogen was passed through the solution for 5 min. The reaction mixture was warmed to room temperature. Triphenylphosphine-resin (2.77 g) in 10 mL of DCM was added, and was stirred for another 1.5 h. The resin was filtered off, and the solution was concentrated in vacuo. The resulting crude was dissolved in DCM (15 mL), and to this solution were added TFA (15 mL) and triethylsilane (1.0 mL, 5.9 mmol) sequentially. The reaction was stirred at room temperature 2 h. After concentration, the reaction crude was poured into 10 mL of water, neutralized to pH 8 with sat. aq. NaHCO$_3$, followed by addition of (Boc)$_2$O (603 mg, 2.77 mmol) in 10 mL of DCM. The reaction was stirred at room temperature for 1.5 h, then extracted with DCM. The organic extracts were dried (Na$_2$SO$_4$), concentrated in vacuo, and purified by silica gel chromatography (EtOAc/Hexanes:1/4) to give tert-Butyl 4-(5-fluoro-6-nitro-1-oxoisoindolin-2-yl)piperidine-1-carboxylate; ESMS m/z 380.2 (M+H$^+$).

Step 4: tert-Butyl 4-(6-amino-5-fluoro-1-oxoisoindolin-2-yl)piperidine-1-carboxylate The mixture of tert-butyl 4-(5-fluoro-6-nitro-1-oxoisoindolin-2-yl)piperidine-1-carboxylate (Step 3, 240 mg, 0.72 mmol), Pd (10% wt on active carbon, 24 mg) and MeOH (20 mL) was evacuated to remove air, and then the reaction was stirred under a hydrogen balloon until the starting material is consumed. Pd/C was filtered off and the solution was concentrated in vacuo to afford tert-Butyl 4-(6-amino-5-fluoro-1-oxoisoindolin-2-yl)piperidine-1-carboxylate; ESMS m/z 350.2 (M+H$^+$).

Intermediate 17 tert-butyl-4-(4-aminonaphthalen-1-yl)piperidine-1-carboxylate

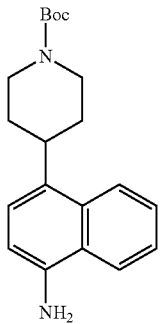 [SMILES: CC(C)(C)OC(=O)N1CCC(c2ccc(N)c3ccccc23)CC1]

Step 1: tert-butyl-4-(4-aminonaphthalen-1-yl)-5,6-dihydropyridine-1(2H)-carboxylate A mixture of 4-bromonaphthalen-1-amine (1.0 g, 4.5 mmol), tert-butyl-4-(4,4,5,5-tetramethyl-1,3,2-dioxaborolan-2-yl)-5,6-dihydropyridine-1(2H)-carboxylate (1.7 g, 5.4 mmol), Pd(PPh$_3$)$_4$ (26.01 mg, 0.02 mmol) and Na$_2$CO$_3$ (3.34 g, 31.5 mmol) in 10 mL of DMF and 5 mL of water was degassed and purged with nitrogen. The reaction was heated at 100° C. for 5 h, and cooled to room temperature. The reaction mixture was partitioned between EtOAc and water. The combined organic extracts were dried (Na$_2$SO$_4$), concentrated in vacuo and purified by silica gel chromatography (MeOH/DCM: 5/95) to afford tert-butyl-4-(4-aminonaphthalen-1-yl)-5,6-dihydropyridine-1(2H)-carboxylate.

Step 2: tert-butyl-4-(4-aminonaphthalen-1-yl)piperidine-1-carboxylate

To a solution of tert-butyl-4-(4-aminonaphthalen-1-yl)-5,6-dihydropyridine-1(2H)-carboxylate in 50 mL of MeOH was added 10 wt % Pd—C (100 mg). The reaction was degassed to remove air and stirred under 1 atm. H$_2$ until the starting material is consumed. The Pd—C was removed by filtration and the resulting solution was concentrated in vacuo to afford tert-butyl-4-(4-aminonaphthalen-1-yl)piperidine-1-carboxylate.

Intermediate 18

3-ethyl-2,3,4,5-tetrahydro-1H-benzo[d]azepin-7-amine

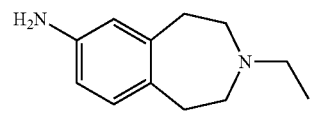

3-ethyl-2,3,4,5-tetrahydro-1H-benzo[d]azepin-7-amine was synthesized by the method described in the literature reference: Pecherer, B. et al. *J. Heterocyclic Chem* 1971, 8(5), 779-783, in conjunction with standard synthetic methodology.

EXAMPLE 1

1-(4-(5-chloro-4-(5-methyl-1H-pyrazol-3-ylamino)pyrimidin-2-ylamino)-2,5-dimethylphenyl)ethanone O-2-hydroxyethyloxime (28)

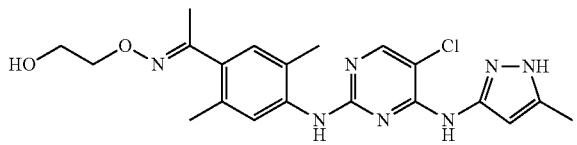 [SMILES: C/C(=N\OCCO)c1cc(C)c(Nc2ncc(Cl)c(Nc3cc(C)[nH]n3)n2)cc1C]

Step 1: To a solution of N$^2$-(4-bromo-2,5-dimethylphenyl)-5-chloro-N$^4$-(5-methyl-1H-pyrazol-3-yl)pyrimidine-2,4-diamine (280 mg, 0.69 mmol) in THF (3 mL) was added p-TSA (119 mg, 0.69 mmol) and 3,4-dihydro-2H-pyran (348 mg, 2.86 mmol). The mixture was stirred at room temperature for 14 h and then poured into saturated aqueous NaHCO$_3$ solution (10 mL). The resulting mixture was extracted with EtOAc (3×10 mL) and the combined organic layers were concentrated. The resulting residue was purified by flash column chromatography (silica gel, 0-50% EtOAc in hexanes gradient) to provide N$^2$-(4-bromo-2,5-dimethylphenyl)-5-chloro-N$^4$-(5-methyl-1-(tetrahydro-2H-pyran-2-yl)-1H-pyrazol-3-yl)pyrimidine-2,4-diamine as a white solid; ESMS m/z 491.1 (M+H$^+$).

Step 2: A mixture of N$^2$-(4-bromo-2,5-dimethylphenyl)-5-chloro-N$^4$-(5-methyl-1-(tetrahydro-2H-pyran-2-yl)-1H-pyrazol-3-yl)pyrimidine-2,4-diamine (166 mg, 0.34 mmol), tributyl(1-ethoxyvinyl)stannane (146 mg, 0.41 mmol) and Pd(PPh$_3$)$_4$ (39 mg, 0.034 mmol) in toluene (2 mL) was degassed and heated at 100° C. under N$_2$ for 14 h. After cooling down to room temperature, the mixture was concentrated. The resulting residue was redissolved in acetonitrile (2 mL) and treated with 1N HCl (2 mL) for 14 h. After extraction with EtOAc (3×15 mL), the combined organic layers were treated with saturated aqueous KF (10 mL). The resulted organic layer was collected and treated with brine and dried over MgSO$_4$. After removing the drying agent by filtration, the filtrate was concentrated and purified by flash column chromatography (silica gel, 0-100% EtOAc in hexanes gradient) to provide 1-(4-(5-chloro-4-(5-methyl-1H-pyrazol-3-ylamino)pyrimidin-2-ylamino)-2,5-dimethylphenyl)ethanone as a white solid; ESMS m/z 371.1 (M+H$^+$).

Step 3: To a solution of 1-(4-(5-chloro-4-(5-methyl-1H-pyrazol-3-ylamino)pyrimidin-2-ylamino)-2,5-dimethylphenyl)ethanone (60 mg, 0.16 mmol) in MeOH (1 mL) was added AcOH (15 mg, 0.25 mmol), followed by the addition of 2-(aminooxy)ethanol (20 mg, 0.26 mmol). The mixture was heated to 60° C. for 14 h and cooled down to room temperature. The mixture was then purified directly by preparative RP-HPLC to provide 1-(4-(5-chloro-4-(5-methyl-1H-pyrazol-3-ylamino)pyrimidin-2-ylamino)-2,5-dimethylphenyl)ethanone O-2-hydroxyethyl oxime; ESMS m/z 430.2 (M+H$^+$).

EXAMPLE 2

4-(5-chloro-4-(5-methyl-1H-pyrazol-3-ylamino)pyrimidin-2-ylamino)-N-(2-(dimethylamino)ethyl)-2,5-dimethylbenzamide (31)

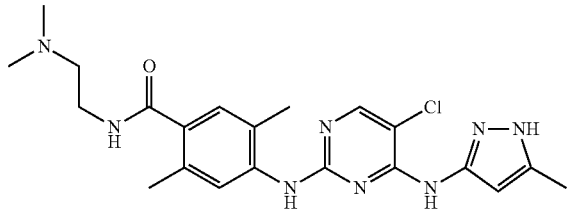

To a solution of 4-(5-chloro-4-(5-methyl-1-(tetrahydro-2H-pyran-2-yl)-1H-pyrazol-3-ylamino)pyrimidin-2-ylamino)-2,5-dimethylbenzoic acid (35.0 mg, 0.077 mmol) in DMF (0.5 mL) was added HATU (29.1 mg, 0.077 mmol), DIEA (26.7 µL, 0.153 mmol) and N$^1$,N$^1$-dimethylethane-1,2-diamine (25.2 µL, 0.230 mmol). The reaction mixture was stirred at room temperature overnight. 1N HCl aqueous solution (0.5 mL) was then added and the reaction mixture was heated at 100° C. for 1.5 hours to remove the tetrahydro-2H-pyran-2-yl protecting group. The mixture was purified by preparative RP-HPLC to provide 4-(5-chloro-4-(5-methyl-1H-pyrazol-3-ylamino)pyrimidin-2-ylamino)-N-(2-(dimethylamino)ethyl)-2,5-dimethylbenzamide; ESMS m/z 443.2 (M+H$^+$).

EXAMPLE 3

4-(4-(5-chloro-4-(5-methyl-1H-pyrazol-3-ylamino)pyrimidin-2-ylamino)-2,5-dimethylphenyl)cyclohexanone oxime (33)

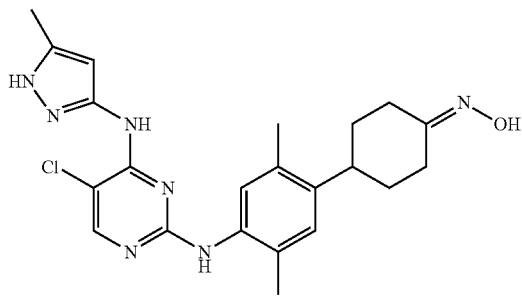 [SMILES: Cc1cc(Nc2nc(Nc3cc(C)c(C4CCC(=NO)CC4)cc3C)ncc2Cl)n[nH]1]

To a solution of 4-(4-(5-chloro-4-(5-methyl-1H-pyrazol-3-ylamino)pyrimidin-2-ylamino)-2,5-dimethylphenyl)cyclohexanone (15 mg, 0.033 mmol) in MeOH (0.5 mL) was added NaOAc (6 mg, 0.073 mmol) and NH$_2$OH HCl (5 mg, 0.073 mmol). The resulting mixture was stirred at 70° C. for 2 h. and then cooled down to room temperature. The mixture was purified directly by preparative RP-HPLC to provide 4-(4-(5-chloro-4-(5-methyl-1H-pyrazol-3-ylamino)pyrimidin-2-ylamino)-2,5-dimethylphenyl)-cyclohexanone oxime; ESMS m/z 440.2 (M+H$^+$).

EXAMPLES 4 AND 5

5-chloro-N$^2$-(2,5-dimethyl-4-(4-trans-morpholinocyclohexyl)phenyl)-N$^4$-(5-methyl-1H-pyrazol-3-yl)pyrimidine-2,4-diamine (37)

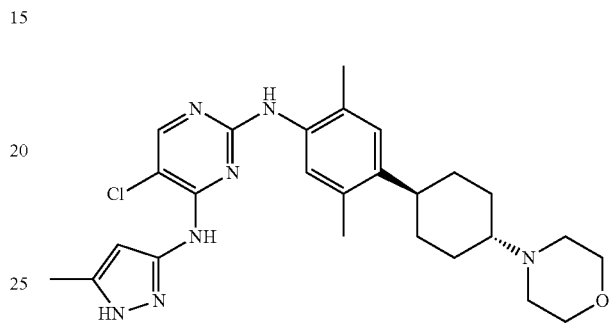

5-chloro-N$^2$-(2,5-dimethyl-4-(4-cis-morpholinocyclohexyl)phenyl)-N$^4$-(5-methyl-1H-pyrazol-3-yl)pyrimidine-2,4-diamine (38)

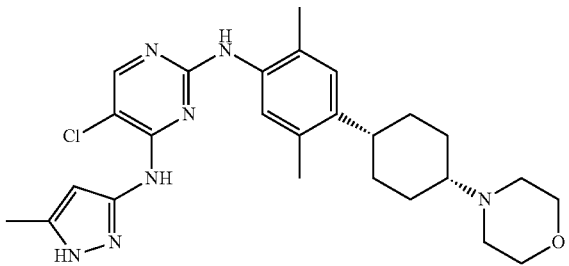 [SMILES: Cc1cc(Nc2nc(Nc3cc(C)c([C@H]4CC[C@@H](N5CCOCC5)CC4)cc3C)ncc2Cl)n[nH]1]

Step 1: A mixture of 1-bromo-2,5-dimethyl-4-nitrobenzene (100 mg, 0.43 mmol), 4,4,5,5-tetramethyl-2-(1,4-dioxaspiro[4.5]dec-7-en-8-yl)-1,3,2-dioxaborolane (112 mg, 0.43 mmol), Pd(PPh$_3$)$_4$ (49 mg, 0.043 mmol) and CsF (196 mg, 1.29 mmol) in a mixture of dimethyl ethylene glycol and water (2:1, 1.5 mL) was degassed and heated under N$_2$ at 130° C. in microwave reactor for 15 min. After cooling down to room temperature, the reaction mixture was treated with saturated NH$_4$Cl aqueous solution (5 mL) and extracted with EtOAc (3×4 mL). The combined organic layers were concentrated and purified by flash column chromatography (silica gel, 0%-30% EtOAc in hexanes gradient) to provide 8-(2,5-dimethyl-4-nitrophenyl)-1,4-dioxaspiro[4.5]dec-7-ene as a white solid; ESMS m/z 290.1 (M+H$^+$).

Step 2: A mixture of 8-(2,5-Dimethyl-4-nitrophenyl)-1,4-dioxaspiro[4.5]dec-7-ene (105 mg, 0.36 mmol) and Pd/C (10 mg) in EtOH was degassed and stirred under 1 atm. H$_2$ at room temperature for 14 h. Pd/C was removed by filtration and filtrate was concentrated to provide 2,5-dimethyl-4-(1,4-dioxaspiro[4.5]decan-8-yl)aniline, which was used in the next step without further purification; ESMS m/z 262.2 (M+H$^+$).

Step 3: A mixture of 2,5-dimethyl-4-(1,4-dioxaspiro[4.5]decan-8-yl)aniline (86 mg, 0.33 mmol) and 2,5-dichloro-N-(5-methyl-1H-pyrazol-3-yl)pyrimidin-4-amine (104 mg, 0.43 mmol) in $^i$PrOH (3 mL) was treated with HCl (82 μL, 4N in dioxane, 0.33 mmol) and heated to 125° C. in a sealed tube for 14 h. After cooling down to room temperature, the mixture was concentrated and was treated with acetone (2 mL) and HCl (330 μL, 4N in dioxane) at room temperature for 5 h. The mixture was then treated with saturated NaHCO$_3$ aqueous solution (10 mL) and extracted with EtOAc (3×10 mL). The organic layers were combined, concentrated and purified by flash column chromatography (silica gel, 0%-100% EtOAc in hexanes gradient) to provide 4-(4-(5-chloro-4-(5-methyl-1H-pyrazol-3-ylamino)pyrimidin-2-ylamino)-2,5-dimethylphenyl)cyclohexanone as white solid; ESMS m/z 425.2 (M+H$^+$).

Step 4: To a solution of 4-(4-(5-chloro-4-(5-methyl-1H-pyrazol-3-ylamino)pyrimidin-2-ylamino)-2,5-dimethylphenyl)cyclohexanone (30 mg, 0.071 mmol) in 1,2-dichloroethane (1 mL) was added morpholine (9 mg, 0.11 mmol) followed by AcOH (6.5 mg, 0.11 mmol) and 4 Å molecular sieves. The mixture was stirred at room temperature for 1 h before the addition of sodium triacetoxyborohydride (22.5 mg, 0.11 mmol). The mixture was stirred at room temperature for 14 h at which point additional morpholine (5 mg, 0.058 mmol) and sodium triacetoxyborohydride (10 mg, 0.047 mmol) was added and stirred at room temperature for an additional 5 h. The reaction mixture was then treated with saturated NH$_4$Cl aqueous solution (3 mL) and extracted with EtOAc (3×4 mL). The combined organic layers were concentrated and purified by preparative silica thin layer chromatography (7% MeOH/CH$_2$Cl$_2$ with 0.2% NH$_3$) to provide 5-chloro-N$^2$-(2,5-dimethyl-4-(4-cis-morpholinocyclohexyl)phenyl)-N$^4$-(5-methyl-1H-pyrazol-3-yl)pyrimidine-2,4-diamine_as the less polar isomer; $^1$H NMR (400 MHz, DMSO-d$_6$) δ 12.01 (br, 1H), 8.49 (br, 2H), 7.98 (s, 1H), 7.10 (s, 1H), 7.00 (s, 1H), 6.13 (br, 1H), 3.64 (m, 4H), 2.75 (m, 1H), 2.41 (m, 4H), 2.24 (s, 3H), 2.00-2.20 (m, 9H), 1.70-1.85 (m, 2H), 1.35-1.55 (m, 4H); ESMS m/z 496.3 (M+H$^+$) and 5-chloro-N$^2$-(2,5-dimethyl-4-(4-trans-morpholinocyclohexyl)phenyl)-N$^4$-(5-methyl-1H-pyrazol-3-yl)pyrimidine-2,4-diamine_as the more polar isomer; $^1$H NMR (400 MHz, DMSO-d$_6$) δ 12.01 (br, 1H), 8.47 (br, 2H), 7.98 (s, 1H), 7.14 (s, 1H), 7.02 (s, 1H), 6.13 (br, 1H), 3.57 (br, 4H), 2.60 (m, 1H), 2.50 (br, 4H), 2.32 (m, 1H), 2.22 (s, 3H), 2.13 (s, 3H), 2.10 (s, 3H), 1.93 (b, 2H), 1.79 (b, 2H), 1.30-1.55 (m, 4H); ESMS m/z 496.3 (M+H$^+$).

EXAMPLE 6

5-Chloro-N$^2$-(2,5-dimethyl-4-(morpholinomethyl)phenyl)-N$^4$-(5-methyl-1H-pyrazol-3-yl)pyrimidine-2,4-diamine (39)

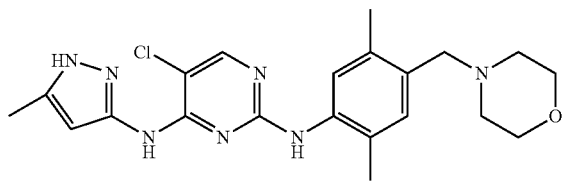 [SMILES: Cc1cc(Nc2nc(Nc3cc(C)c(CN4CCOCC4)cc3C)ncc2Cl)n[nH]1]

Step 1: A mixture of 2,5-dichloro-N-(5-methyl-1H-pyrazol-3-yl)pyrimidin-4-amine (732 mg, 3 mmol), 4-bromo-2,5-dimethylaniline (554 mg, 2 mmol) and conc. aqueous HCl (1.5 mL) in iso-propanol (15 mL) was heated in a microwave for 40 min at 130° C. LCMS showed that the reaction was not complete, and additional 2,5-dichloro-N-(5-methyl-1H-pyrazol-3-yl)pyrimidin-4-amine (732 mg, 3 mmol) was added to the reaction. The reaction was again heated in a microwave for an additional 60 min at 130° C. The crude reaction mixture was then diluted with EtOAc (100 mL), sequentially washed with saturated aqueous NaHCO$_3$ (2×20 mL) and brine (10 mL), dried over Na$_2$CO$_3$ and concentrated in vacuo. The crude product was purified by silica chromatography (0-10% MeOH in EtOAc gradient with 1% NH$_3$ additive) to give N$^2$-(4-bromo-2,5-dimethylphenyl)-5-chloro-N$^4$-(5-methyl-1H-pyrazol-3-yl)pyrimidine-2,4-diamine as an off-white solid; ESMS m/z 407.2 (M+H$^+$).

Step 2: A mixture of N$^2$-(4-bromo-2,5-dimethylphenyl)-5-chloro-N$^4$-(5-methyl-1H-pyrazol-3-yl)pyrimidine-2,4-diamine (41 mg, 0.1 mmol), potassium 1-trifluoroboratomethylmorpholine (43 mg, 0.2 mmol), Pd(OAc)$_2$ (3 mg, 0.013 mmol), Xantphos (12 mg, 0.025 mmol) and Cs$_2$CO$_3$ (98 mg, 0.3 mmol) in THF (1 mL)/H$_2$O (0.1 mL) was degassed by a stream of argon gas. The vial was sealed and heated in a microwave for 30 min at 160° C. Additional potassium 1-trifluoroboratomethylmorpholine (69 mg), Xantphos (18 mg) and Cs$_2$CO$_3$ (98 mg) were added. The reaction was again heated in the microwave for an additional 30 min at 160° C. The crude product is purified by RP-HPLC to give 5-Chloro-N2-(2,5-dimethyl-4-(morpholinomethyl)phenyl)-N4-(5-methyl-1H-pyrazol-3-yl)pyrimidine-2,4-diamine as a white powder; ESMS m/z 428.2 (M+H$^+$).

EXAMPLE 7

4-(2,5-dimethyl-4-(4-(5-methyl-1H-pyrazol-3-ylamino)-5-(trifluoromethyl)pyrimidin-2-ylamino)phenyl)cyclohexanone (40)

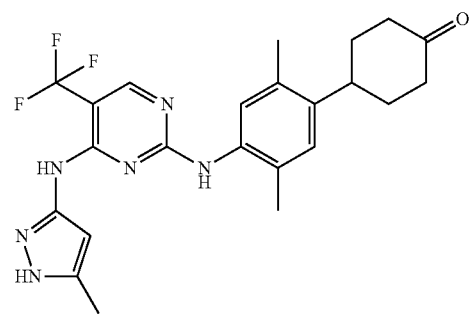 [SMILES: Cc1cc(Nc2nc(Nc3cc(C)c(C4CCC(=O)CC4)cc3C)ncc2C(F)(F)F)n[nH]1]

A mixture of 2,5-dimethyl-4-(1,4-dioxaspiro[4.5]decan-8-yl)aniline (111.3 mg, 0.43 mmol), 2-chloro-N-(5-methyl-1H-pyrazol-3-yl)-5-(trifluoromethyl)pyrimidin-4-amine (119.6 mg, 0.43 mmol), HCl (4 N in water, 0.11 mL, 0.43 mmol) in i-PrOH (4.0 mL) was heated at 125° C. in an oil bath over night. The reaction mixture was concentrated in vacuo. The crude product was dissolved in THF (2 mL), MeOH (1 mL) and HCl (4N in water, 0.11 mL, 0.43 mmol), and stirred at room temperature for 2 h. The reaction mixture was concentrated in vacuo, followed by purification by silica chromatography (0-100% EtOAc in hexanes gradient) to afford 4-(2,5-dimethyl-4-(4-(5-methyl-1H-pyrazol-3-ylamino)-5-(trifluoromethyl)pyrimidin-2-ylamino)phenyl)cyclohexanone; ESMS m/z 459.2 (M+H$^+$).

EXAMPLE 8 trans-4-(2,5-dimethyl-4-(4-(5-methyl-1H-pyrazol-3-ylamino)-5-(trifluoromethyl)pyrimidin-2-ylamino)phenyl)cyclohexanol (41)

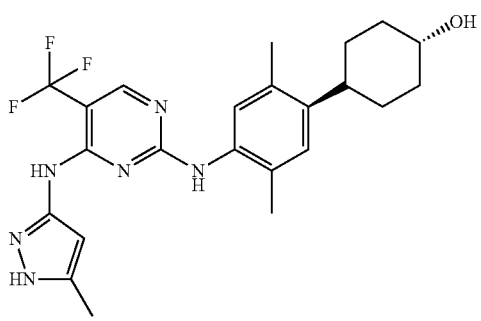

To a solution of 4-(2,5-dimethyl-4-(4-(5-methyl-1H-pyrazol-3-ylamino)-5-(trifluoromethyl)pyrimidin-2-ylamino)phenyl)cyclohexanone (100 mg, 0.22 mmol) in MeOH (15 mL) was added NaBH$_4$ (33.2 mg, 0.87 mmol). The reaction was stirred 30 for min., concentrated and purified by silica chromatography (MeOH/DCM: 8:92) to afford trans-4-(2,5-dimethyl-4-(4-(5-methyl-1H-pyrazol-3-ylamino)-5-(trifluoromethyl)pyrimidin-2-ylamino)phenyl)cyclohexanol; R$_f$: 0.35 (silica; MeOH/DCM 8:92); ESMS m/z 461.2 (M+H$^+$).

EXAMPLE 9 cis-4-(2,5-dimethyl-4-(4-(5-methyl-1H-pyrazol-3-ylamino)-5-(trifluoromethyl)pyrimidin-2-ylamino)phenyl)cyclohexanol (42)

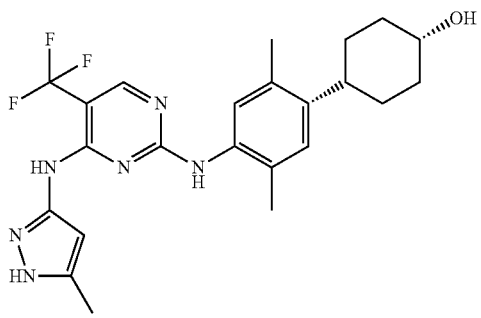

To a solution of 4-(2,5-dimethyl-4-(4-(5-methyl-1H-pyrazol-3-ylamino)-5-(trifluoromethyl)pyrimidin-2-ylamino)phenyl)cyclohexanone (100 mg, 0.22 mmol) in MeOH (15 mL) was added NaBH$_4$ (33.2 mg, 0.87 mmol). The reaction was stirred for 30 mins., concentrated and purified by silica chromatography (MeOH/DCM: 8:92) to afford cis-4-(2,5-dimethyl-1H-pyrazol-3-ylamino)-5-(trifluoromethyl)pyrimidin-2-ylamino)phenyl)cyclohexanol; R$_f$: 0.45 (silica; MeOH/DCM 8:92); ESMS m/z 461.2 (M+H$^+$).

EXAMPLE 10

N$^2$-(2-fluoro-5-methyl-4-(cis-4-(piperidin-1-yl)cyclohexyl)phenyl)-N$^4$-(5-methyl-1H-pyrazol-3-yl)-5-(trifluoromethyl)pyrimidine-2,4-diamine (62)

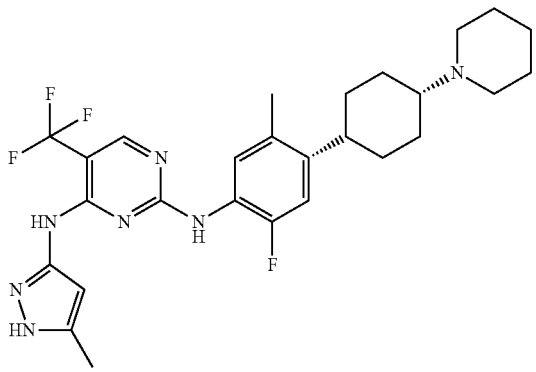

A mixture of 4-(5-fluoro-2-methyl-4-(4-(5-methyl-1H-pyrazol-3-ylamino)-5-(trifluoromethyl)pyrimidin-2-ylamino)phenyl)cyclohexanone (30 mg, 0.065 mmol), piperidine (30 µL, 0.174 mmol) and acetic acid (75 µL, 0.13 mmol) was stirred at room temperature for 1 h. Sodium triacetoxyborohydride (27.4 mg, 0.13 mmol) was added to the reaction and the reaction mixture was stirred overnight. The mixture was concentrated and purified by silica chromatography (MeOH/DCM 8:92) to afford N$^2$-(2-fluoro-5-methyl-4-(cis-4-(piperidin-1-yl)cyclohexyl)phenyl)-N$^4$-(5-methyl-1H-pyrazol-3-yl)-5-(trifluoromethyl)pyrimidine-2,4-diamine; R$_f$: 0.41 (Silica; MeOH/DCM 8:92); ESMS m/z 532.3 (M+H$^+$).

EXAMPLE 11

N$^2$-(2-fluoro-5-methyl-4-(trans-4-(piperidin-1-yl)cyclohexyl)phenyl)-N$^4$-(5-methyl-1H-pyrazol-3-yl)-5-(trifluoromethyl)pyrimidine-2,4-diamine (63)

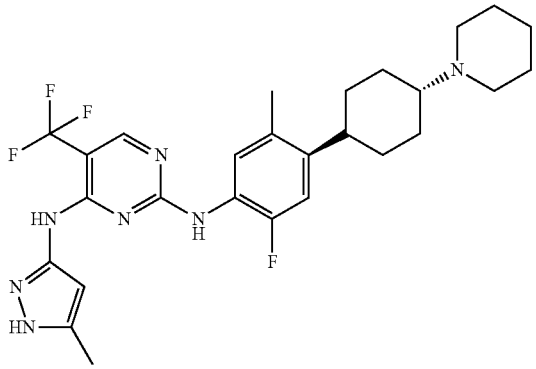

A mixture of 4-(5-fluoro-2-methyl-4-(4-(5-methyl-1H-pyrazol-3-ylamino)-5-(trifluoromethyl)pyrimidin-2-ylamino)phenyl)cyclohexanone (30 mg, 0.065 mmol), piperidine (30 µL, 0.174 mmol) and acetic acid (75 µL, 0.13 mmol) was stirred at room temperature for 1 h. Sodium triacetoxyborohydride (27.4 mg, 0.13 mmol) was added to the reaction and the reaction mixture was stirred overnight. The mixture was concentrated and purified by silica chromatography (MeOH/DCM 8:92) to afford N²-(2-fluoro-5-methyl-4-(trans-4-(piperidin-1-yl)cyclohexyl)phenyl)-N⁴-(5-methyl-1H-pyrazol-3-yl)-5-(trifluoromethyl)pyrimidine-2,4-diamine; $R_f$: 0.32 (Silica; MeOH/DCM 8:92); ESMS m/z 532.3 (M+H⁺).

EXAMPLE 12

N²-(2,5-dimethyl-4-(cis-4-morpholinocyclohexyl) phenyl)-N⁴-(5-methyl-1H-pyrazol-3-yl)-5-(trifluoromethyl)pyrimidine-2,4-diamine (66)

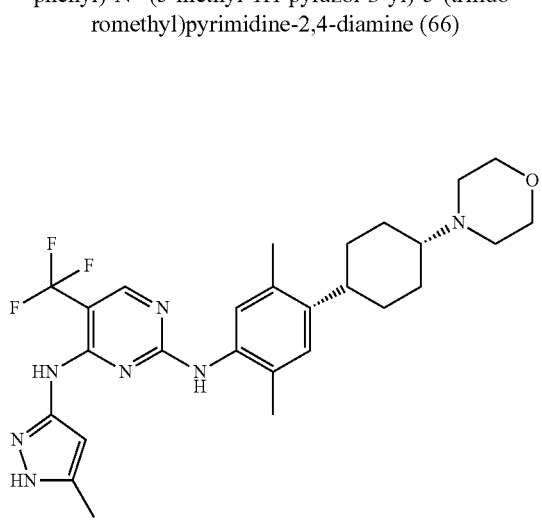

A mixture of 4-(2,5-dimethyl-4-(4-(5-methyl-1H-pyrazol-3-ylamino)-5-(trifluoromethyl)pyrimidin-2-ylamino)phenyl)cyclohexanone (40 mg, 0.087 mmol), morpholine (15 µL, 0.174 mmol) and acetic acid (75 µL, 0.13 mmol) was stirred at room temperature for 1 h. Sodium cyanoborohydride (8.2 mg, 0.13 mmol) was added to the reaction and the reaction mixture was stirred overnight. The mixture was concentrated and purified by silica chromatography (MeOH/DCM 8:92) to afford N²-(2,5-dimethyl-4-(cis-4-morpholinocyclohexyl) phenyl)-N⁴-(5-methyl-1H-pyrazol-3-yl)-5-(trifluoromethyl) pyrimidine-2,4-diamine; $R_f$: 0.50 (Silica; MeOH/DCM 8:92); ESMS m/z 530.3 (M+H⁺).

EXAMPLE 13

N²-(2,5-dimethyl-4-(trans-4-morpholinocyclohexyl) phenyl)-N⁴-(5-methyl-1H-pyrazol-3-yl)-5-(trifluoromethyl)pyrimidine-2,4-diamine (67)

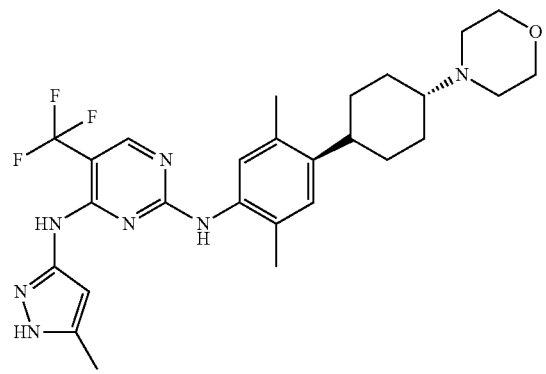

A mixture of 4-(2,5-dimethyl-4-(4-(5-methyl-1H-pyrazol-3-ylamino)-5-(trifluoromethyl)pyrimidin-2-ylamino)phenyl)cyclohexanone (40 mg, 0.087 mmol), morpholine (15 µL, 0.174 mmol) and acetic acid (75 µL, 0.13 mmol) was stirred at room temperature for 1 h. Sodium cyanoborohydride (8.2 mg, 0.13 mmol) was added to the reaction and the reaction mixture was stirred overnight. The mixture was concentrated and purified by silica chromatography (MeOH/DCM 8:92) to afford N²-(2,5-dimethyl-4-(trans-4-morpholinocyclohexyl) phenyl)-N⁴-(5-methyl-1H-pyrazol-3-yl)-5-(trifluoromethyl) pyrimidine-2,4-diamine; $R_f$: 0.38 (Silica; MeOH/DCM 8:92); ESMS m/z 530.3 (M+H⁺).

The following compounds in Table 1 are obtained by repeating the procedures described in examples above and using appropriate starting materials.

TABLE 1

| | STRUCTURE | NMR or ESMS | IGF1R Ba/F3 IC50 (uM) |
|---|---|---|---|
| 1 | 5-chloro-N2-(2-fluoro-5-methyl-4-(1-methyl-1H-pyrazol-4-yl)phenyl)-N4-(5-methyl-1H-pyrazol-3-yl)pyrimidine-2,4-diamine | ESMS m/z 413.1 (M + H+). | 0.067 |

TABLE 1-continued

| | STRUCTURE | NMR or ESMS | IGF1R Ba/F3 IC50 (uM) |
|---|---|---|---|
| 2 | 5-chloro-N2-(2-fluoro-5-methyl-4-(pyridin-4-yl)phenyl)-N4-(5-methyl-1H-pyrazol-3-yl)pyrimidine-2,4-diamine | ESMS m/z 410.1 (M + H+). | 0.103 |
| 3 | 5-chloro-N2-(2-fluoro-5-methyl-4-(pyridin-3-yl)phenyl)-N4-(5-methyl-1H-pyrazol-3-yl)pyrimidine-2,4-diamine | ESMS m/z 410.1 (M + H+). | 0.067 |
| 4 | 5-(4-(5-chloro-4-(5-methyl-1H-pyrazol-3-ylamino)pyrimidin-2-ylamino)-5-fluoro-2-methylphenyl)-N-methylpicolinamide | 1H NMR (400 MHz, DMSO-d6) δ 9.22 (br, 2H), 8.85 (m, 1H), 8.63 (m, 1H), 8.16 (s, 1H), 8.09 (m, 1H), 8.07 (m, 1H), 7.85 (br, 1H), 7.27 (m, 1H), 6.19 (s, 1H), 2.84 (d, 3H), 2.20 (s, 3H), 2.15 (s, 3H); ESMS m/z 467.1 (M + H+). | 0.089 |
| 5 | 5-chloro-N2-(2-fluoro-5-methyl-4-(6-methylpyridin-3-yl)phenyl)-N4-(5-methyl-1H-pyrazol-3-yl)pyrimidine-2,4-diamine | ESMS m/z 424.1 (M + H+). | 0.137 |
| 6 | 5-chloro-N2-(2-fluoro-5-methyl-4-(pyridin-2-yl)phenyl)-N4-(5-methyl-1H-pyrazol-3-yl)pyrimidine-2,4-diamine | ESMS m/z 410.1 (M + H+). | 0.294 |

TABLE 1-continued

| | STRUCTURE | NMR or ESMS | IGF1R Ba/F3 IC50 (uM) |
|---|---|---|---|
| 7 | 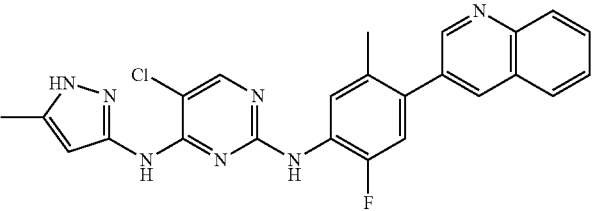 [SMILES: Cc1cc(Nc2nc(Nc3cc(C)c(-c4cnc5ccccc5c4)cc3F)ncc2Cl)n[nH]1] 5-chloro-N2-(2-fluoro-5-methyl-4-(quinolin-3-yl)phenyl)-N4-(5-methyl-1H-pyrazol-3-yl)pyrimidine-2,4-diamine | ESMS m/z 460.1 (M + H+). | 0.579 |
| 8 | 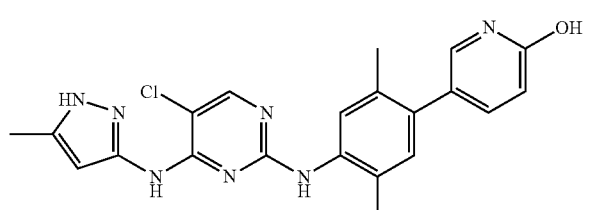 5-(4-(5-chloro-4-(5-methyl-1H-pyrazol-3-ylamino)pyrimidin-2-ylamino)-5-fluoro-2-methylphenyl)pyridin-2-ol | ESMS m/z 426.1 (M + H+). | 0.055 |
| 9 | 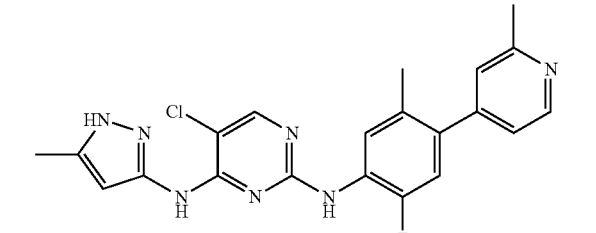 5-chloro-N2-(2-fluoro-5-methyl-4-(2-methylpyridin-4-yl)phenyl)-N4-(5-methyl-1H-pyrazol-3-yl)pyrimidine-2,4-diamine | ESMS m/z 424.1 (M + H+). | 0.094 |
| 10 | 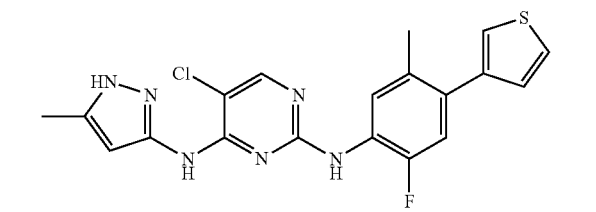 5-chloro-N2-(2-fluoro-5-methyl-4-(thiophen-3-yl)phenyl)-N4-(5-methyl-1H-pyrazol-3-yl)pyrimidine-2,4-diamine | ESMS m/z 415.1 (M + H+). | 0.833 |
| 11 | 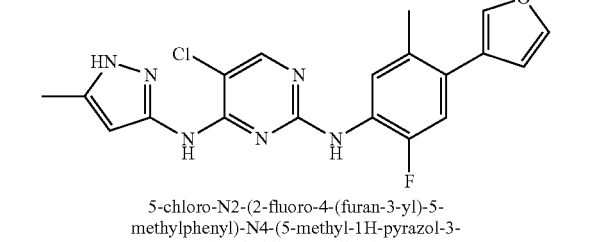 5-chloro-N2-(2-fluoro-4-(furan-3-yl)-5-methylphenyl)-N4-(5-methyl-1H-pyrazol-3-yl)pyrimidine-2,4-diamine | ESMS m/z 399.1 (M + H+). | 0.683 |

TABLE 1-continued

| | STRUCTURE | NMR or ESMS | IGF1R Ba/F3 IC50 (uM) |
|---|---|---|---|
| 12 | 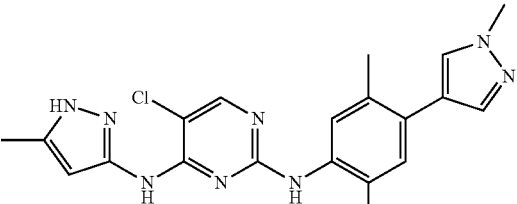<br>5-chloro-N2-(2,5-dimethyl-4-(1-methyl-1H-pyrazol-4-yl)phenyl)-N4-(5-methyl-1H-pyrazol-3-yl)pyrimidine-2,4-diamine | 1H NMR (400 MHz, DMSO-d6) δ 9.67 (br, 2H), 9.30 (br, 1H), 8.12 (s, 1H), 7.96 (s, 1H), 7.68 (s, 1H), 7.31 (s, 1H), 7.28 (s, 1H), 6.97 (s, 1H), 3.89 (s, 3H), 2.33 (s, 3H), 2.18 (s, 3H), 2.07 (s, 3H); ESMS m/z 409.1 (M + H+) | 0.025 |
| 13 | 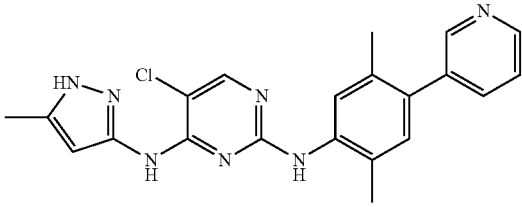 [SMILES: Cc1cc(Nc2nc(Nc3cc(C)c(-c4cccnc4)cc3C)ncc2Cl)n[nH]1]<br>5-chloro-N2-(2-fluoro-4-(furan-3-yl)-5-methylphenyl)-N4-(5-methyl-1H-pyrazol-3-yl)pyrimidine-2,4-diamine | ESMS m/z 406.1 (M + H+). | 0.029 |
| 14 | 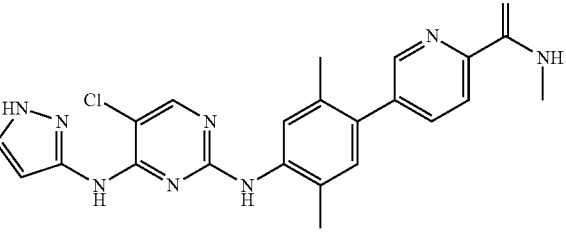<br>5-(4-(5-chloro-4-(5-methyl-1H-pyrazol-3-ylamino)pyrimidin-2-ylamino)-2,5-dimethylphenyl)-N-methylpicolinamide | ESMS m/z 463.2 (M + H+). | 0.015 |
| 15 | 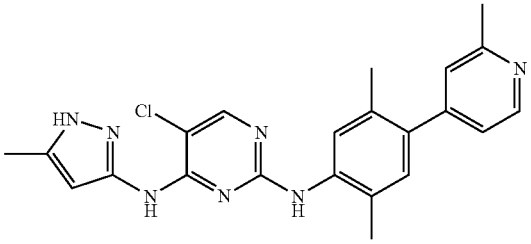 [SMILES: Cc1cc(-c2cc(C)c(Nc3ncc(Cl)c(Nc4cc(C)[nH]n4)n3)cc2C)ccn1]<br>5-chloro-N2-(2,5-dimethyl-4-(2-methylpyridin-4-yl)phenyl)-N4-(5-methyl-1H-pyrazol-3-yl)pyrimidine-2,4-diamine | ESMS m/z 420.2 (M + H+). | 0.039 |
| 16 | 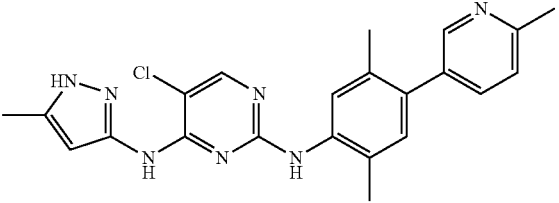<br>5-chloro-N2-(2,5-dimethyl-4-(6-methylpyridin-3-yl)phenyl)-N4-(5-methyl-1H-pyrazol-3-yl)pyrimidine-2,4-diamine | ESMS m/z 420.2 (M + H+). | 0.030 |

TABLE 1-continued

| | STRUCTURE | NMR or ESMS | IGF1R Ba/F3 IC50 (uM) |
|---|---|---|---|
| 17 | N2-(4-(1H-imidazol-2-yl)-2,5-dimethylphenyl)-5-chloro-N4-(5-methyl-1H-pyrazol-3-yl)pyrimidine-2,4-diamine | 1H NMR (400 MHz, DMSO-d6) δ 9.01 (br, 2h), 8.83 (s, 1h), 8.12 (s, 1H), 7.83 (s, 2H(, 7.78 (s, 1H), 7.45 (s, 1H), 6.20 (s, 1H), 2.30 (s, 3H), 2.29 (s, 3H), 2.15 (s, 3H); ESMS m/z 395 (M + H+). | 0.068 |
| 18 | 5-chloro-N2-(2,5-dimethyl-4-(3-methylisoxazol-5-yl)phenyl)-N4-(5-methyl-1H-pyrazol-3-yl)pyrimidine-2,4-diamine | 1H NMR (400 MHz, DMSO-d6) δ 9.3 (br, 2H), 9.0 (br, 1H), 8.13 (s, 1H), 7.58 (s, 1H), 7.55 (s, 1H), 6.64 (s, 1H), 6.07 (s, 1H), 2.39 (s, 3H), 2.30 (s, 3H), 2.25 (s, 3H), 2.09 (s, 3H); ESMS m/z 410.1 (M + H+). | 0.276 |
| 19 | 5-chloro-N2-(2-fluoro-4-(1H-imidazol-2-yl)-5-methylphenyl)-N4-(5-methyl-1H-pyrazol-3-yl)pyrimidine-2,4-diamine | ESMS m/z 399.1 (M + H+). | 0.288 |
| 20 | 5-chloro-N2-(2,5-dimethyl-4-(oxazol-5-yl)phenyl)-N4-(5-methyl-1H-pyrazol-3-yl)pyrimidine-2,4-diamine | 1H NMR (400 MHz, DMSO-d6) δ 9.40 (br, 2H), 9.14 (br 1H), 8.47 (s, 1H) 8.14 (s, 1H), 7.56 (s, 1H), 7.48 (s, 1H), 7.45 (s, 1H), 6.03 (s, 1H), 2.39 (s, 3H), 2.24 (s, 3H), 2.06 (s, 3H); ESMS m/z 396.1 (M + H+). | 0.109 |
| 21 | 5-chloro-N2-(2-methoxy-5-methyl-4-(oxazol-5-yl)phenyl)-N4-(5-methyl-1H-pyrazol-3-yl)pyrimidine-2,4-diamine | ESMS m/z 412.1 (M + H+). | 0.169 |

TABLE 1-continued

| | STRUCTURE | NMR or ESMS | IGF1R Ba/F3 IC50 (uM) |
|---|---|---|---|
| 22 | 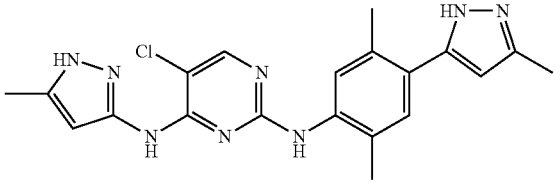<br>5-chloro-N2-(2,5-dimethyl-4-(3-methyl-1H-pyrazol-5-yl)phenyl)-N4-(5-methyl-1H-pyrazol-3-yl)pyrimidine-2,4-diamine | ESMS m/z 409.2 (M + H+). | 0.166 |
| 23 | 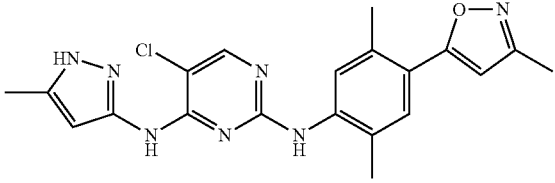<br>5-chloro-N2-(2,5-dimethyl-4-(3-methylisoxazol-5-yl)phenyl)-N4-(5-methyl-1H-pyrazol-3-yl)pyrimidine-2,4-diamine | 1H NMR (400 MHz, DMSO-d6) δ 9.3 (br, 2H), 9.0 (br, 1H), 8.13 (s, 1H), 7.58 (s, 1H), 7.55 (s, 1H), 6.64 (s, 1H), 6.07 (s, 1H), 2.39 (s, 3H), 2.30 (s, 3H), 2.25 (s, 3H), 2.09 (s, 3H); ESMS m/z 410.1 (M + H+). | |
| 24 | 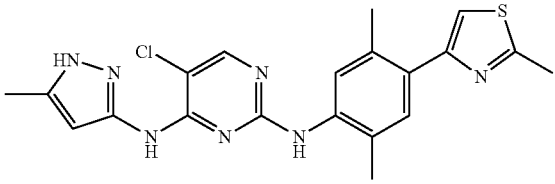<br>5-chloro-N2-(2,5-dimethyl-4-(2-methylthiazol-4-yl)phenyl)-N4-(5-methyl-1H-pyrazol-3-yl)pyrimidine-2,4-diamine | 1H NMR (400 MHz, DMSO-d6) 9.56 (br, 2H), 9.25 (br, 1H), 8.14 (s, 2H), 7.56 (s, 1H), 7.53 (s, 1H), 7.37 (s, 1H), 6.07 (s, 1H), 2.71 (s, 3H), 2.37 (s, 3H), 2.21 (s, 3H), 2.09 (s, 3H); ESMS m/z 426.1 (M + H+). | 0.106 |
| 25 | 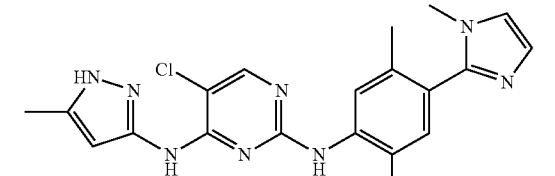<br>5-chloro-N2-(2,5-dimethyl-4-(1-methyl-1H-imidazol-2-yl)phenyl)-N4-(5-methyl-1H-pyrazol-3-yl)pyrimidine-2,4-diamine | ESMS m/z 409.2 (M + H+). | 0.071 |
| 26 | 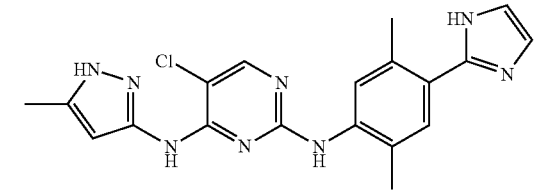 [SMILES: Cc1cc(Nc2nc(Nc3cc(C)c(-c4ncc[nH]4)cc3C)ncc2Cl)n[nH]1]<br>N2-(4-(1H-imidazol-2-yl)-2,5-dimethylphenyl)-5-chloro-N4-(5-methyl-1H-pyrazol-3-yl)pyrimidine-2,4-diamine | 1H NMR (400 MHz, DMSO-d6) 9.01 (br, 2h), 8.83 (s, 1h), 8.12 (s, 1H), 7.83 (s, 2H(, 7.78 (s, 1H), 7.45 (s, 1H), 6.20 (s, 1H), 2.30 (s, 3H), 2.29 (s, 3H), 2.15 (s, 3H); ESMS m/z 395.1 (M + H+). | |

TABLE 1-continued

| | STRUCTURE | NMR or ESMS | IGF1R Ba/F3 IC50 (uM) |
|---|---|---|---|
| 27 | 5-chloro-N2-(5-fluoro-2-methyl-4-(1-methyl-1H-pyrazol-4-yl)phenyl)-N4-(5-methyl-1H-pyrazol-3-yl)pyrimidine-2,4-diamine | ESMS m/z 412.8 (M + H$^+$) | 0.549 |
| 28 | 1-(4-(5-chloro-4-(5-methyl-1H-pyrazol-3-ylamino)pyrimidin-2-ylamino)-2,5-dimethylphenyl)ethanone O-2-hydroxyethyl oxime | ESMS m/z 430.2 (M + H$^+$) | 0.141 |
| 29 | 1-(4-(5-chloro-4-(5-methyl-1H-pyrazol-3-ylamino)pyrimidin-2-ylamino)-2,5-dimethylphenyl)ethanone oxime | ESMS m/z 386.1 (M + H$^+$) | 0.051 |
| 30 | 4-(5-chloro-4-(5-methyl-1H-pyrazol-3-ylamino)pyrimidin-2-ylamino)-N,N,2,5-tetramethylbenzamide | ESMS m/z 400.2 (M + H$^+$) | 0.539 |
| 31 | 4-(5-chloro-4-(5-methyl-1H-pyrazol-3-ylamino)pyrimidin-2-ylamino)-N-(2-dimethylamino)ethyl)-2,5-dimethylbenzamide | ESMS m/z 443.2 (M + H$^+$) | 0.659 |

TABLE 1-continued

| | STRUCTURE | NMR or ESMS | IGF1R Ba/F3 IC50 (uM) |
|---|---|---|---|
| 32 | 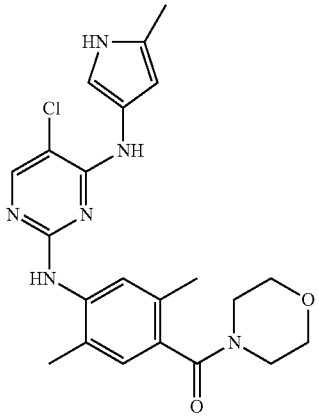 [SMILES: Cc1cc(Nc2nc(Nc3cc(C)c(C(=O)N4CCOCC4)cc3C)ncc2Cl)c[nH]1]<br>(4-(5-chloro-4-(5-methyl-1H-pyrazol-3-ylamino)pyrimidin-2-ylamino)-2,5-dimethylphenyl)(morpholino)methanone | ESMS m/z 442.2 (M + H+) | 0.451 |
| 33 | 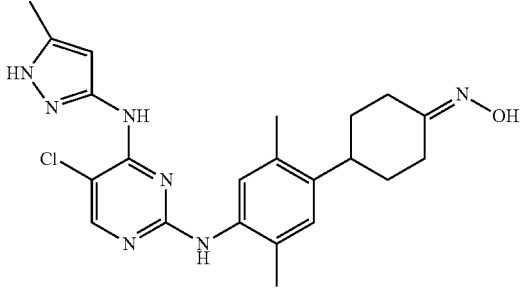 [SMILES: Cc1cc(Nc2nc(Nc3cc(C)c(C4CCC(=NO)CC4)cc3C)ncc2Cl)n[nH]1]<br>4-(4-(5-chloro-4-(5-methyl-1H-pyrazol-3-ylamino)pyrimidin-2-ylamino)-2,5-dimethylphenyl)cyclohexanone oxime | ESMS m/z 440.2 (M + H+) | 0.015 |
| 34 | 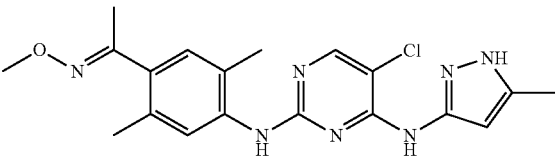<br>1-(4-(5-chloro-4-(5-methyl-1H-pyrazol-3-ylamino)pyrimidin-2-ylamino)-2,5-dimethylphenyl)ethanone O-methyl oxime | ESMS m/z 400.2 (M + H+) | 0.269 |
| 35 | 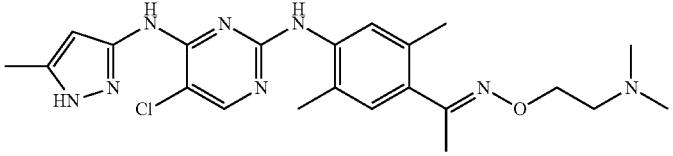<br>1-(4-(5-chloro-4-(5-methyl-1H-pyrazol-3-ylamino)pyrimidin-2-ylamino)-2,5-dimethylphenyl)ethanone O-2-(dimethylamino)ethyl oxime | ESMS m/z 457.2 (M + H+) | 0.121 |

TABLE 1-continued

| | STRUCTURE | NMR or ESMS | IGF1R Ba/F3 IC50 (uM) |
|---|---|---|---|
| 36 | 1-(4-(5-chloro-4-(5-methyl-1H-pyrazol-3-ylamino)pyrimidin-2-ylamino)-2,5-dimethylphenyl)ethanone O-2-morpholinoethyl oxime | ESMS m/z 499.2 (M + H+) | 0.187 |
| 37 | Trans-5-chloro-N2-(2,5-dimethyl-4-(4-morpholinocyclohexyl)phenyl)-N4-(5-methyl-1H-pyrazol-3-yl)pyrimidine-2,4-diamine | ESMS m/z 496.3 (M + H+) | 0.011 |
| 38 | Cis-5-chloro-N2-(2,5-dimethyl-4-(4-morpholinocyclohexyl)phenyl)-N4-(5-methyl-1H-pyrazol-3-yl)pyrimidine-2,4-diamine | ESMS m/z 496.3 (M + H+) | 0.009 |
| 39 | 5-chloro-N2-(2,5-dimethyl-4-(morpholinomethyl)phenyl)-N4-(5-methyl-1H-pyrazol-3-yl)pyrimidine-2,4-diamine | ESMS m/z 428.2 (M + H+) | 0.151 |
| 40 | 4-(2,5-dimethyl-4-(4-(5-methyl-1H-pyrazol-3-ylamino)-5-(trifluoromethyl)pyrimidin-2-ylamino)phenyl)cyclohexanone | ESMS m/z 459.2 (M + H+) | 0.049 |

TABLE 1-continued

| | STRUCTURE | NMR or ESMS | IGF1R Ba/F3 IC50 (uM) |
|---|---|---|---|
| 41 | trans-4-(2,5-dimethyl-4-(4-(5-methyl-1H-pyrazol-3-ylamino)-5-(trifluoromethyl)pyrimidin-2-ylamino)phenyl)cyclohexanol | ESMS m/z 461.2 (M + H$^+$) | 0.025 |
| 42 | Cis-4-(2,5-dimethyl-4-(4-(5-methyl-1H-pyrazol-3-ylamino)-5-(trifluoromethyl)pyrimidin-2-ylamino)phenyl)cyclohexanol | ESMS m/z 461.2 (M + H$^+$) | 0.053 |
| 43 | Cis-5-chloro-N2-(2,5-dimethyl-4-(4-(pipcridin-1-yl)cyclohexyl)phenyl)-N4-(5-methyl-1H-pyrazol-3-yl)pyrimidine-2,4-diamine | ESMS m/z 494.3 (M + H$^+$) | 0.008 |
| 44 | Trans-5-chloro-N2-(2,5-dimethyl-4-(4-(piperidin-1-yl)cyclohexyl)phenyl)-N4-(5-methyl-1H-pyrazol-3-yl)pyrimidine-2,4-diamine | ESMS m/z 494.3 (M + H$^+$) | 0.007 |

TABLE 1-continued

| | STRUCTURE | NMR or ESMS | IGF1R Ba/F3 IC50 (uM) |
|---|---|---|---|
| 45 | trans-4-(4-(5-chloro-4-(5-methyl-1H-pyrazol-3-ylamino)pyrimidin-2-ylamino)-2,5-dimethylphenyl)cyclohexanol | ESMS m/z 427.2 (M + H+) | 0.014 |
| 46 | Trans-5-chloro-N2-(4-(4-(cyclopropylamino)cyclohexyl)-2,5-dimethylphenyl)-N4-(5-methyl-1H-pyrazol-3-yl)pyrimidine-2,4-diamine | ESMS m/z 466.2 (M + H+) | 0.016 |
| 47 | Cis-5-chloro-N2-(4-(4-(cyclopropylamino)cyclohexyl)-2,5-dimethylphenyl)-N4-(5-methyl-1H-pyrazol-3-yl)pyrimidine-2,4-diamine | ESMS m/z 466.2 (M + H+) | 0.017 |
| 48 | Cis-5-chloro-N2-(2-fluoro-5-methyl-4-(4-(piperidin-1-yl)cyclohexyl)phenyl)-N4-(5-methyl-1H-pyrazol-3-yl)pyrimidine-2,4-diamine | ESMS m/z 498.3 (M + H+) | 0.021 |

TABLE 1-continued

| | STRUCTURE | NMR or ESMS | IGF1R Ba/F3 IC50 (uM) |
|---|---|---|---|
| 49 | 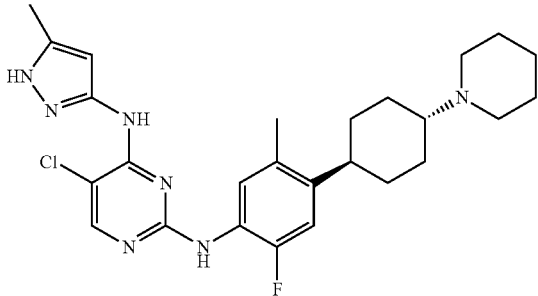 [SMILES: Cc1cc(Nc2nc(Nc3cc(C)c([C@H]4CC[C@H](N5CCCCC5)CC4)cc3F)ncc2Cl)n[nH]1]<br>Trans-5-chloro-N2-(2-fluoro-5-methyl-4-(4-(piperidin-1-yl)cyclohexyl)phenyl)-N4-(5-methyl-1H-pyrazol-3-yl)pyrimidine-2,4-diamine | ESMS m/z 498.3 (M + H$^+$) | 0.040 |
| 50 | 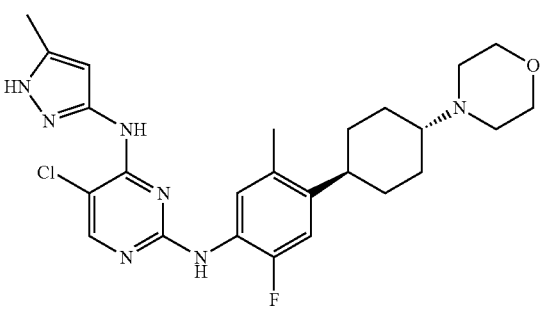 [SMILES: Cc1cc(Nc2nc(Nc3cc(C)c([C@H]4CC[C@H](N5CCOCC5)CC4)cc3F)ncc2Cl)n[nH]1]<br>Trans-5-chloro-N2-(2-fluoro-5-methyl-4-(4-morpholinocyclohexyl)phenyl)-N4-(5-methyl-1H-pyrazol-3-yl)pyrimidine-2,4-diamine | ESMS m/z 500.2 (M + H$^+$) | 0.031 |
| 51 | 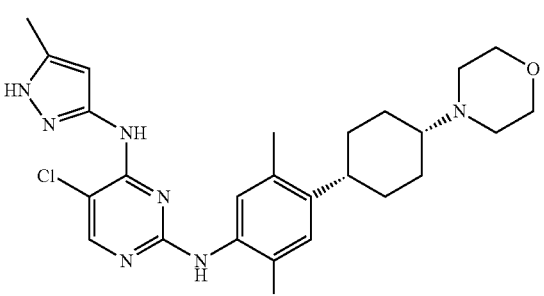<br>Cis-5-chloro-N2-(2-fluoro-5-methyl-4-(4-morpholinocyclohexyl)phenyl)-N4-(5-methyl-1H-pyrazol-3-yl)pyrimidine-2,4-diamine | ESMS m/z 500.2 (M + H$^+$) | 0.400 |
| 52 | 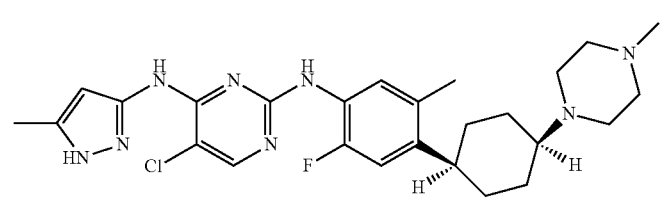<br>Cis-5-chloro-N2-(2-fluoro-5-methyl-4-(4-(4-methylpiperazin-1-yl)cyclohexyl)phenyl)-N4-(5-methyl-1H-pyrazol-3-yl)pyrimidine-2,4-diamine | ESMS m/z 513.3 (M + H$^+$) | 0.024 |

TABLE 1-continued

| | STRUCTURE | NMR or ESMS | IGF1R Ba/F3 IC50 (uM) |
|---|---|---|---|
| 53 | Trans-5-chloro-N2-(2-fluoro-5-methyl-4-(4-(4-methylpiperazin-1-yl)cyclohexyl)phenyl)-N4-(5-methyl-1H-pyrazol-3-yl)pyrimidine-2,4-diamine | ESMS m/z 513.3 (M + H⁺) | 0.025 |
| 54 | (S)-1-((Cis)-4-(4-(5-chloro-4-(5-methyl-1H-pyrazol-3-ylamino)pyrimidin-2-ylamino)-5-fluoro-2-methylphenyl)cyclohexyl)pyrrolidin-3-ol | ESMS m/z 500.2 (M + H⁺) | 0.016 |
| 55 | (S)-1-((Trans)-4-(4-(5-chloro-4-(5-methyl-1H-pyrazol-3-ylamino)pyrimidin-2-ylamino)-5-fluoro-2-methylphenyl)cyclohexyl)pyrrolidin-3-ol | ESMS m/z 500.2 (M + H⁺) | 0.032 |
| 56 | 5-chloro-N2-(4-((cis)-4-(diethylamino)cyclohexyl)-2-fluoro-5-methylphenyl)-N4-(5-methyl-1H-pyrazol-3-yl)pyrimidine-2,4-diamine | ESMS m/z 486.3 (M + H⁺) | 0.025 |
| 57 | 5-chloro-N2-(4-((trans)-4-(diethylamino)cyclohexyl)-2-fluoro-5-methylphenyl)-N4-(5-methyl-1H-pyrazol-3-yl)pyrimidine-2,4-diamine | ESMS m/z 486.3 (M + H⁺) | 0.031 |
| 58 | 5-chloro-N2-(2-fluoro-5-methyl-4-((cis)-4-(piperazin-1-yl)cyclohexyl)phenyl)-N4-(5-methyl-1H-pyrazol-3-yl)pyrimidine-2,4-diamine | ESMS m/z 499.2 (M + H⁺) | 0.017 |

TABLE 1-continued

| | STRUCTURE | NMR or ESMS | IGF1R Ba/F3 IC50 (uM) |
|---|---|---|---|
| 59 | 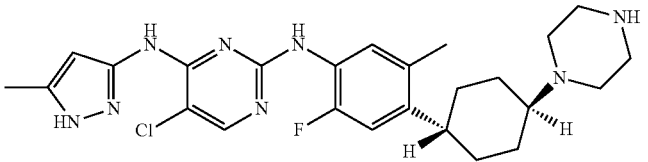 [SMILES: Cc1cc(Nc2nc(Nc3cc(C)c([C@H]4CC[C@H](N5CCNCC5)CC4)cc3F)ncc2Cl)n[nH]1]<br>5-chloro-N2-(2-fluoro-5-methyl-4-((trans)-4-(piperazin-1-yl)cyclohexyl)phenyl)-N4-(5-methyl-1H-pyrazol-3-yl)pyrimidine-2,4-diamine | ESMS m/z 499.2 (M + H⁺) | 0.039 |
| 60 | 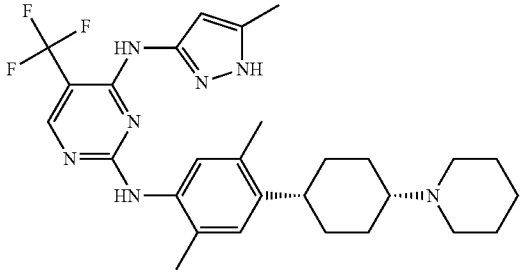 [SMILES: Cc1cc(Nc2nc(Nc3cc(C)c([C@H]4CC[C@@H](N5CCCCC5)CC4)cc3C)ncc2C(F)(F)F)n[nH]1]<br>N2-(2,5-dimethyl-4-((cis)-4-(piperidin-1-yl)cyclohexyl)phenyl)-N4-(5-methyl-1H-pyrazol-3-yl)-5-(trifluoromethyl)pyrimidine-2,4-diamine | ESMS m/z 528.3 (M + H⁺) | 0.004 |
| 61 | 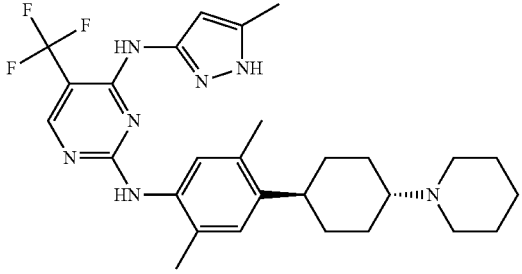 [SMILES: Cc1cc(Nc2nc(Nc3cc(C)c([C@H]4CC[C@H](N5CCCCC5)CC4)cc3C)ncc2C(F)(F)F)n[nH]1]<br>N2-(2,5-dimethyl-4-((trans)-4-(piperidin-1-yl)cyclohexyl)phenyl)-N4-(5-methyl-1H-pyrazol-3-yl)-5-(trifluoromethyl)pyrimidine-2,4-diamine | ESMS m/z 528.3 (M + H⁺) | 0.003 |
| 62 | 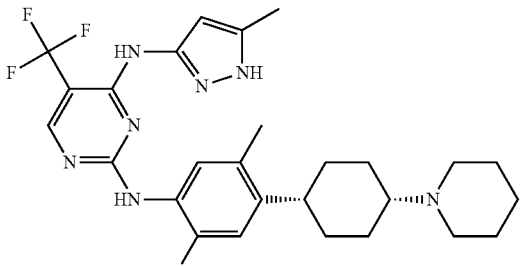<br>N2-(2-fluoro-5-methyl-4-((cis)-4-(piperidin-1-yl)cyclohexyl)phenyl)-N4-(5-methyl-1H-pyrazol-3-yl)-5-(trifluoromethyl)pyrimidine-2,4-diamine | ESMS m/z 532.3 (M + H⁺) | 0.018 |

TABLE 1-continued

| | STRUCTURE | NMR or ESMS | IGF1R Ba/F3 IC50 (uM) |
|---|---|---|---|
| 63 | N2-(2-fluoro-5-methyl-4-((trans)-4-(piperidin-1-yl)cyclohexyl)phenyl)-N4-(5-methyl-1H-pyrazol-3-yl)-5-(trifluoromethyl)pyrimidine-2,4-diamine | ESMS m/z 532.3 (M + H⁺) | 0.016 |
| 64 | N2-(2-fluoro-5-methyl-4-((cis)-4-morpholinocyclohexyl)phenyl)-N4-(5-methyl-1H-pyrazol-3-yl)-5-(trifluoromethyl)pyrimidine-2,4-diamine | ESMS m/z 534.3 (M + H⁺) | 0.05 |
| 65 | N2-(2-fluoro-5-methyl-4-((trans)-4-morpholinocyclohexyl)phenyl)-N4-(5-methyl-1H-pyrazol-3-yl)-5-(trifluoromethyl)pyrimidine-2,4-diamine | ESMS m/z 534.3 (M + H⁺) | 0.032 |
| 66 | N2-(2,5-dimethyl-4-((cis)-4-morpholinocyclohexyl)phenyl)-N4-(5-methyl-1H-pyrazol-3-yl)-5-(trifluoromethyl)pyrimidine-2,4-diamine | ESMS m/z 530.3 (M + H⁺) | 0.014 |

TABLE 1-continued

| | STRUCTURE | NMR or ESMS | IGF1R Ba/F3 IC50 (uM) |
|---|---|---|---|
| 67 | 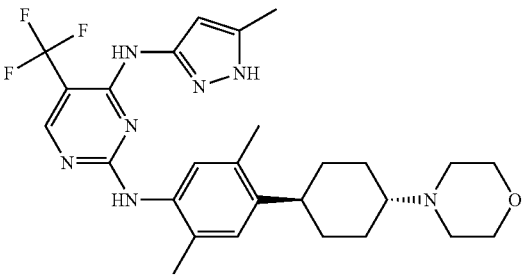 [SMILES: Cc1cc(Nc2nc(Nc3cc(C)c([C@H]4CC[C@H](N5CCOCC5)CC4)cc3C)ncc2C(F)(F)F)n[nH]1]<br>N2-(2,5-dimethyl-4-((trans)-4-morpholinocyclohexyl)phenyl)-N4-(5-methyl-1H-pyrazol-3-yl)-5-(trifluoromethyl)pyrimidine-2,4-diamine | ESMS m/z 530.3 (M + H⁺) | 0.009 |
| 68 | 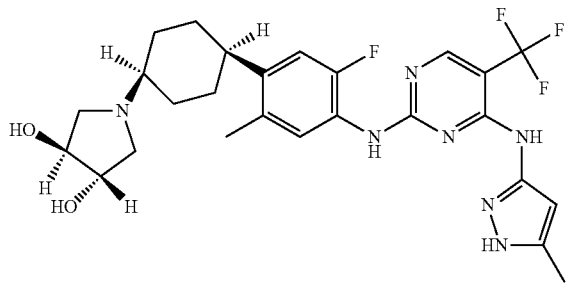 [SMILES: Cc1cc(Nc2nc(Nc3cc(C)c([C@H]4CC[C@@H](N5C[C@H](O)[C@@H](O)C5)CC4)cc3F)ncc2C(F)(F)F)n[nH]1]<br>(3S,4S)-1-((cis)-4-(5-fluoro-2-methyl-4-(4-(5-methyl-1H-pyrazol-3-ylamino)-5-(trifluoromethyl)pyrimidin-2-ylamino)phenyl)cyclohexyl)pyrrolidine-3,4-diol | ESMS m/z 550.3 (M + H⁺) | 0.12 |
| 69 | 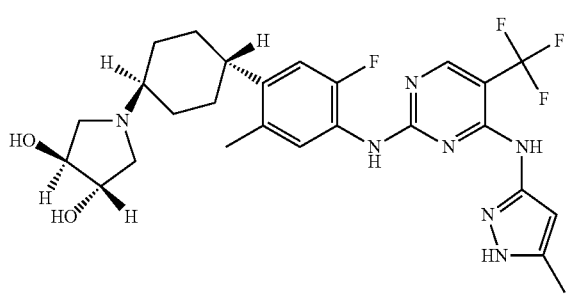 [SMILES: Cc1cc(Nc2nc(Nc3cc(C)c([C@H]4CC[C@H](N5C[C@H](O)[C@@H](O)C5)CC4)cc3F)ncc2C(F)(F)F)n[nH]1]<br>(3S,4S)-1-((trans)-4-(5-fluoro-2-methyl-4-(4-(5-methyl-1H-pyrazol-3-ylamino)-5-(trifluoromethyl)pyrimidin-2-ylamino)phenyl)cyclohexyl)pyrrolidine-3,4-diol | ESMS m/z 550.3 (M + H⁺) | 0.302 |
| 70 | 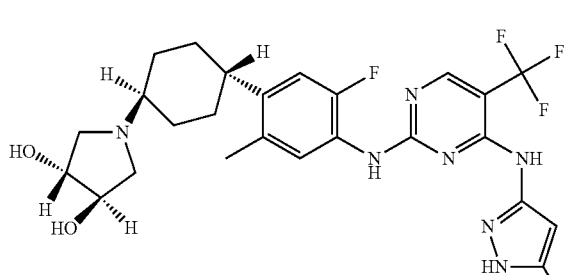<br>(3R,4R)-1-((trans)-4-(5-fluoro-2-methyl-4-(4-(5-methyl-1H-pyrazol-3-ylamino)-5-(trifluoromethyl)pyrimidin-2-ylamino)phenyl)cyclohexyl)pyrrolidine-3,4-diol | ESMS m/z 550.3 (M + H⁺) | 0.248 |

TABLE 1-continued

| | STRUCTURE | NMR or ESMS | IGF1R Ba/F3 IC50 (uM) |
|---|---|---|---|
| 71 | (3R,4R)-1-((cis)-4-(5-fluoro-2-methyl-4-(4-(5-methyl-1H-pyrazol-3-ylamino)-5-(trifluoromethyl)pyrimidin-2-ylamino)phenyl)cyclohexyl)pyrrolidine-3,4-diol | ESMS m/z 550.3 (M + H+) | 0.109 |
| 72 | Trans-4-(4-(5-chloro-4-(5-methyl-1H-pyrazol-3-ylamino)pyrimidin-2-ylamino)-5-fluoro-2-methylphenyl)cyclohexanol | ESMS m/z 431.2 (M + H+) | 0.099 |
| 73 | Cis-4-(4-(5-chloro-4-(5-methyl-1H-pyrazol-3-ylamino)pyrimidin-2-ylamino)-5-fluoro-2-methylphenyl)cyclohexanol | ESMS m/z 431.2 (M + H+) | 0.032 |
| 74 | 5-chloro-N2-(2,5-dimethyl-4-(1,2,3,4-tetrahydroisoquinolin-6-yl)phenyl)-N4-(5-methyl-1H-pyrazol-3-yl)pyrimidine-2,4-diamine | ESMS m/z 460.2 (M + H+) | 0.087 |

TABLE 1-continued

| | STRUCTURE | NMR or ESMS | IGF1R Ba/F3 IC50 (uM) |
|---|---|---|---|
| 75 | 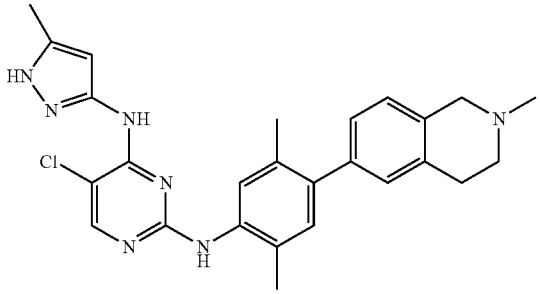 [SMILES: Cc1cc(Nc2nc(Nc3cc(C)c(-c4ccc5c(c4)CCN(C)C5)cc3C)ncc2Cl)n[nH]1]
5-chloro-N2-(2,5-dimethyl-4-(2-methyl-1,2,3,4-tetrahydroisoquinolin-6-yl)phenyl)-N4-(5-methyl-1H-pyrazol-3-yl)pyrimidine-2,4-diamine | ESMS m/z 474.2 (M + H$^+$) | 0.054 |

EXAMPLE 14

6-(5-chloro-4-(5-methyl-1H-pyrazol-3-ylamino)pyrimidin-2-ylamino)-5-fluoro-2-(piperidin-4-yl)isoindolin-1-one (79)

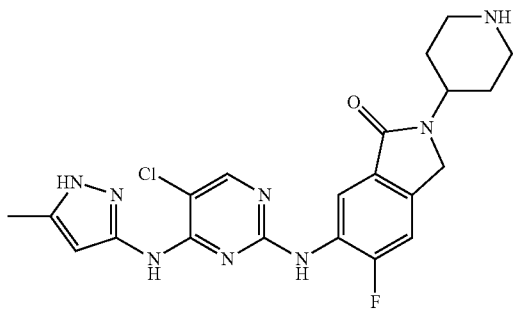 [SMILES: Cc1cc(Nc2nc(Nc3cc4c(cc3F)CN(C3CCNCC3)C4=O)ncc2Cl)n[nH]1]

To the solution of tert-butyl 4-(6-amino-5-fluoro-1-oxoisoindolin-2-yl)piperidine-1-carboxylate (Intermediate 20, 18 mg, 0.05 mmol) and 2,5-dichloro-4-(5-methyl-1H-pyrazol-3-yl)pyrimidine (12 mg, 0.05 mmol) in 1 mL of i-PrOH was added 5 drops of conc. aqueous HCl. The reaction mixture was heated at 150° C. in a microwave reactor for 20 min, followed by concentration and purification with preparative RP-HPLC to afford 6-(5-chloro-4-(5-methyl-1H-pyrazol-3-ylamino)pyrimidin-2-ylamino)-5-fluoro-2-(piperidin-4-yl)isoindolin-1-one; ESMS m/z 457.2 (M+H$^+$).

EXAMPLE 15

6-(5-chloro-4-(5-methylisoxazol-3-ylamino)pyrimidin-2-ylamino)-5-fluoro-2-(piperidin-4-yl)isoindolin-1-one (80)

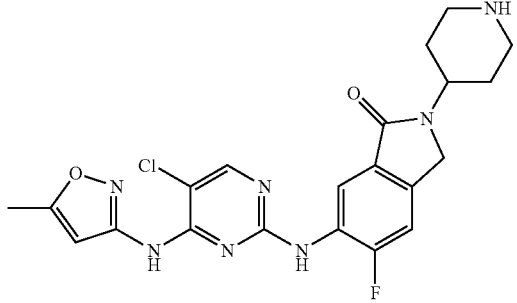 [SMILES: Cc1cc(Nc2nc(Nc3cc4c(cc3F)CN(C3CCNCC3)C4=O)ncc2Cl)no1]

To the solution of tert-butyl 4-(6-amino-5-fluoro-1-oxoisoindolin-2-yl)piperidine-1-carboxylate (35 mg, 0.1 mmol) and 5-chloro-4-(5-methylisoxazol-3-yl)pyrimidin-2-amine (25 mg, 0.1 mmol) in 1 mL of i-PrOH was added 5 drops of conc. aqueous HCl. The reaction mixture was heated at 150° C. in microwave reactor for 20 min, followed by concentration and purification with preparative RP-HPLC to afford 6-(5-chloro-4-(5-methylisoxazol-3-ylamino)pyrimidin-2-ylamino)-5-fluoro-2-(piperidin-4-yl)isoindolin-1-one; ESMS m/z 458.1 (M+H$^+$).

EXAMPLE 16

2-(4-(6-(5-Chloro-4-(5-methyl-1H-pyrazol-3-ylamino)pyrimidin-2-ylamino)-4-methylpyridin-3-yl)piperidin-1-yl)acetamide (84)

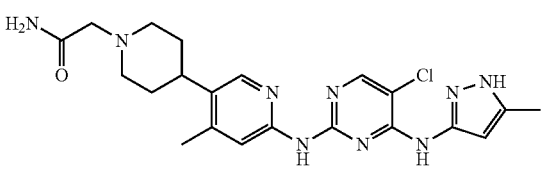 [SMILES: Cc1cc(Nc2nc(Nc3cc(C)c(C4CCN(CC(N)=O)CC4)cn3)ncc2Cl)n[nH]1]

Step 1: To a mixture of 5-bromo-4-methylpyridin-2-amine (200 mg, 1.07 mmol), tert-butyl 4-(4,4,5,5-tetramethyl-1,3,2-dioxaborolan-2-yl)-5,6-dihydropyridine-1(2H)-carboxylate (370 mg, 1.2 mmol) and sodium carbonate (400 mg, 1.28 mmol) in DMF/H$_2$O (8/2 mL) was added tetrakis(triphenylphosphine) palladium (0) (62 mg, 5% mmol). The reaction tube is sealed, the mixture was purged with N$_2$ for 3 min and then heated at 100° C. under N$_2$ for overnight. The reaction was cooled to room temperature and poured into saturated aqueous ammonia chloride solution. The crude reaction mixture was extracted with ethyl acetate (3×15 mL). The organic extracts were combined, washed with brine and concentrated. The crude product was purified with silica gel column chromatography (80% ethyl acetate in hexanes) to afford tert-butyl 4-(6-amino-4-methylpyridin-3-yl)-5,6-dihydropyridine-1(2H)-carboxylate as a yellow oil. The obtained oil was dissolved in methanol (20 mL). To the solution was added Pd/C (10% w/w). The reaction mixture was degassed and purged with H$_2$ for several times and then stirred under 1 atm. H₂ overnight. The mixture was filtered and concentrated to afford tert-butyl 4-(6-amino-4-methylpyridin-3-yl)piperidine-1-carboxylate as a yellow solid; ESMS m/z 236 (M−56+H⁺).

Step 2: To a mixture of 2,5-dichloro-N-(5-methyl-1-(tetrahydro-2H-pyran-2-yl)-1H-pyrazol-3-yl)pyrimidin-4-amine (150 mg, 0.45 mmol), tert-butyl 4-(6-amino-4-methylpyridin-3-yl)piperidine-1-carboxylate (120 mg, 0.41 mmol), Xantphos (24 mg, 0.04 mmol) and cesium carbonate (270 mg, 0.82 mmol) in THF (4 mL) was added palladium acetate (5 mg, 0.02 mmol). The mixture was purged with nitrogen and the tube was sealed. The mixture was heated in an oil bath at 100° C. for 5 h. The mixture was filtered and concentrated. The residue was purified with silica chromatography (70% ethyl acetate in hexanes) to afford tert-butyl 4-(6-(5-chloro-4-(5-methyl-1-(tetrahydro-2H-pyran-2-yl)-1H-pyrazol-3-ylamino)pyrimidin-2-ylamino)-4-methylpyridin-3-yl)piperidine-1-carboxylate as a yellow solid; ESMS m/z 583 (M+H⁺).

Step 3: To a solution of tert-butyl 4-(6-(5-chloro-4-(5-methyl-1-(tetrahydro-2H-pyran-2-yl)-1H-pyrazol-3-ylamino)pyrimidin-2-ylamino)-4-methylpyridin-3-yl)piperidine-1-carboxylate in DCM (1 mL), was added TFA (1 mL). The mixture was stirred for 1 h and concentrated to afford 5-chloro-N4-(5-methyl-1H-pyrazol-3-yl)-N2-(4-methyl-5-(piperidin-4-yl)pyridin-2-yl)pyrimidine-2,4-diamine as brownish oil. The product was used directly for subsequent reactions without further purification.

Step 4: To a mixture of 5-chloro-N4-(5-methyl-1H-pyrazol-3-yl)-N2-(4-methyl-5-(piperidin-4-yl)pyridin-2-yl)pyrimidine-2,4-diamine (50 mg, 0.12 mmol) and triethylamine (50 uL, 0.36 mmol) in DMF (1.5 mL), was added 2-bromoacetamide (25 mg, 0.18 mmol). The mixture was stirred at room temperature for 2 hours. The reaction was filtered and the filtrate was purified by RP-HPLC to afford 2-(4-(6-(5-Chloro-4-(5-methyl-1H-pyrazol-3-ylamino)pyrimidin-2-ylamino)-4-methylpyridin-3-yl)piperidin-1-yl)acetamide as a white solid; ¹H NMR (400 MHz, MeOD-d₄) δ 8.30 (s, 1H), 8.21 (s, 1H), 7.28 (s, 1H), 6.19 (s, 1H), 4.0 (s, 2H), 3.80-3.73 (m, 2H), 3.33-3.21 (m, 3H), 2.61 (s, 3H), 2.37 (s, 3H), 2.37-2.32 (m, 2H), 2.20-2.16 (m, 2H); ESMS m/z 456.2 (M+H⁺).

EXAMPLE 17

5-chloro-N⁴-(5-methyl-1H-pyrazol-3-yl)-N²-(4-(piperidin-4-yl)naphthalene-1-yl)pyrimidine-2,4-diamine (85)

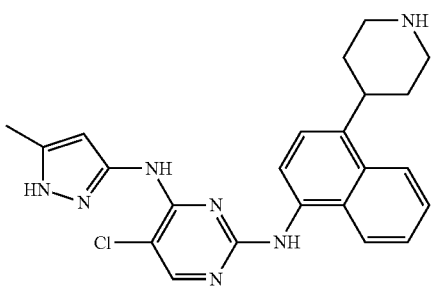 [SMILES: Cc1cc(Nc2nc(Nc3ccc(C4CCNCC4)c4ccccc34)ncc2Cl)n[nH]1]

A mixture of 2,5-dichloro-N-(5-methyl-1-(tetrahydro-2H-pyran-2-yl)-1H-pyrazol-3-yl)pyrimidin-4-amine (202.7 mg, 0.62 mmol), tert-butyl-4-(4-aminonaphthalen-1-yl)piperidine-1-carboxylate (202.0 mg, 0.62 mmol), Xantophos (35.9 mg, 0.062 mmol), padallium acetate (II) (7.0 mg, 0.031 mmol), and cesium carbonate (40.3 mg, 0.12 mmol) in 5.0 mL of THF was heated at 150° C. in a microwave reactor for 25 min. The reaction mixture was filtered and the filtrate was concentrated in vacuo. The crude product was dissolved in 5 mL of DCM and 4 mL of TFA. This reaction mixture was stirred at room temperature for 2 h followed by concentration in vacuo. The crude product is purified by RP-HPLC to afford 5-chloro-N⁴-(5-methyl-1H-pyrazol-3-yl)-N²-(4-(piperidin-4-yl)naphthalene-1-yl)pyrimidine-2,4-diamine; ESMS m/z 434.2 (M+H⁺)

EXAMPLE 18

2-(4-(4-(5-chloro-4-(5-methyl-1H-pyrazol-3-ylamino)pyrimidin-2-ylamino)naphthalene-1-yl)piperidin-1-yl)acetamide (86)

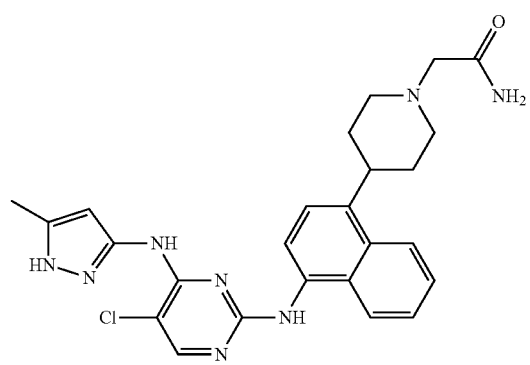 [SMILES: Cc1cc(Nc2nc(Nc3ccc(C4CCN(CC(N)=O)CC4)c4ccccc34)ncc2Cl)n[nH]1]

A mixture of 5-chloro-N⁴-(5-methyl-1H-pyrazol-3-yl)-N²-(4-(piperidin-4-yl)naphthalene-1-yl)pyrimidine-2,4-diamine (30.8 mg, 0.07 mmol), 2-bromoacetamide (19.6 mg, 0.14 mmol) and triethylamine (30.0 µL, 0.21 mmol) in 2 mL of DMF was heated at 130° C. in a microwave reactor for 20 min. The crude product was purified by RP-HPLC to afford 2-(4-(4-(5-chloro-4-(5-methyl-1H-pyrazol-3-ylamino)pyrimidin-2-ylamino)naphthalene-1-yl)piperidin-1-yl)acetamide; ESMS m/z 491.2 (M+H⁺).

EXAMPLE 19

3-(4-(4-(5-chloro-4-(5-methyl-1H-pyrazol-3-ylamino)pyrimidin-2-ylamino)naphthalen-1-yl)piperidin-1-yl)-1,1,1-trifluoropropan-2-ol (88)

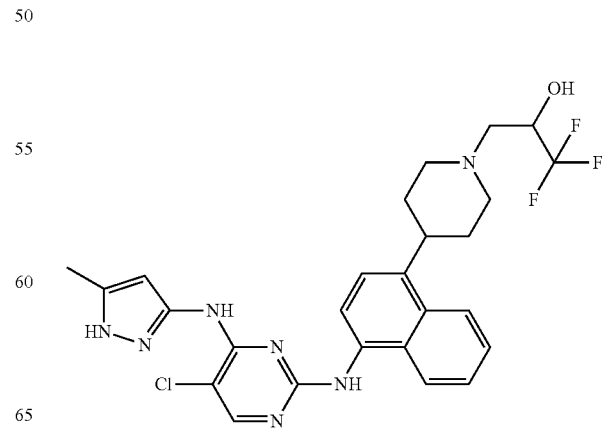

A mixture of 5-chloro-N⁴-(5-methyl-1H-pyrazol-3-yl)-N²-(4-(piperidin-4-yl)naphthalene-1-yl)pyrimidine-2,4-diamine (30.8 mg, 0.07 mmol) and 2-(trifluoromethyl)oxirane (39.2 mg, 0.35 mmol) in 1 mL of DMF was stirred at room temperature overnight. The crude mixture was purified by RP-HPLC to give 3-(4-(4-(5-chloro-4-(5-methyl-1H-pyrazol-3-ylamino)pyrimidin-2-ylamino)naphthalen-1-yl)piperidin-1-yl)-1,1,1-trifluoropropan-2-ol; ESMS m/z 546.2 (M+H⁺).

The following compounds in Table 2 are obtained by repeating the procedures described in examples above and using appropriate starting materials.

TABLE 2

| | STRUCTURE | NMR or ESMS | IGF1R Ba/F3 IC50 (uM) |
|---|---|---|---|
| 76 | 2-(4-(6-(5-chloro-4-(5-methyl-1H-pyrazol-3-ylamino)pyrimidin-2-ylamino)-2-methylpyridin-3-yl)piperidin-1-yl)acetamide | ESMS m/z 456.2 (M + H⁺). | 1.79 |
| 77 | 2-(4-(8-(5-chloro-4-(5-methyl-1H-pyrazol-3-ylamino)pyrimidin-2-ylamino)isoquinolin-5-yl)piperidin-1-yl)acetamide | ESMS m/z 492.2 (M + H⁺). | 3.3 |
| 78 | 5-chloro-N4-(5-methyl-1H-pyrazol-3-yl)-N2-(5-(1-(2-(methylsulfonyl)ethyl)piperidin-4-yl)quinolin-8-yl)pyrimidine-2,4-diamine | ESMS m/z 541.2 (M + H⁺). | 0.412 |

TABLE 2-continued

| | STRUCTURE | NMR or ESMS | IGF1R Ba/F3 IC50 (uM) |
|---|---|---|---|
| 79 | 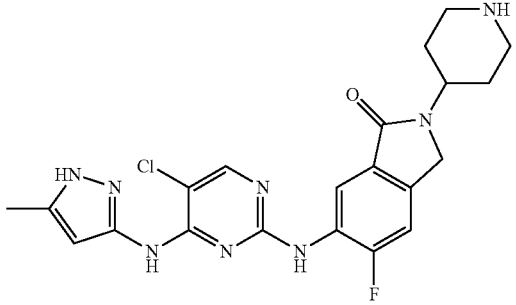 [SMILES: Cc1cc(Nc2nc(Nc3cc4c(cc3F)CN(C3CCNCC3)C4=O)ncc2Cl)n[nH]1]<br>6-(5-chloro-4-(5-methyl-1H-pyrazol-3-ylamino)pyrimidin-2-ylamino)-5-fluoro-2-(piperidin-4-yl)isoindolin-1-one | ESMS m/z 457.2 (M + H$^+$). | 6.4 |
| 80 | 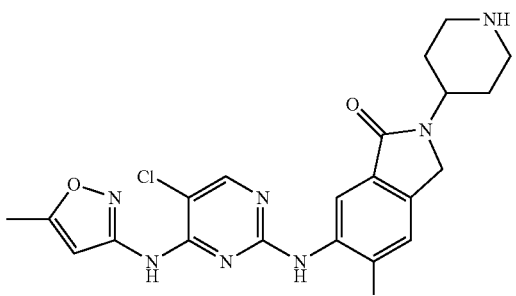<br>6-(5-chloro-4-(5-methylisoxazol-3-ylamino)pyrimidin-2-ylamino)-5-fluoro-2-(piperidin-4-yl)isoindolin-1-one | ESMS m/z 458.1 (M + H$^+$). | 2.65 |
| 81 | 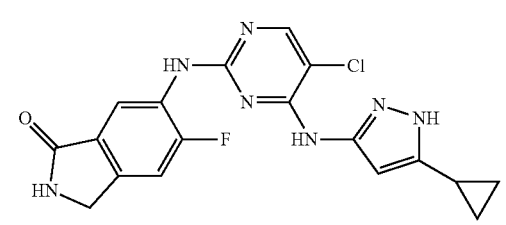 [SMILES: O=C1NCc2cc(F)c(Nc3ncc(Cl)c(Nc4cc(C5CC5)[nH]n4)n3)cc21]<br>6-(5-chloro-4-(5-cyclopropyl-1H-pyrazol-3-ylamino)pyrimidin-2-ylamino)-5-fluoroisoindolin-1-one | ESMS m/z 400.1 (M + H$^+$). | 2.30 |
| 82 | 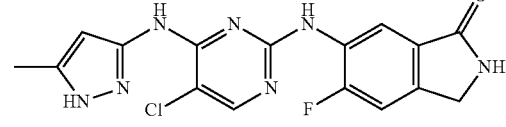<br>6-(5-chloro-4-(5-methyl-1H-pyrazol-3-ylamino)pyrimidin-2-ylamino)-5-fluoroisoindolin-1-one | ESMS m/z 374.1 (M + H$^+$). | 2.63 |
| 83 | 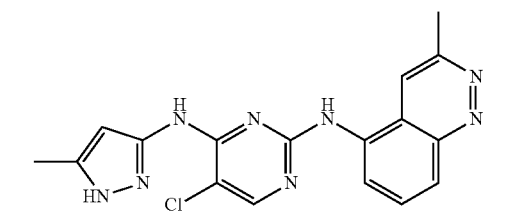 [SMILES: Cc1cc2c(Nc3ncc(Cl)c(Nc4cc(C)[nH]n4)n3)cccc2nn1]<br>5-chloro-N4-(5-methyl-1H-pyrazol-3-yl)-N2-(3-methylcinnolin-5-yl)pyrimidine-2,4-diamine | ESMS m/z 367.1 (M + H$^+$). | 1.45 |

TABLE 2-continued

| | STRUCTURE | NMR or ESMS | IGF1R Ba/F3 IC50 (uM) |
|---|---|---|---|
| 84 | 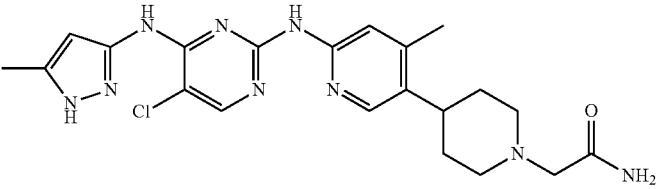 [SMILES: Cc1cc(Nc2nc(Nc3cc(C)c(C4CCN(CC(N)=O)CC4)cn3)ncc2Cl)n[nH]1]<br>2-(4-(6-(5-chloro-4-(5-methyl-1H-pyrazol-3-ylamino)pyrimidin-2-ylamino)-4-methylpyridin-3-yl)piperidin-1-yl)acetamide | ESMS m/z 456.2 (M + H⁺). | 0.525 |
| 85 | 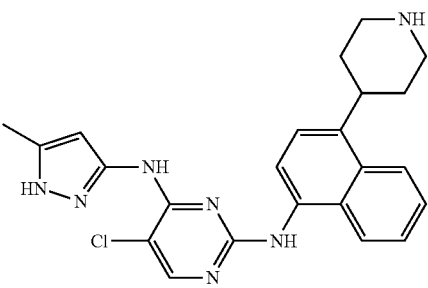 [SMILES: Cc1cc(Nc2nc(Nc3ccc(C4CCNCC4)c4ccccc34)ncc2Cl)n[nH]1]<br>5-chloro-N4-(5-methyl-1H-pyrazol-3-yl)-N2-(4-(piperidin-4-yl)naphthalen-1-yl)pyrimidine-2,4-diamine | ESMS m/z 434.2 (M + H⁺) | 0.493 |
| 86 | 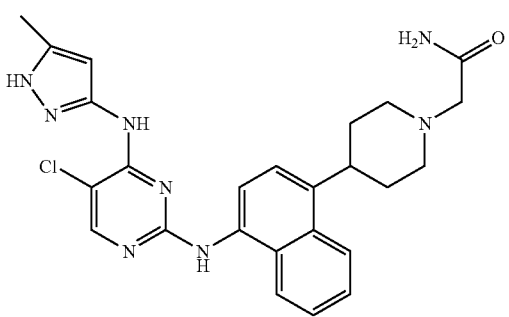 [SMILES: Cc1cc(Nc2nc(Nc3ccc(C4CCN(CC(N)=O)CC4)c4ccccc34)ncc2Cl)n[nH]1]<br>2-(4-(4-(5-chloro-4-(5-methyl-1H-pyrazol-3-ylamino)pyrimidin-2-ylamino)naphthalen-1-yl)piperidin-1-yl)acetamide | ESMS m/z 491.2 (M + H⁺) | 0.107 |
| 87 | 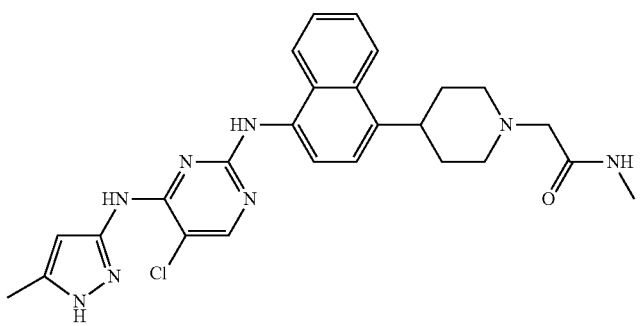<br>2-(4-(4-(5-chloro-4-(5-methyl-1H-pyrazol-3-ylamino)pyrimidin-2-ylamino)naphthalen-1-yl)piperidin-1-yl)-N-methylacetamide | ESMS m/z 505.2 (M + H⁺) | 0.082 |

TABLE 2-continued

| | STRUCTURE | NMR or ESMS | IGF1R Ba/F3 IC50 (uM) |
|---|---|---|---|
| 88 | 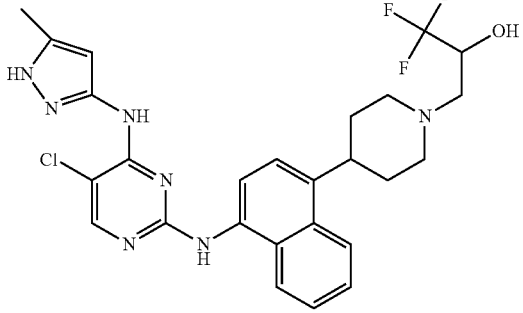 3-(4-(4-(5-chloro-4-(5-methyl-1H-pyrazol-3-ylamino)pyrimidin-2-ylamino)naphthalen-1-yl)piperidin-1-yl)-1,1,1-trifluoropropan-2-ol | ESMS m/z 546.2 (M + H$^+$) | 0.346 |
| 89 | 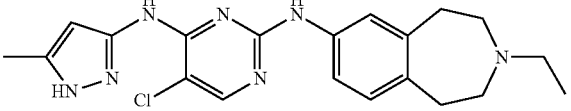 5-chloro-N2-(3-ethyl-2,3,4,5-tetrahydro-1H-benzo[diazepin-7-yl)-N4-(5-methyl-1H-pyrazol-3-yl)pyrimidine-2,4-diamine | ESMS m/z 398.2 (M + H$^+$) | 0.088 |

Assays

The IC$_{50}$ of a drug may be determined constructing a dose-response curve and examining the effect of different concentrations of antagonist on reversing agonist activity. IC$_{50}$ values may be calculated for a given antagonist by determining the concentration needed to inhibit half of the maximum biological response of the agonist. To calculate IC$_{50}$ values, a series of dose-response data (e.g., drug concentrations x1, x2, . . . , xn and growth inhibition y1, y2, . . . , yn, the values of y are in the range of 0-1) is generated. IC$_{50}$ values may be determined by a computer-aided system using the formula:

$$y = D + ((A-D)/(1+10^{(x-\log(IC50)B)}))$$

where A is the ratio of growth inhibition between lowest drug concentration and control; B is the slope of sigmoidal curvel; and D is the ratio of growth inhibition between highest drug concentration and control.

The IC$_{50}$ value is given as that concentration of the test compound that results in growth inhibition that is 50% lower than that obtained using the control without inhibitor. The compounds of the invention in free form or in pharmaceutically acceptable salt form may exhibit valuable pharmacological properties, for example, as indicated by the in vitro tests described in this application. In general, compounds of the invention have IC$_{50}$ values from 1 nM to 10 µM. In some examples, compounds of the invention have IC$_{50}$ values from 0.01 µM to 5 µM. In other examples, compounds of the invention have IC$_{50}$ values from 0.01 µM to 1 µM, or more particularly from 1 nM to 1 µM. In yet other examples, compounds of the invention have IC$_{50}$ values of less than 1 nM or more than 10 µM. The compounds of the invention may exhibit a percentage inhibition of greater than 50%, or in other embodiments, may exhibit a percentage inhibition greater than about 70%, against IGF-1R at 10 µM.

Ba/F3 Cell Line Panel and Reagents

Ba/F3 is a murine IL-3-dependent pro-B lymphoma cell line. Parental Ba/F3 cells are used to generate a panel of sublines whose proliferation and survival is rendered IL-3-independent by stable transduction with individual tyrosine kinases activated by fusion with the amino-terminal portion of TEL (amino acid 1-375) or BCR. In order to generate Ba/F3 cell lines transformed by Tel-Tyrosine Kinase (TK) fusions, parental Ba/F3 cells are infected with a retrovirus harboring each TEL-fusion kinase and subjected to puromycin selection and IL-3 withdrawal to obtain IL-3-independent, transformed Ba/F3 cells.

Each transformed Ba/F3 cells are cultured in RPMI-1640 media (Gibco Cat #11875093, Carlsbad, Calif.) supplemented with 10% FBS (Hyclone Cat #SV30014.03, Logan, Utah), 4.5 g/L glucose (Sigma #G5400, St.Louis, Mo.), 1.5 g/L sodium bicarbonate (Biowhittaker #17-613E, Walkersville, Md.) and Pen/Strep (Gibco #10378-016, Carlsbad, Calif.). Cells are splitted twice weekly.

Ba/F3 Cell Viability Inhibition Assay

The potency of test compounds against various Tel-TK transformed Ba/F3 lines is determined as follows. Exponentially growing BaF3 Tel-TK cells are diluted in fresh medium to 75,000 cells/mL and seeded into 384-well plates (3750 cells/well) at 50 µL/well using a gill liquid dispenser (BioTek, Winooski, Vt., USA). Duplicate plates are run for each cell line. Test and control compounds are serially diluted with DMSO and arrayed in a polypropylene 384-well plate. 50 nL of compound is transferred into the assay plates using a pin-transfer device, and the plates are incubated at 37° C. (5% CO$_2$) for 48 hours. 25 µL Britelite (Perkin Elmer) is added and luminescence is quantified using Analyst GT (Molecular Devices). Custom curve-fitting software is used to produce a logistic fit of percent cell viability as a function of the logarithm of inhibitor concentration. The IC$_{50}$ is interpolated as the concentration of compound needed to reduce cell viability to 50% of a DMSO control. Parental Ba/F3 cells that are maintained and cultured in presence of IL-3 (1 ng/ml in final) are diluted in fresh medium containing IL-3 (1 ng/ml in final) to 75,000 cells/mL following the same procedure as described above.

Enzymatic HTRF Assay

IGF-1R and INSR (insulin receptor) are purchased from Upstate. Following reagents are prepared in-house; 10× kinase buffer (KB) (200 mM Tris (pH 7.0), 100 mM MgCl$_2$, 30 mM MnCl$_2$, 50 nM NaVO$_4$), 10 mM ATP, 100 mg/ml BSA, 0.5 M EDTA, 4 M KF. Proxiplate-384 from Perkin-Elmer is used for set up assay. All the HTRF reagents including substrate (Biotin-poly-GT (61GT0BLB), Mab PT66-K, (61T66KLB), Streptavidin-XL$^{ent}$ (611SAXLB)) are purchased from CIS-US, Inc.

The substrate/ATP mix is prepared by adding ATP (final concentration, 3 μM) and biotinylated poly-GT (final concentration, 10 ng/μl) into 1× KB, and dispensed into Proxiplate-384 at 5 μl/well using μFill (Bio-TEK). Serially diluted compounds (in DMSO) are transferred into plate using 50 nL pinhead. 5 μL of prepared Enzyme mix (enzyme (final concentration, 5 ng/μl), mixed with BSA and DTT in 1× KB) is added to initiate kinase reaction using μFill (Bio-TEK). Assay plate is incubated at room temperature for 2 hours. Detection mix is prepared by adding both Mab PT66-K and Streptavidin-XL$^{ent}$ into 0.5× KB solution containing KF (final concentration, 125 mM), EDTA (final concentration, 50 mM) and BSA (final concentration, 100 μg/ml) in. At the end of reaction, 10 μL of detection mix is added and incubated for 30 minutes at room temperature before measurement. HTRF signal is detected using Analyst-GT (molecular Devices).

Cancer Cell Proliferation Inhibition Assay

For luciferizing cancer cell line, each cell line is transduced by ampholytic retrovirus carrying both luciferase gene and puromycin-resistant gene whose expression is driven by LTR. Briefly, the retroviral vector pMSCV-Puro-Luc is transfected into Phoenix cell line using Fugene6 (Roche) according to manufacturer's instruction. Two days after transfection, supernatant containing virus is harvested and filtered with 0.2 μm filter. Harvested virus is used immediately or stored at −80'C. For infection, cultured cancer cells are harvested and plated (5×10$^5$ cells/well in 1 ml medium) on 6-well tissue culture plate. For each well, 3 ml virus supernatant is added together with 400 μl FBS, 40 μl 1 M HEPES (pH8.0) and 4 μl of polybrene (10 μg/ml, Specialty media). The plate is centrifuged down for 90 minutes at 2500 rpm for spin-infection and is transferred into an incubator for overnight infection. Next day, infected cell line is transferred into T-75 flask containing fresh medium and incubated for one day. Two days after infection, puromycin is added at the final concentration of 1 μg/ml to begin selection. Within 1-2 weeks, puromycin-resistant cell line is established after at least two subsequent splits and is preserved as luciferized stock.

Each cell line is harvested while in log phase growth by trypsinization and diluted in respective media to appropriate density prior to plating. Cells are dispensed using μFill (BioTeK) at 50 μl/well into white walled clear bottom plates (Greiner—custom for GNF). Cells are then placed in 37° C. incubator supplying 5% CO2 overnight. Compounds are transferred using 50nL/well Pintool technology via Platemate (Matrix). Assay plates are then placed back into the incubator for 3 days. On the third day following compound transfer, BRITELITE® (Perkin Elmer, diluted according to manufacturer's suggestion) is added to assay plates and read on Analyst GT (Molecular Devices) or Envision (Perkin Elmer). Raw data is generated in RLU.

* * *

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A compound of Formula (4) or (5):

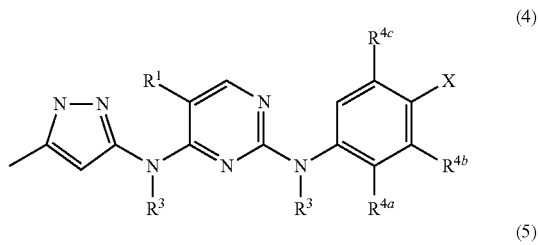

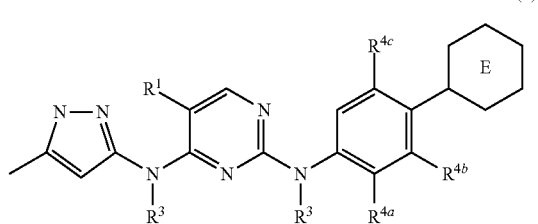

or a physiologically acceptable salt thereof;

wherein R$^1$ is halo, C$_{1-6}$ alkyl, or a halo-substituted C$_{1-6}$ alkyl;

each R$^3$ is H;

one of R$^{4a}$, R$^{4b}$ and R$^{4c}$ is H and the others are independently halo, C$_{1-6}$ alkyl, C$_{1-6}$ alkoxy, halo-substituted C$_{1-6}$ alkyl or halo-substituted C$_{1-6}$ alkoxy;

X is quinolinyl, (1,2,3,4-tetrahydroisoquinolin-6-yl) or a 5-6 membered heteroaryl selected from pyrazolyl, pyridyl, thiophenyl, furanyl, imidazolyl, isoxazolyl, oxazolyl or thiazolyl, each of which is optionally substituted with C$_{1-6}$ alkyl, hydroxyl, or C(O)NRR$^7$ in which R$^7$ is H or C$_{1-6}$ alkyl and R is H or C$_{1-6}$ alkyl;

ring E is a C$_6$ carbocycle optionally substituted with oxo, =N—OH or R$^9$;

R$^9$ is hydroxyl or NRR$^7$ in which R$^7$ is C$_{1-6}$ alkyl or (CR$_2$)$_q$Y, Y is C$_3$ cycloalkyl and R is H or C$_{1-6}$ alkyl, or alternatively, R and R$^7$ together with N in NRR$^7$ of R$^9$ forms morpholinyl, piperidinyl, piperazinyl, (C$_{1-6}$ alkyl)-piperazinyl, or pyrrolidinyl, each of which is optionally substituted with hydroxyl; and q is 0-4.

2. The compound of claim 1, wherein R$^{4b}$ is H.

3. The compound of claim 1, wherein R$^{4a}$ and R$^{4c}$ are independently halo, C$_{1-6}$ alkyl, C$_{1-6}$ alkoxy, halo-substituted C$_{1-6}$ alkyl or halo-substituted C$_{1-6}$ alkoxy.

4. The compound of claim 1, wherein R$^1$ is chloro or a halo-substituted C$_{1-6}$ alkyl.

5. The compound of claim 1, wherein said compound is selected from

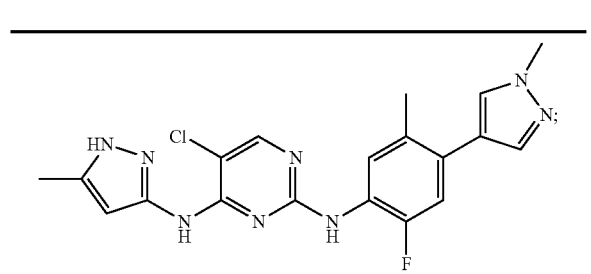

5-chloro-N2-(2-fluoro-5-methyl-4-(1-methyl-1H-pyrazol-4-yl)phenyl)-N4-(5-methyl-1H-pyrazol-3-yl)pyrimidine-2,4-diamine;

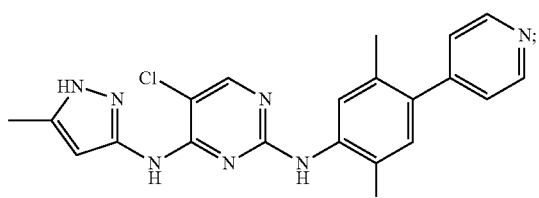

5-chloro-N2-(2-fluoro-5-methyl-4-(pyridin-4-yl)phenyl)-N4-(5-methyl-1H-pyrazol-3-yl)pyrimidine-2,4-diamine;

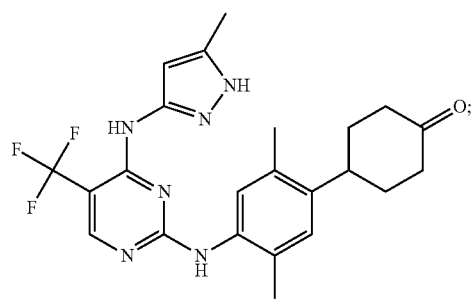 [SMILES: Cc1cc(Nc2nc(Nc3cc(C)c(C4CCC(=O)CC4)cc3C)ncc2C(F)(F)F)n[nH]1]

4-(2,5-dimethyl-4-(4-(5-methyl-1H-pyrazol-3-ylamino)-5-(trifluoromethyl)pyrimidin-2-ylamino)phenyl)cyclohexanone;

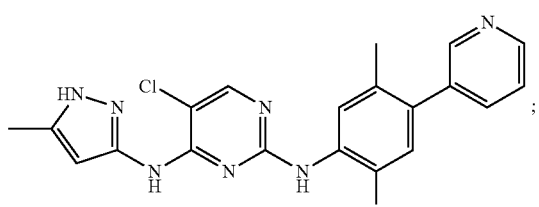

5-chloro-N2-(2-fluoro-5-methyl-4-(pyridin-3-yl)phenyl)-N4-(5-methyl-1H-pyrazol-3-yl)pyrimidine-2,4-diamine;

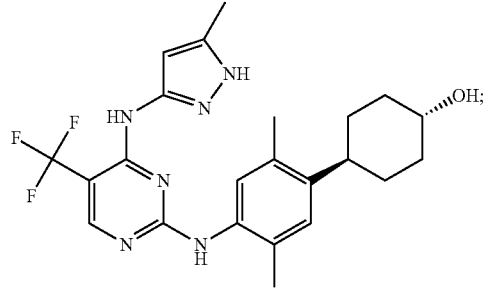 [SMILES: Cc1cc(Nc2nc(Nc3cc(C)c([C@H]4CC[C@H](O)CC4)cc3C)ncc2C(F)(F)F)n[nH]1]

trans-4-(2,5-dimethyl-4-(4-(5-methyl-1H-pyrazol-3-ylamino)-5-(trifluoromethyl)pyrimidin-2-ylamino)phenyl)cyclohexanol;

-continued

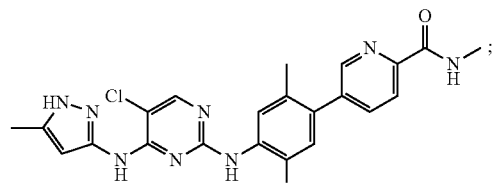

5-(4-(5-chloro-4-(5-methyl-1H-pyrazol-3-ylamino)pyrimidin-2-ylamino)-5-fluoro-2-methylphenyl)-N-methylpicolinamide;

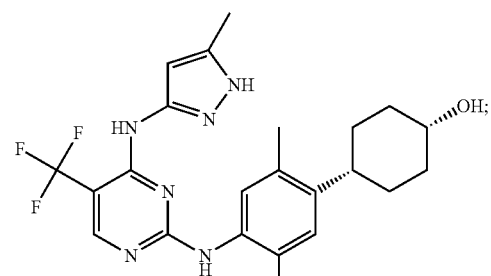

Cis-4-(2,5-dimethyl-4-(4-(5-methyl-1H-pyrazol-3-ylamino)-5-(trifluoromethyl)pyrimidin-2-ylamino)phenyl)cyclohexanol;

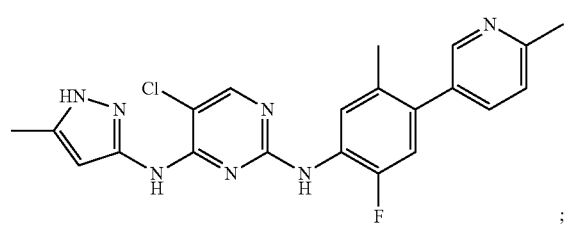

5-chloro-N2-(2-fluoro-5-methyl-4-(6-methylpyridin-3-yl)phenyl)-N4-(5-methyl-1H-pyrazol-3-yl)pyrimidine-2,4-diamine;

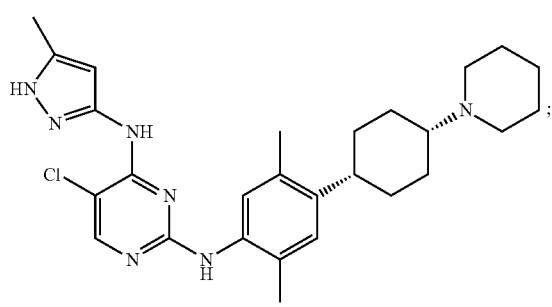 [SMILES: Cc1cc(Nc2nc(Nc3cc(C)c([C@H]4CC[C@@H](N5CCCCC5)CC4)cc3C)ncc2Cl)n[nH]1]

Cis-5-chloro-N2-(2,5-dimethyl-4-(4-(piperidin-1-yl)cyclohexyl)phenyl)-N4-(5-methyl-1H-pyrazol-3-yl)pyrimidine-2,4-diamine;

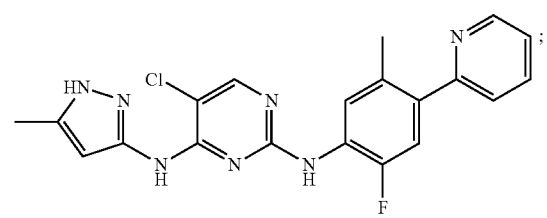 [SMILES: Cc1cc(Nc2nc(Nc3cc(C)c(-c4ccccn4)cc3F)ncc2Cl)n[nH]1]

5-chloro-N2-(2-fluoro-5-methyl-4-(pyridin-2-yl)phenyl)-N4-(5-methyl-1H-pyrazol-3-yl)pyrimidine-2,4-diamine;

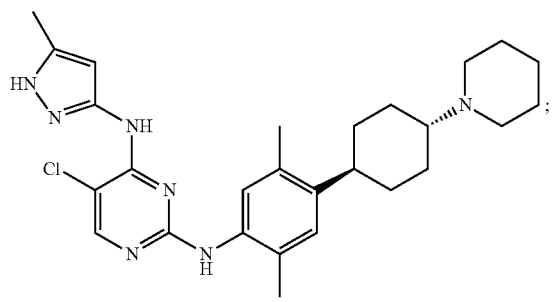

Trans-5-chloro-N2-(2,5-dimethyl-4-(4-(piperidin-1-yl)cyclohexyl)phenyl)-N4-(5-methyl-1H-pyrazol-3-yl)pyrimidine-2,4-diamine;

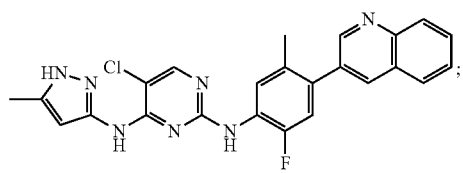 [SMILES: Cc1cc(Nc2nc(Nc3cc(C)c(-c4cnc5ccccc5c4)cc3F)ncc2Cl)n[nH]1]

5-chloro-N2-(2-fluoro-5-methyl-4-(quinolin-3-yl)phenyl)-N4-(5-methyl-1H-pyrazol-3-yl)pyrimidine-2,4-diamine;

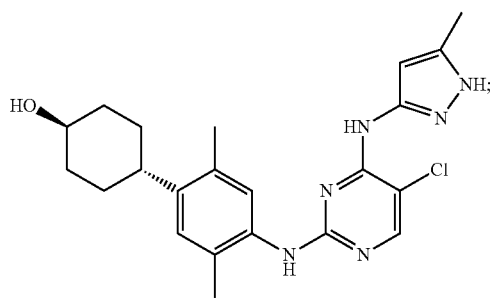 [SMILES: Cc1cc(Nc2nc(Nc3cc(C)c([C@H]4CC[C@H](O)CC4)cc3C)ncc2Cl)n[nH]1]

trans-4-(4-(5-chloro-4-(5-methyl-1H-pyrazol-3-ylamino)pyrimidin-2-ylamino)-2,5-dimethylphenyl)cyclohexanol;

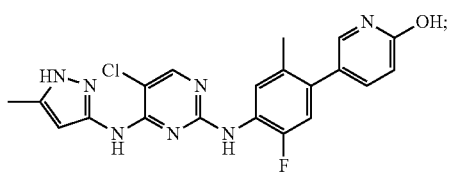 [SMILES: Cc1cc(Nc2nc(Nc3cc(C)c(-c4ccc(O)nc4)cc3F)ncc2Cl)n[nH]1]

5-(4-(5-chloro-4-(5-methyl-1H-pyrazol-3-ylamino)pyrimidin-2-ylamino)-5-fluoro-2-methylphenyl)pyridin-2-ol;

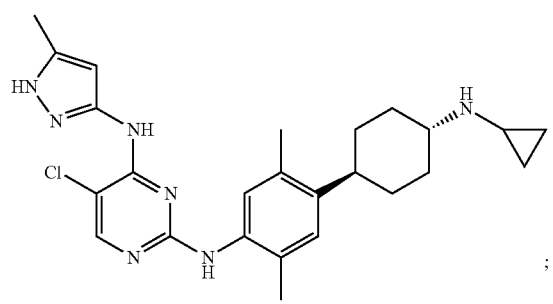 [SMILES: Cc1cc(Nc2nc(Nc3cc(C)c([C@H]4CC[C@H](NC5CC5)CC4)cc3C)ncc2Cl)n[nH]1]

Trans-5-chloro-N2-(4-(4-(cyclopropylamino)cyclohexyl)-2,5-dimethylphenyl)-N4-(5-methyl-1H-pyrazol-3-yl)pyrimidine-2,4-diamine;

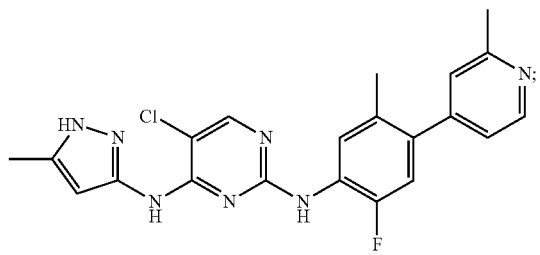 [SMILES: Cc1cc(-c2cc(F)c(Nc3ncc(Cl)c(Nc4cc(C)[nH]n4)n3)cc2C)ccn1]

5-chloro-N2-(2-fluoro-5-methyl-4-(2-methylpyridin-4-yl)phenyl)-N4-(5-methyl-1H-pyrazol-3-yl)pyrimidine-2,4-diamine;

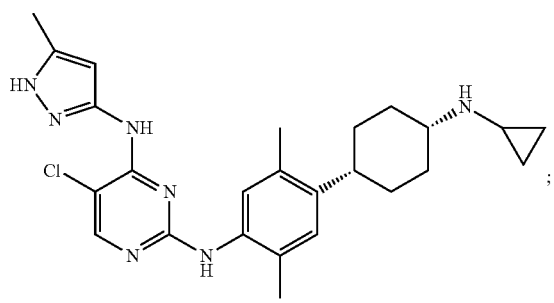 [SMILES: Cc1cc(Nc2nc(Nc3cc(C)c([C@H]4CC[C@@H](NC5CC5)CC4)cc3C)ncc2Cl)n[nH]1]

Cis-5-chloro-N2-(4-(4-(cyclopropylamino)cyclohexyl)-2,5-dimethylphenyl)-N4-(5-methyl-1H-pyrazol-3-yl)pyrimidine-2,4-diamine;

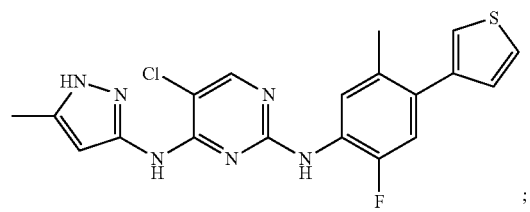 [SMILES: Cc1cc(Nc2nc(Nc3cc(C)c(-c4ccsc4)cc3F)ncc2Cl)n[nH]1]

5-chloro-N2-(2-fluoro-5-methyl-4-(thiophen-3-yl)phenyl)-N4-(5-methyl-1H-pyrazol-3-yl)pyrimidine-2,4-diamine;

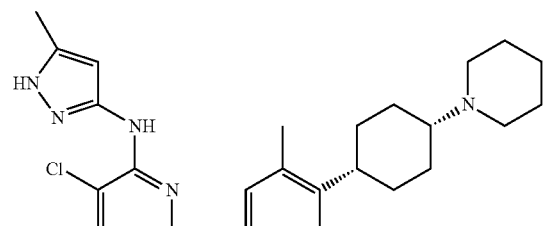

Cis-5-chloro-N2-(2-fluoro-5-methyl-4-(4-(piperidin-1-yl)cyclohexyl)phenyl)-N4-(5-methyl-1H-pyrazol-3-yl)pyrimidine-2,4-diamine;

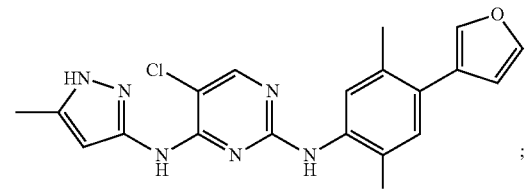

5-chloro-N2-(2-fluoro-4-(furan-3-yl)-5-methylphenyl)-N4-(5-methyl-1H-pyrazol-3-yl)pyrimidine-2,4-diamine;

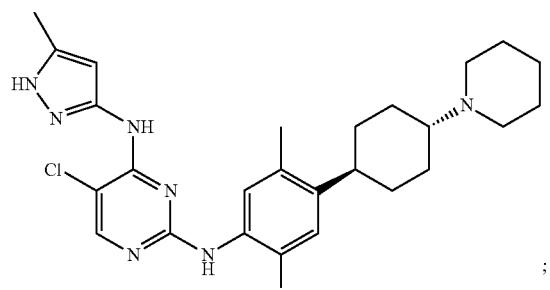

Trans-5-chloro-N2-(2-fluoro-5-methyl-4-(4-(piperidin-1-yl)cyclohexyl)phenyl)-N4-(5-methyl-1H-pyrazol-3-yl)pyrimidine-2,4-diamine;

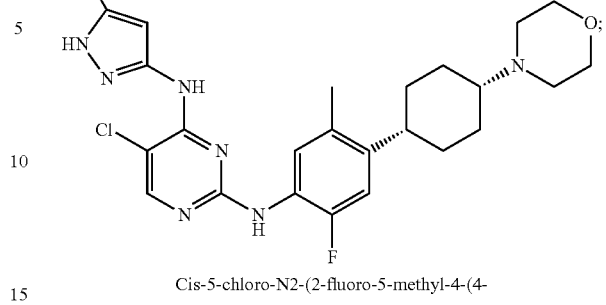

Cis-5-chloro-N2-(2-fluoro-5-methyl-4-(4-morpholinocyclohexyl)phenyl)-N4-(5-methyl-1H-pyrazol-3-yl)pyrimidine-2,4-diamine;

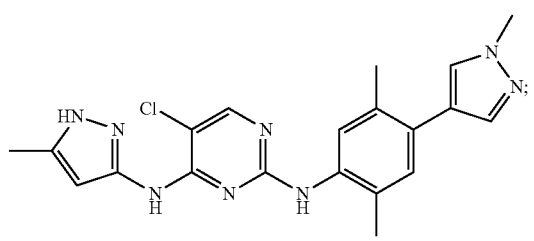 [SMILES: Cc1cc(Nc2nc(Nc3cc(C)c(-c4cnn(C)c4)cc3C)ncc2Cl)n[nH]1]

5-chloro-N2-(2,5-dimethyl-4-(1-methyl-1H-pyrazol-4-yl)phenyl)-N4-(5-methyl-1H-pyrazol-3-yl)pyrimidine-2,4-diamine;

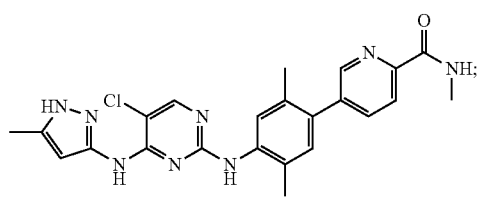

5-(4-(5-chloro-4-(5-methyl-1H-pyrazol-3-ylamino)pyrimidin-2-ylamino)-2,5-dimethylphenyl)-N-methylpicolinamide;

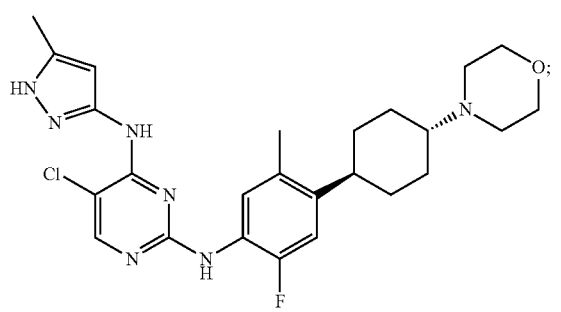 [SMILES: Cc1cc(Nc2nc(Nc3cc(C)c([C@H]4CC[C@H](N5CCOCC5)CC4)cc3F)ncc2Cl)n[nH]1]

Trans-5-chloro-N2-(2-fluoro-5-methyl-4-(4-morpholinocyclohexyl)phenyl)-N4-(5-methyl-1H-pyrazol-3-yl)pyrimidine-2,4-diamine;

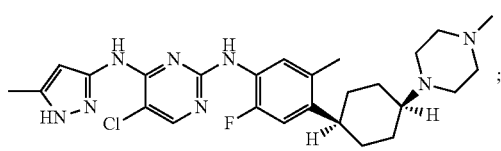

Cis-5-chloro-N2-(2-fluoro-5-methyl-4-(4-(4-methylpiperazin-1-yl)cyclohexyl)phenyl)-N4-(5-methyl-1H-pyrazol-3-yl)pyrimidine-2,4-diamine;

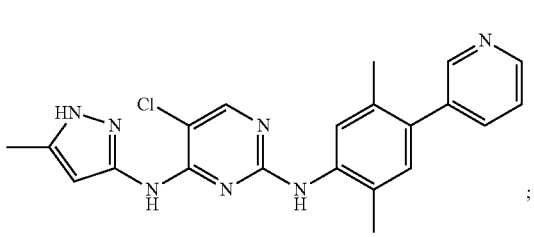 [SMILES: Cc1cc(Nc2nc(Nc3cc(C)c(-c4cccnc4)cc3C)ncc2Cl)n[nH]1]

5-chloro-N2-(2-fluoro-4-(furan-3-yl)-5-methylphenyl)-N4-(5-methyl-1H-pyrazol-3-yl)pyrimidine-2,4-diamine;

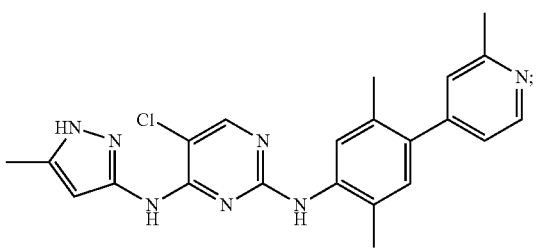 [SMILES: Cc1cc(-c2cc(C)c(Nc3ncc(Cl)c(Nc4cc(C)[nH]n4)n3)cc2C)ccn1]

5-chloro-N2-(2,5-dimethyl-4-(2-methylpyridin-4-yl)phenyl)-N4-(5-methyl-1H-pyrazol-3-yl)pyrimidine-2,4-diamine;

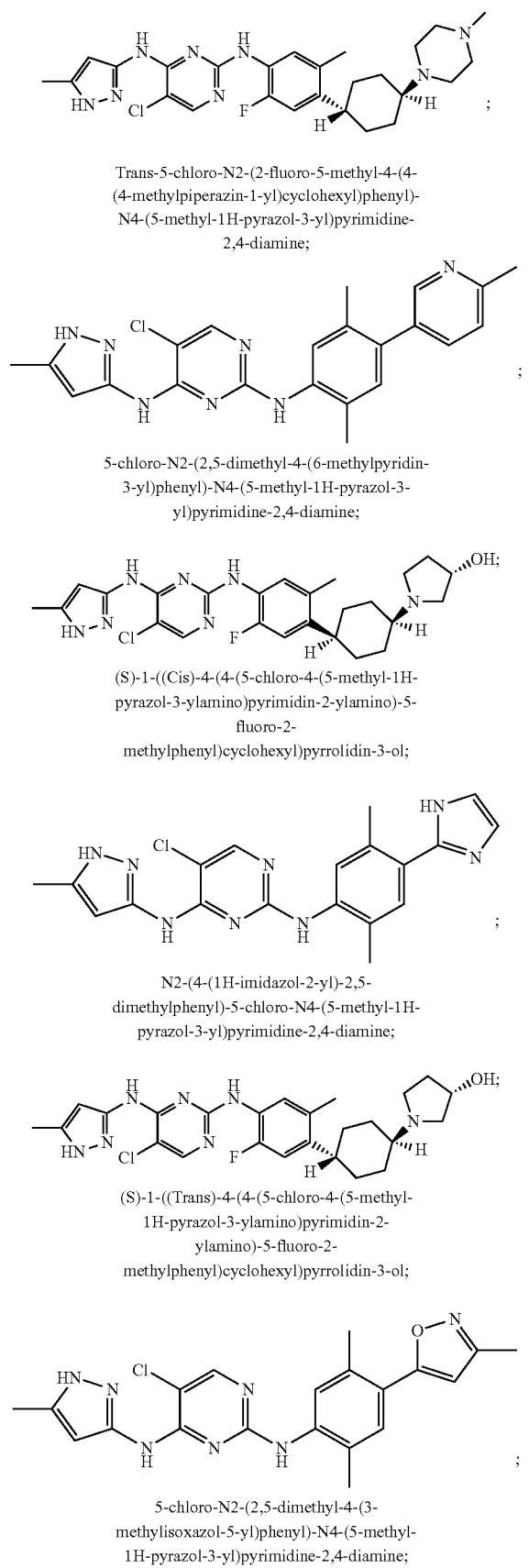

Trans-5-chloro-N2-(2-fluoro-5-methyl-4-(4-(4-methylpiperazin-1-yl)cyclohexyl)phenyl)-N4-(5-methyl-1H-pyrazol-3-yl)pyrimidine-2,4-diamine;

5-chloro-N2-(2,5-dimethyl-4-(6-methylpyridin-3-yl)phenyl)-N4-(5-methyl-1H-pyrazol-3-yl)pyrimidine-2,4-diamine;

(S)-1-((Cis)-4-(4-(5-chloro-4-(5-methyl-1H-pyrazol-3-ylamino)pyrimidin-2-ylamino)-5-fluoro-2-methylphenyl)cyclohexyl)pyrrolidin-3-ol;

N2-(4-(1H-imidazol-2-yl)-2,5-dimethylphenyl)-5-chloro-N4-(5-methyl-1H-pyrazol-3-yl)pyrimidine-2,4-diamine;

(S)-1-((Trans)-4-(4-(5-chloro-4-(5-methyl-1H-pyrazol-3-ylamino)pyrimidin-2-ylamino)-5-fluoro-2-methylphenyl)cyclohexyl)pyrrolidin-3-ol;

5-chloro-N2-(2,5-dimethyl-4-(3-methylisoxazol-5-yl)phenyl)-N4-(5-methyl-1H-pyrazol-3-yl)pyrimidine-2,4-diamine;

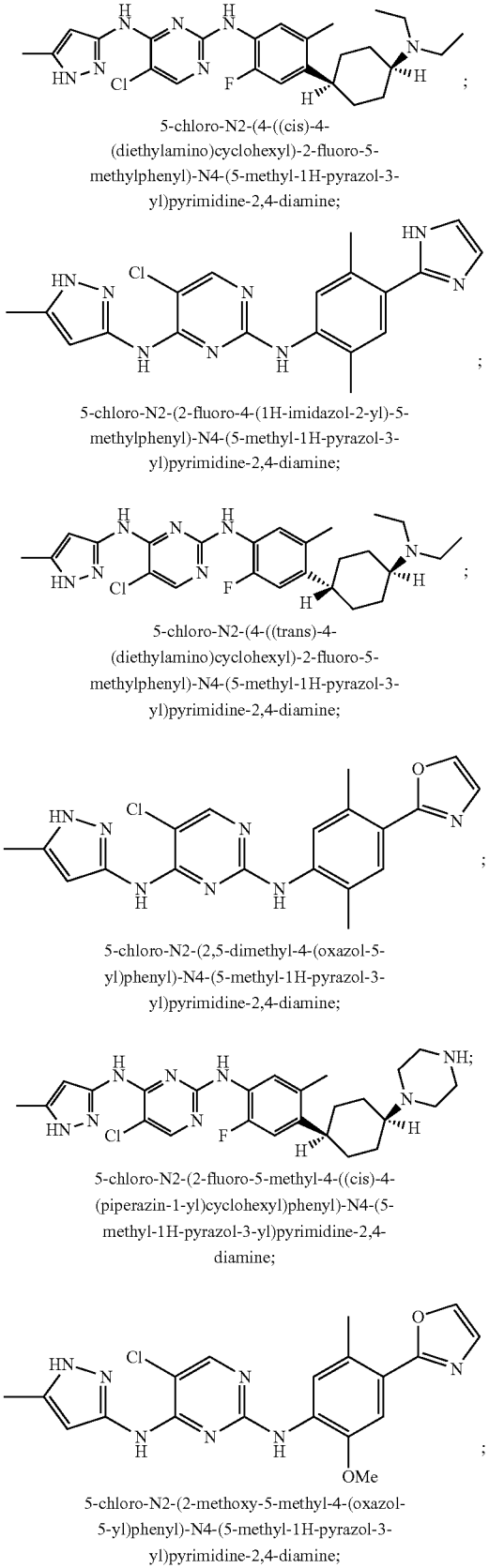

5-chloro-N2-(4-((cis)-4-(diethylamino)cyclohexyl)-2-fluoro-5-methylphenyl)-N4-(5-methyl-1H-pyrazol-3-yl)pyrimidine-2,4-diamine;

5-chloro-N2-(2-fluoro-4-(1H-imidazol-2-yl)-5-methylphenyl)-N4-(5-methyl-1H-pyrazol-3-yl)pyrimidine-2,4-diamine;

5-chloro-N2-(4-((trans)-4-(diethylamino)cyclohexyl)-2-fluoro-5-methylphenyl)-N4-(5-methyl-1H-pyrazol-3-yl)pyrimidine-2,4-diamine;

5-chloro-N2-(2,5-dimethyl-4-(oxazol-5-yl)phenyl)-N4-(5-methyl-1H-pyrazol-3-yl)pyrimidine-2,4-diamine;

5-chloro-N2-(2-fluoro-5-methyl-4-((cis)-4-(piperazin-1-yl)cyclohexyl)phenyl)-N4-(5-methyl-1H-pyrazol-3-yl)pyrimidine-2,4-diamine;

5-chloro-N2-(2-methoxy-5-methyl-4-(oxazol-5-yl)phenyl)-N4-(5-methyl-1H-pyrazol-3-yl)pyrimidine-2,4-diamine;

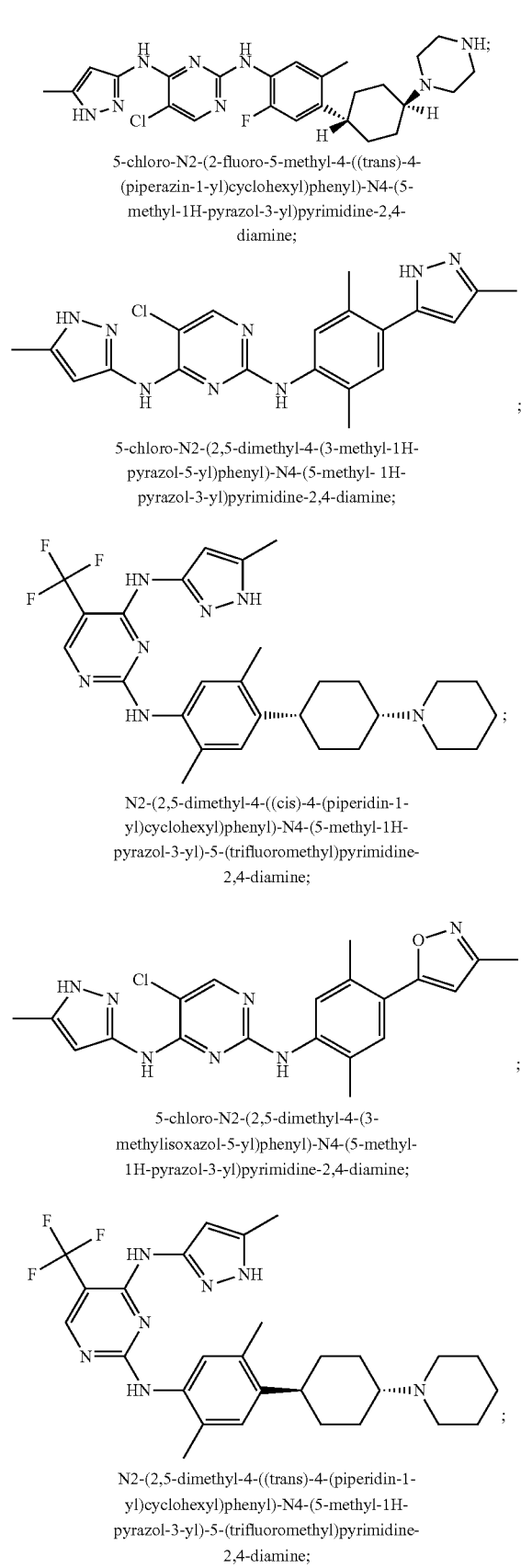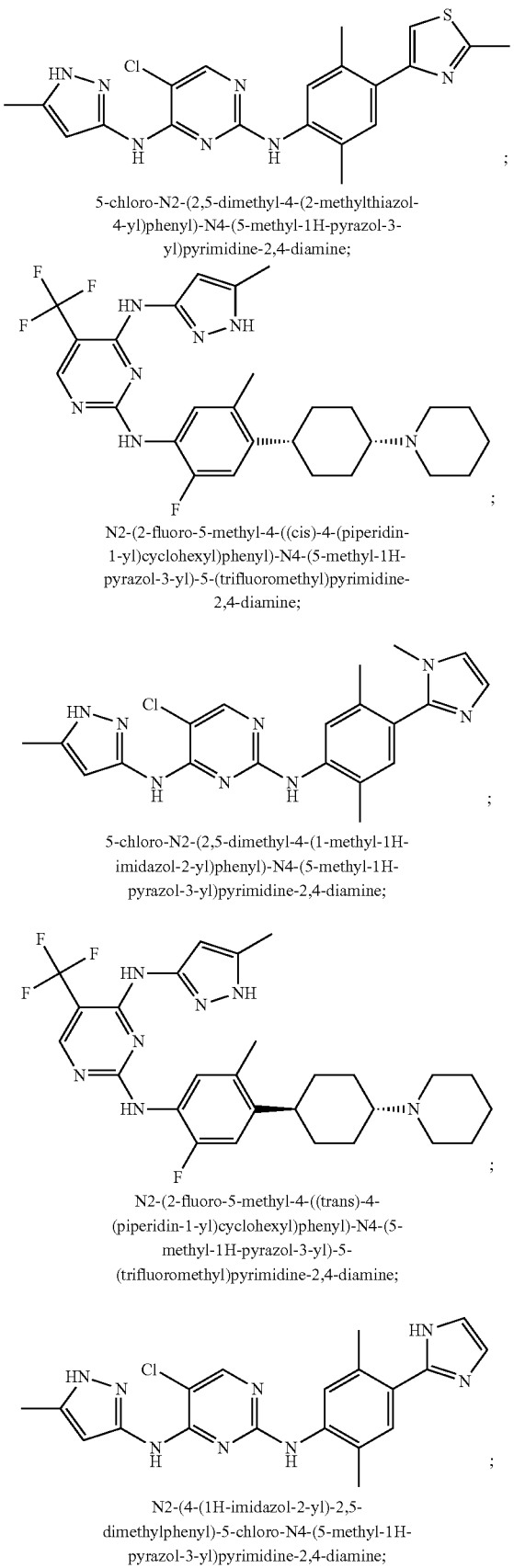

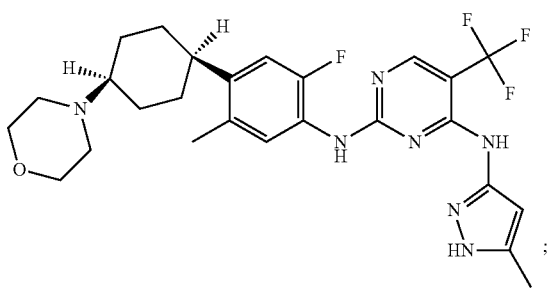 [SMILES: Cc1cc(Nc2nc(Nc3cc(C)c([C@H]4CC[C@@H](N5CCOCC5)CC4)cc3F)ncc2C(F)(F)F)n[nH]1]

N2-(2-fluoro-5-methyl-4-((cis)-4-morpholinocyclohexyl)phenyl)-N4-(5-methyl-1H-pyrazol-3-yl)-5-(trifluoromethyl)pyrimidine-2,4-diamine;

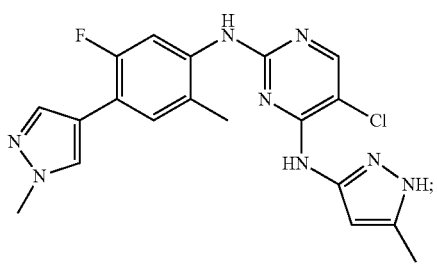 [SMILES: Cc1cc(Nc2nc(Nc3cc(F)c(-c4cnn(C)c4)cc3C)ncc2Cl)n[nH]1]

5-chloro-N2-(5-fluoro-2-methyl-4-(1-methyl-1H-pyrazol-4-yl)phenyl)-N4-(5-methyl-1H-pyrazol-3-yl)pyrimidine-2,4-diamine;

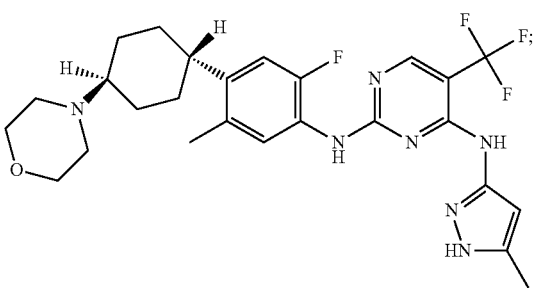 [SMILES: Cc1cc(Nc2nc(Nc3cc(C)c([C@H]4CC[C@H](N5CCOCC5)CC4)cc3F)ncc2C(F)(F)F)n[nH]1]

N2-(2-fluoro-5-methyl-4-((trans)-4-morpholinocyclohexyl)phenyl)-N4-(5-methyl-1H-pyrazol-3-yl)-5-(trifluoromethyl)pyrimidine-2,4-diamine;

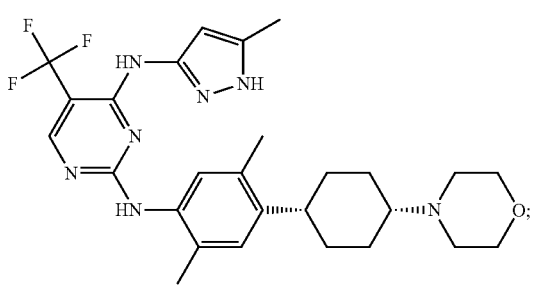 [SMILES: Cc1cc(Nc2nc(Nc3cc(C)c([C@H]4CC[C@@H](N5CCOCC5)CC4)cc3C)ncc2C(F)(F)F)n[nH]1]

N2-(2,5-dimethyl-4-((cis)-4-morpholinocyclohexyl)phenyl)-N4-(5-methyl-1H-pyrazol-3-yl)-5-(trifluoromethyl)pyrimidine-2,4-diamine;

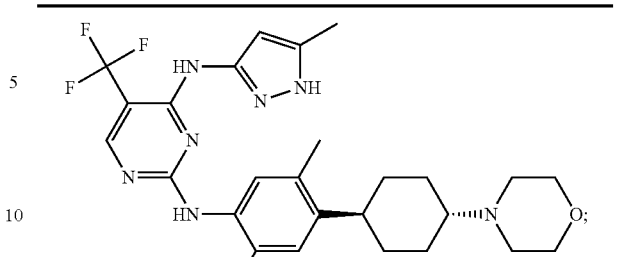

N2-(2,5-dimethyl-4-((trans)-4-morpholinocyclohexyl)phenyl)-N4-(5-methyl-1H-pyrazol-3-yl)-5-(trifluoromethyl)pyrimidine-2,4-diamine;

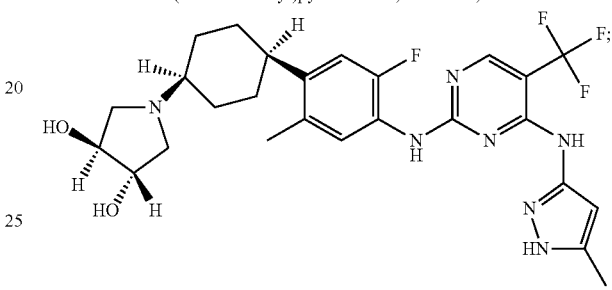

(3S,4S)-1-((cis)-4-(5-fluoro-2-methyl-4-(4-(5-methyl-1H-pyrazol-3-ylamino)-5-(trifluoromethyl)pyrimidin-2-ylamino)phenyl)cyclohexyl)pyrrolidine-3,4-diol;

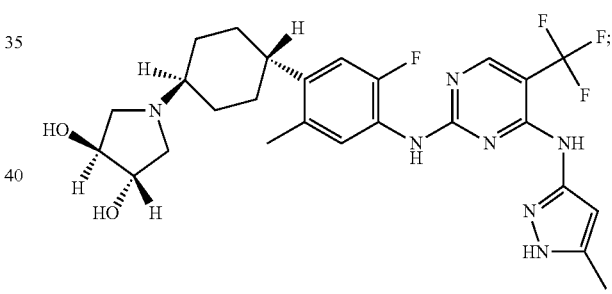

(3S,4S)-1-((trans)-4-(5-fluoro-2-methyl-4-(4-(5-methyl-1H-pyrazol-3-ylamino)-5-(trifluoromethyl)pyrimidin-2-ylamino)phenyl)cyclohexyl)pyrrolidine-3,4-diol;

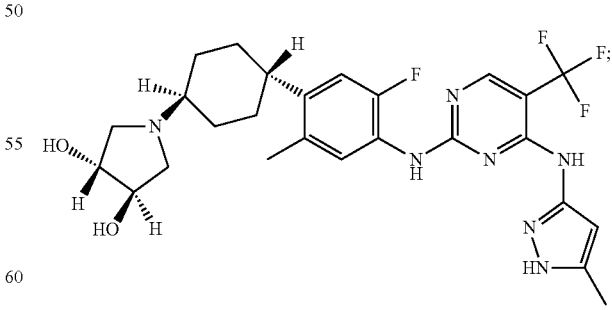

(3R,4R)-1-((trans)-4-(5-fluoro-2-methyl-4-(4-(5-methyl-1H-pyrazol-3-ylamino)-5-(trifluoromethyl)pyrimidin-2-ylamino)phenyl)cyclohexyl)pyrrolidine-3,4-diol;

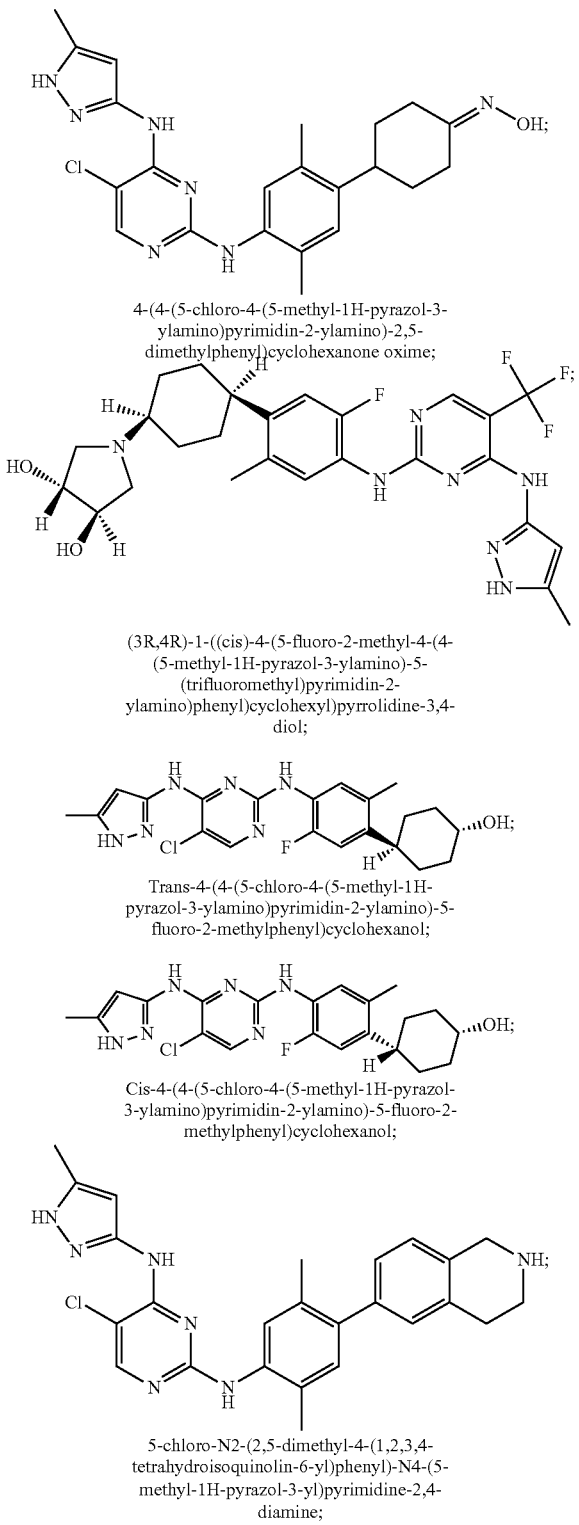

4-(4-(5-chloro-4-(5-methyl-1H-pyrazol-3-ylamino)pyrimidin-2-ylamino)-2,5-dimethylphenyl)cyclohexanone oxime;

(3R,4R)-1-((cis)-4-(5-fluoro-2-methyl-4-(4-(5-methyl-1H-pyrazol-3-ylamino)-5-(trifluoromethyl)pyrimidin-2-ylamino)phenyl)cyclohexyl)pyrrolidine-3,4-diol;

Trans-4-(4-(5-chloro-4-(5-methyl-1H-pyrazol-3-ylamino)pyrimidin-2-ylamino)-5-fluoro-2-methylphenyl)cyclohexanol;

Cis-4-(4-(5-chloro-4-(5-methyl-1H-pyrazol-3-ylamino)pyrimidin-2-ylamino)-5-fluoro-2-methylphenyl)cyclohexanol;

5-chloro-N2-(2,5-dimethyl-4-(1,2,3,4-tetrahydroisoquinolin-6-yl)phenyl)-N4-(5-methyl-1H-pyrazol-3-yl)pyrimidine-2,4-diamine;

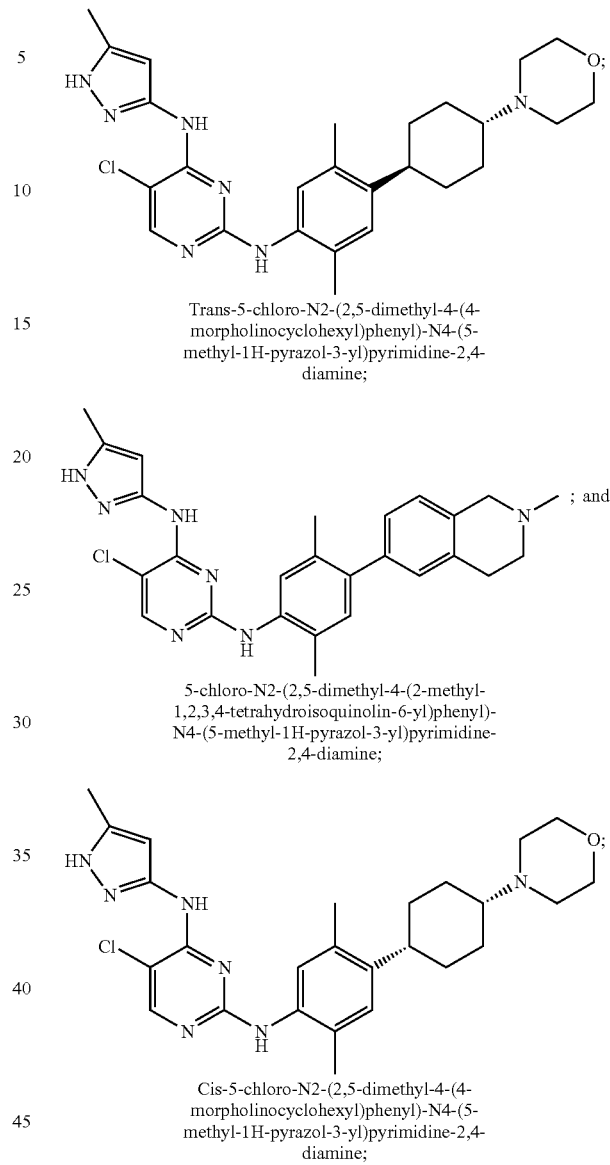

Trans-5-chloro-N2-(2,5-dimethyl-4-(4-morpholinocyclohexyl)phenyl)-N4-(5-methyl-1H-pyrazol-3-yl)pyrimidine-2,4-diamine;

5-chloro-N2-(2,5-dimethyl-4-(2-methyl-1,2,3,4-tetrahydroisoquinolin-6-yl)phenyl)-N4-(5-methyl-1H-pyrazol-3-yl)pyrimidine-2,4-diamine;

Cis-5-chloro-N2-(2,5-dimethyl-4-(4-morpholinocyclohexyl)phenyl)-N4-(5-methyl-1H-pyrazol-3-yl)pyrimidine-2,4-diamine;

or a pharmaceutical acceptable salt thereof.

6. A pharmaceutical composition comprising a therapeutically effective amount of a compound of a compound of claim 1 and a physiologically acceptable carrier.

7. The compound of claim 1, wherein X is quinolinyl, (1,2,3,4-tetrahydroisoquinolin-6-yl) or isoxazolyl, each of which is optionally substituted with $C_{1-6}$ alkyl, hydroxyl, or $C(O)NRR^7$ in which $R^7$ is H or $C_{1-6}$ alkyl and R is H or $C_{1-6}$ alkyl.

8. The compound of claim 1, wherein said compound is of Formula (5).

* * * * *